United States Patent

Miyake et al.

[11] Patent Number: 4,665,065
[45] Date of Patent: May 12, 1987

[54] 3-PYRAZOLO(1,5-A$\alpha$PYRIDINIUM CEPHEM COMPOUNDS

[75] Inventors: Akio Miyake, Hirakata; Masahiro Kondo, Osaka; Masahiko Fujino, Takarazuka, all of Japan

[73] Assignee: Takeda Chemical Industries, Ltd., Osaka, Japan

[21] Appl. No.: 739,440

[22] Filed: May 30, 1985

[30] Foreign Application Priority Data

Jun. 7, 1984 [WO] PCT Int'l Appl. ... PCT/JP84/00295
Apr. 1, 1985 [WO] PCT Int'l Appl. ... PCT/JP85/00155

[51] Int. Cl.$^4$ .................. A61K 31/545; C07D 501/46
[52] U.S. Cl. ..................... 574/202; 540/222
[58] Field of Search .......... 544/16, 17, 22, 26, 544/27; 514/202, 205, 206; 540/222

[56] References Cited

U.S. PATENT DOCUMENTS

| | | | |
|---|---|---|---|
| 4,024,133 | 5/1977 | Cook et al. | 540/222 |
| 4,033,950 | 7/1977 | Cook et al. | 540/222 |
| 4,098,888 | 7/1978 | Ochiari et al. | 540/222 |
| 4,258,041 | 3/1981 | O'Callaghan et al. | 540/2225 |
| 4,278,671 | 7/1981 | Ochiai et al. | 540/221 |
| 4,278,793 | 7/1981 | Durckheimer et al. | 540/227 |
| 4,500,526 | 2/1985 | Imae | 544/27 |
| 4,501,739 | 2/1985 | Lunn | 544/22 |

FOREIGN PATENT DOCUMENTS 0062321 10/1982 European Pat. Off. .
0149487 7/1985 European Pat. Off. ............... 544/27
2037281 7/1980 United Kingdom ................. 544/22

*Primary Examiner*—Robert J. Warden
*Assistant Examiner*—Robert Benson
*Attorney, Agent, or Firm*—Wegner & Bretschneider

[57] ABSTRACT

A compound of the formula;

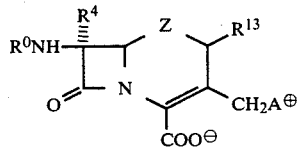

wherein $R^0$ stands for hydrogen atom, nitrogen-containing heterocyclic group, acyl group or amino-protecting group, Z stands for S, S→O, O or CH$_2$, $R^4$ stands for hydrogen atom, methoxy group or formamido group, $R^{13}$ stands for hydrogen atom, methyl group, hydroxyl group or halogen atom and A stands for an optionally substituted pyrazol-2-yl group forming a fused ring at the 1,5-position or a physiologically or pharmaceutically acceptable salt or ester thereof.

This compound is novel and has excellent antibacterial activity.

17 Claims, No Drawings

3-PYRAZOLO(1,5-AαPYRIDINIUM CEPHEM COMPOUNDS

This invention relates to novel antibacterial compounds having excellent antibacterial action, a method of preparing same and a pharmaceutical composition.

The present invention relates to a compound of the formula;

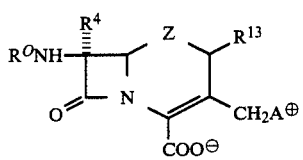

wherein $R^0$ stands for hydrogen atom, nitrogen-containing heterocyclic group, acyl group or amino-protecting group, Z stands for S, S→O, O or $CH_2$, $R^4$ stands for hydrogen atom, methoxy group or formamido group, $R^{13}$ stands for hydrogen atom, methyl group, hydroxyl group or halogen atom, and A stands for an optionally substituted pyrazol-2-yl group forming a fused ring at the 1,5-position or a physiologically or pharmaceutically acceptable salt or ester thereof, methods of preparing them and to pharmaceutical compositions. More specifically, the antibacterial compounds of the present invention are cephem compounds representable by the general formula [I] (Z=S, S→O) as well as oxa-(Z=O) or carba-(Z=$CH_2$) derivatives thereof.

The cephem compounds in the present specification are a group of compounds named on the basis of "cepham" disclosed in "The Journal of the American Chemical Society" Vol. 84, p. 3400 (1962), and include, among the cepham compounds, those having a double bond at the the 3,4-position.

The compounds of this invention have a characteristic feature in having at the 3-position a pyrazol-2-yl group which forms a fused ring at the 1,5-position. The present invention succeeded in synthesizing the compounds representable by the general formula [I] and having such a structural feature, and examined the antibacterial activities and antibacterial spectrum, resulting in the findings that the compounds [I] have strong antibacterial action against various bacteria, especially against cephalosporin-resistant bacteria, and that they show specific antibacterial action against bacteria belonging to the genus Pseudomonas, and completed the present invention.

Reference is made as follows to the group names and symbols used in the present specification. Unless otherwise specifically defined, those groups and symbols are of the following meanings respectively.

"Alkyl group" is preferably a straight-chain or branched lower alkyl group having 1–6 carbon atoms (hereinafter sometimes mentioned briefly as "$C_{1-6}$ alkyl group"), which is exemplified by methyl, ethyl, n-propyl, isopropyl, n-butyl, isobutyl, sec-butyl, tert-butyl, n-pentyl or n-hexyl.

"Alkenyl group" is preferably a straight-chain or branched lower alkenyl group having 2–6 carbon atoms (hereinafter sometimes mentioned briefly as "$C_{2-6}$ alkenyl group"), which is exemplified by vinyl, allyl, 1-propenyl, isopropenyl, 1-butenyl, 2-butenyl, 3-butenyl, methallyl, or 1,1-dimethylallyl.

"Alkynyl group" is preferably a straight-chain or branched lower alkynyl group having 2–6 carbon atoms (hereinafter sometimes mentioned briefly as "$C_{2-6}$ alkynyl group"), which is exemplified by ethynyl, 1-propynyl or propargyl.

"Cycloalkyl group" is preferably a 3–7 membered alicyclic hydrocarbon group having 3–10 carbon atoms (hereinafter sometimes mentioned briefly as "$C_{3-10}$ cycloalkyl group"), which is exemplified by cyclopropyl, cyclobutyl, cyclopentyl, cyclohexyl, cycloheptyl, norbornyl or adamantyl.

"Cycloalkenyl group" is preferably a 5–6 membered alicyclic hydrocarbon group having double bond (hereinafter sometimes mentioned briefly as "$C_{5-6}$ cycloalkenyl group"), which is exemplified by cyclopentenyl, cyclopentadienyl, cyclohexenyl or cyclohexadienyl.

"Aryl group" is preferably an aromatic hydrocarbon group having 6–10 carbon atoms (hereinafter sometimes mentioned briefly as "$C_{6-10}$ aryl group"), which is exemplified by phenyl, α-naphthyl, β-naphthyl or biphenylyl.

"Aralkyl group" is preferably an aryl-substituted alkyl group having 7–12 carbon atoms (hereinafter sometimes mentioned briefly as "$C_{7-12}$ aralkyl group"), which is exemplified by benzyl, 1-phenylethyl, 2-phenylethyl, phenylpropyl or naphthylmethyl. Additionally, the $C_{7-12}$ aralkyl group, in combination with the di-$C_{6-10}$ aryl-methyl group and tri-$C_{6-10}$ aryl-methyl group, is sometimes stated as "$C_{7-19}$ aralkyl group".

"Diarylmethyl group" means methyl group substituted with two $C_{6-10}$ aryl groups mentioned above (hereinafter sometimes mentioned briefly as "di-$C_{6-10}$ aryl-methyl group"), which is exemplified by benzhydryl.

"Triarylmethyl group" means methyl group substituted with three $C_{6-10}$ aryl groups mentioned above (hereinafter sometimes mentioned briefly as "tri-$C_{6-10}$ arylmethyl group"), which is exemplified by trityl.

The aryl group of "arylmethylene group" is preferably a $C_{6-10}$ aryl group mentioned above, hence "arylmethylene group" being hereinafter sometimes called "$C_{6-10}$ arylmethylene group", which is exemplified by benzylidene ($C_6H_5CH=$).

The alkyl group of "alkoxy group" is preferably a $C_{1-6}$ alkyl group mentioned above, hence "alkoxy group" being hereinafter sometimes called "$C_{1-6}$ alkoxy group", which is exemplified by methoxy, ethoxy, n-propoxy, isopropoxy, n-butoxy, tert-butoxy, amyloxy or hexyloxy.

The cycloalkyl group of "cycloalkyloxy group" is preferably a $C_{3-10}$ cycloalkyl group mentioned above, hence "cycloalkyloxy group" being hereinafter sometimes called "$C_{3-10}$ cycloalkyloxy group", which is exemplified by cyclopropyloxy, cyclopentyloxy, cyclohexyloxy or norbornyloxy.

The aryl group of "aryloxy group" is preferably a $C_{6-10}$ aryl group mentioned above, hence "aryloxy group" being hereinafter sometimes called "$C_{6-10}$ aryloxy group", which is exemplified by phenoxy or naphthyloxy.

The aralkyl group of "aralkyloxy group" is preferably a $C_{7-19}$ aralkyl group mentioned above, hence "aralkyloxy group" being hereinafter sometimes called "$C_{7-19}$ aralkyloxy group", which is exemplified by benzyloxy, 1-phenylethyloxy, 2-phenylethyloxy, naphthylmethyloxy, benzhydryloxy or trityloxy.

The alkyl group of "alkylthio group" is preferably a $C_{1-6}$ alkyl group mentioned above, hence "alkylthio group" being hereinafter sometimes called "$C_{1-6}$ alkylthio group", which is exemplified by methylthio, ethylthio, n-propylthio or n-butylthio.

The alkylthio group of "aminoalkylthio group" is preferably a $C_{1-6}$ alkylthio group mentioned above, hence "aminoalkylthio group" being hereinafter called "amino $C_{1-6}$ alkylthio group", which is exemplified by aminomethylthio, 2-aminoethylthio or 3-aminopropylthio.

The alkenyl group of "alkenylthio group" is preferably a $C_{2-6}$ alkenyl group mentioned above, hence "alkenylthio group" being hereinafter sometimes called "$C_{2-6}$ alkenylthio group", which is exemplified by vinylthio, allylthio, 1-propenylthio or isopropenylthio.

The cycloalkyl group of "cycloalkylthio group" is preferably a $C_{3-10}$ cycloalkyl group mentioned above, hence "cycloalkylthio group" being hereinafter sometimes called "$C_{3-10}$ cycloalkylthio group", which is exemplified by cyclopropylthio or cyclohexylthio.

The aryl group of "arylthio group" is preferably a $C_{6-10}$ aryl group mentioned above, hence "arylthio group" being hereinafter sometimes called "$C_{6-10}$ arylthio group", which is exemplified by phenylthio or naphthylthio.

The aralkyl group of "aralkylthio group" is preferably a $C_{7-19}$ aralkyl group mentioned above, hence "aralkylthio group" being hereinafter sometimes called "$C_{7-19}$ aralkylthio group", which is exemplified by benzylthio, phenylethylthio, benzhydrylthio or tritylthio.

The alkyl group of "monoalkylamino group" is preferably a $C_{1-6}$ alkyl group mentioned above, hence "monoalkylamino group" being hereinafter sometimes called "mono-$C_{1-6}$ alkylamino group", which is exemplified by methylamino, ethylamino, n-propylamino, n-butylamino, tert-butylamino, n-pentylamino or n-hexylamino.

The alkyl group of "dialkylamino group" is preferably a $C_{1-6}$ alkyl group mentioned above, hence "dialkylamino group" being hereinafter sometimes called "di-$C_{1-6}$ alkylamino group", which is exemplified by dimethylamino, diethylamino, methylethylamino, di-(n-propyl)amino or di-(n-butyl)amino.

The alkyl group of "trialkylammonium group" is preferably a $C_{1-6}$ alkyl group mentioned above, hence "trialkylammonium group" being hereinafter sometimes called "tri-$C_{1-6}$ alkylammonium group", which is exemplified by trimethylammonium [$(CH_3)_3N^{\oplus}—$] or triethylammonium. The trialkylammonium group is necessarily accompanied a corresponding anion exemplified by halogenide ion (chloride ion, bromide ion, iodide ion, etc.), sulfate ion, nitrate ion, carbonate ion, organic carboxylate ion (e.g. oxalate ion or trifluoroacetate ion), organic sulfonate ion (e.g. methanesulfonate ion or p-toluenesulfonate ion). The organic carboxylate ion and the organic sulfonate ion may sometimes be present in the same molecule.

The cycloalkyl group of "cycloalkylamino group" is preferably a $C_{3-10}$ cycloalkyl group mentioned above, hence "cycloalkylamino group" being hereinafter sometimes called "$C_{3-10}$ cycloalkylamino", which is exemplified by cyclopropylamino, cyclopentylamino or cyclohexylamino.

The aryl group of "arylamino group" is preferably a $C_{6-10}$ aryl group mentioned above, hence "arylamino group" being hereinafter sometimes called "$C_{6-10}$ arylamino group", which is exemplified by anilino or N-methylanilino.

The aralkyl group of "aralkylamino group" is preferably a $C_{7-19}$ aralkyl group mentioned above, hence "aralkylamino group" being hereinafter sometimes called "$C_{7-19}$ aralkylamino group", which is exemplified by benzylamino, 1-phenylethylamino, 2-phenylethylamino, benzhydrylamino or tritylamino.

"Cyclic amino group" means a group formed by removing the hydrogen atom on the nitrogen atom constituting a saturated or partially saturated nitrogen-containing heterocyclic ring, which is exemplified by 1H-tetrazol-1-yl, 1H-pyrrol-1-yl, pyrrolino, pyrrolidino, 1H-imidazol-1-yl, imidazolino, imidazolidino, 1H-pyrazol-1-yl, pyrazolino, pyrazolidino, piperidino, piperazino or morpholino.

The alkyl group of "hydroxyalkyl group" is preferably a $C_{1-6}$ alkyl group mentioned above, hence "hydroxyalkyl group" being hereinafter sometimes called "hydroxy $C_{1-6}$ alkyl group", which is exemplified by hydroxymethyl, 1-hydroxyethyl, 2-hydroxyethyl or 3-hydroxypropyl.

The alkyl group of "mercaptoalkyl group" is preferably a $C_{1-6}$ alkyl group mentioned above, hence "mercaptoalkyl group" being hereinafter sometimes called "mercapto $C_{1-6}$ alkyl group", which is exemplified by mercaptomethyl, 1-mercaptoethyl or 2-mercaptoethyl.

The alkoxy group of "alkoxyalkyl group" is preferably a $C_{1-6}$ alkoxy group mentioned above and the alkyl group of "alkoxyalkyl group" is preferably $C_{1-6}$ alkyl group mentioned above, hence "alkoxyalkyl group" being hereinafter sometimes called "$C_{1-6}$ alkoxy $C_{1-6}$ alkyl group", which is exemplified by methoxymethyl, ethoxymethyl or 2-methoxyethyl.

The alkylthio group of "alkylthioalkyl group" is preferably a $C_{1-6}$ alkylthio group mentioned above and the alkyl group of "alkylthioalkyl group" is preferably a $C_{1-6}$ alkyl group mentioned above, hence "alkylthioalkyl group" being hereinafter sometimes called "$C_{1-6}$ alkylthio $C_{1-6}$ alkyl group", which is exemplified by methylthiomethyl or 2-methylthioethyl.

The alkyl group of "aminoalkyl group" is preferably a $C_{1-6}$ alkyl group mentioned above, hence "aminoalkyl group" being hereinafter sometimes called "amino $C_{1-6}$ alkyl group", which is exemplified by aminomethyl, 2-aminoethyl or 3-aminopropyl.

"Monoalkylaminoalkyl group" is preferably a "mono-$C_{1-6}$ alkyl amino $C_{1-6}$ alkyl group", which is exemplified by methylaminomethyl, ethylaminomethyl, 2-(N-methylamino)ethyl or 3-(N-methylamino)propyl.

Dialkylaminoalkyl group is preferably a "di-$C_{1-6}$ alkylamino $C_{1-6}$ alkyl group", which is exemplified by N,N-dimethylaminomethyl, N,N-diethylaminomethyl, 2-(N,N-dimethylamino)ethyl, 2-(N,N-diethylamino)ethyl or 3-(N,N-diethylamino)propyl.

The cyclic amino group of "cyclic-amino alkyl group" is preferably the one mentioned above and the alkyl group of "cyclic-aminoalkyl group" is preferably a $C_{1-6}$ amino group mentioned above, hence hereinafter "cyclic-amino alkyl group" being sometimes called "cyclic-amino $C_{1-6}$ alkyl group", which is exemplified by pyrrolidinomethyl, piperidinomethyl, piperazinomethyl, morpholinomethyl or 2-(morpholino)ethyl.

The cyclic aminoalkyl group of "cyclic aminoalkylamino group" is preferably a cyclic-amino $C_{1-6}$ alkyl group mentioned above, hence hereinafter "cyclic aminoalkylamino group" being sometimes called "cyclic-amino $C_{1-6}$ alkylamino group", which is exemplified by pyrrolidinomethylamino, piperizinomethylamino, piperazinomethylamino or morpholinomethylamino.

The alkyl group of "halogenoalkyl group" is preferably a $C_{1-6}$ alkyl group mentioned above, hence hereinafter "halogenoalkyl group" being sometimes called "halogeno $C_{1-6}$ alkyl group", which is exemplified by fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-chloroethyl, 2,2-dichloroethyl, 2,2,2-trichloroethyl, 2-bromoethyl or 2-iodoethyl.

The alkyl group of "cyanoalkyl group" is preferably a $C_{1-6}$ alkyl group mentioned above, hence hereinafter "cyanoalkyl group" being sometimes called "cyano $C_{1-6}$ alkyl group", which is exemplified by cyanomethyl or 2-cyanoethyl.

The alkyl group of "carboxyalkyl group" is preferably a $C_{1-6}$ alkyl group mentioned above, hence hereinafter "carboxyalkyl group" being called sometimes "carboxy $C_{1-6}$ alkyl group", which is exemplified by carboxymethyl, 1-carboxyethyl or 2-carboxyethyl.

The alkyl group of "sulfoalkyl group" is preferably a $C_{1-6}$ alkyl group mentioned above, hence hereinafter "sulfoalkyl group" being called sometimes "sulfo $C_{1-6}$ alkyl group", which is exemplified by sulfomethyl or 2-sulfoethyl.

The alkanoyl group of "alkanoylalkyl group" is preferably a $C_{2-6}$ alkanoyl group mentioned hereafter and the alkyl group of "alkanoylalkyl group" is preferably a $C_{1-6}$ alkyl group mentioned above, hence hereinafter "alkanoylalkyl group" being sometimes called "$C_{2-6}$ alkanoyl $C_{1-6}$ alkyl group", which is exemplified by acetylmethyl, 1-acetylethyl or 2-acetylethyl.

The alkanoyloxy group of "alkanoyloxyalkyl group" is preferably a $C_{2-6}$ alkanoyloxy group to be described hereafter and the alkyl group of "alkanoyloxyalkyl group" is preferably a $C_{1-6}$ alkyl group mentioned above, hence hereinafter "alkanoyloxyalkyl group" being sometimes called "$C_{2-6}$ alkanoyloxy $C_{1-6}$ alkyl group", which is exemplified by acetoxymethyl, 1-acetoxyethyl or 2-acetoxyethyl.

The alkoxycarbonyl group of "alkoxycarbonylalkyl group" is preferably a $C_{1-10}$ alkoxy-carbonyl group to be described hereafter and the alkyl group of "alkoxycarbonylalkyl group" is preferably a $C_{1-6}$ alkyl group mentioned above, hence hereinafter "alkoxycarbonylalkyl group" being sometimes called "$C_{1-10}$ alkoxy-carbonyl $C_{1-6}$ alkyl group", which is exemplified by methoxycarbonylmethyl, ethoxycarbonylmethyl or tert-butoxycarbonylmethyl.

The alkyl group of "carbamoylalkyl group" is preferably a $C_{1-6}$ alkyl group, hence hereinafter "carbamoylalkyl group" being sometimes called "carbamoyl $C_{1-6}$ alkyl group", which is exemplified by carbamoylmethyl.

The alkyl group of "carbamoyloxyalkyl group" is preferably a $C_{1-6}$ alkyl group, hence hereinafter "carbamoylalkyl group" being called sometimes "carbamoyloxy $C_{1-6}$ alkyl group", which is exemplified by carbamoyloxymethyl.

"Halogen atom" is exemplified by fluorine, chlorine, bromine or iodine.

"Alkanoyl group" is preferably an aliphatic acyl group having 1–6 carbon atoms, hereinafter sometimes called simply "$C_{1-6}$ alkanoyl group", which is exemplified by formyl, acetyl, propionyl, butyryl, isobutyryl, valeryl, isovaleryl or pivaloyl. These alkanoyl groups, except formyl, are sometimes called "$C_{2-6}$ alkanoyl group".

"Alkenoyl group" is preferably the one having 3–5 carbon atoms (hereinafter sometimes simply called "$C_{3-5}$ alkenoyl group"), which is exemplified by acryloyl, crotonoyl or maleoyl.

The cycloalkyl group of "cycloalkylcarbonyl group" is preferably a $C_{3-10}$ cycloalkyl group mentioned above, hence hereinafter "cycloalkyl carbonyl group" being sometimes called "$C_{3-10}$ cycloalkyl-carbonyl group", which is exemplified by cyclopropylcarbonyl, cyclobutylcarbonyl, cyclopentylcarbonyl, cyclohexylcarbonyl, cycloheptylcarbonyl or adamantylcarbonyl.

The cycloalkenyl group of "cycloalkenylcarbonyl group" is preferably a $C_{5-6}$ cycloalkenyl group, hence hereinafter "cycloalkenylcarbonyl group" being called sometimes "$C_{5-6}$ cycloalkenyl-carbonyl group", which is exemplified by cyclopentenylcarbonyl, cyclopentadienylcarbonyl, cyclohexenylcarbonyl or cyclohexadienylcarbonyl.

The aryl group of "arylcarbonyl group" is preferably a $C_{6-10}$ aryl group mentioned above, hence hereinafter "arylcarbonyl group" being called sometimes "$C_{6-10}$ arylcarbonyl group", which is exemplified by benzoyl or naphthoyl.

The aralkyl group of "aralkylcarbonyl group" is preferably a $C_{7-19}$ aralkyl group, hence hereinafter "aralkylcarbonyl group" being sometimes called "$C_{7-19}$ aralkylcarbonyl group", which is exemplified by phenylacetyl, phenylpropionyl, α,α-diphenylacetyl or α,α,α-triphenylacetyl.

The alkyl group of "alkoxycarbonyl group" includes, in this specification, $C_{3-10}$ cycloalkyl group mentioned above, besides lower alkyl groups having 1–8 carbon atoms, hence hereinafter "alkoxycarbonyl group" being sometimes called "$C_{1-10}$ alkoxy-carbonyl group", which is exemplified by methoxycarbonyl, ethoxycarbonyl, n-propoxycarbonyl, isopropoxycarbonyl, n-butoxycarbonyl, isobutoxycarbonyl, tert-butoxycarbonyl, cyclopentyloxycarbonyl, cyclohexyloxycarbonyl or norbornyloxycarbonyl.

The aryloxy group of "aryloxycarbonyl group" is preferably a $C_{6-10}$ aryloxy group mentioned above, hence hereinafter "aryloxycarbonyl group" being sometimes called "$C_{6-10}$ aryloxy-carbonyl group", which is exemplified by phenoxycarbonyl or naphthyloxycarbonyl.

The aralkyloxy group of "aralkyloxycarbonyl group" is preferably a $C_{7-19}$ aralkyloxy group mentioned above, which is exemplified by benzyloxycarbonyl, benzhydryloxycarbonyl or trityloxycarbonyl.

"Substituted oxycarbonyl group" means the above-mentioned $C_{1-10}$ alkoxy-carbonyl group, $C_{6-10}$ aryloxycarbonyl group or $C_{7-19}$ aralkyloxy-carbonyl group.

The alkylthio group of "alkylthiocarbonyl group" is preferably a $C_{1-6}$ alkylthio group mentioned above, hence "alkylthiocarbonyl group" being hereinafter called sometimes "$C_{1-6}$ alkylthio-carbonyl group", which is exemplified by methylthiocarbonyl, ethylthiocarbonyl, n-propylthiocarbonyl or n-butylthiocarbonyl.

The alkanoyl group of "alkanoyloxy group" is preferably a $C_{1-6}$ alkanoyl group mentioned above, hence "alkanoyloxy group" being hereinafter called "$C_{1-6}$ alkanoyloxy group", which is exemplified by formyloxy, acetoxy, propionyloxy, butyryloxy, valeryloxy or pivaloyloxy. These alkanoyloxy groups, except formyloxy, are sometimes called "$C_{2-6}$ akanoyloxy group".

The alkenoyl group of "alkenoyloxy group" is preferably a $C_{3-5}$ alkenoyl group mentioned above, hence "alkenoyloxy group" being hereinafter called sometimes "C$_{3-5}$ alkenoyloxy group", which is exemplified by acryloyloxy or crotonoyloxy.

The alkyl group of "monoalkylcarbamoyl group" is preferably a C$_{1-6}$alkyl group mentioned above, hence "monoalkylcarbamoyl group" being hereinafter sometimes called "mono-C$_{1-6}$ alkylcarbamoyl group", which is exemplified by N-methylcarbamoyl or N-ethylcarbamoyl.

The alkyl group of "dialkylcarbamoyl group" is preferably a C$_{1-6}$alkyl group, hence "dialkylcarbamoyl group" being hereinafter sometimes called "di-C$_{1-6}$ alkylcarbamoyl group", which is exemplified by N,N-dimethylcarbamoyl or N,N-diethylcarbamoyl.

The monoalkylcarbamoyl group of "monoalkylcarbamoyloxy group" is preferably a mono-C$_{1-6}$ alkylcarbamoyl group mentioned above, hence "monoalkylcarbamoyloxy group" being hereinafter sometimes called "mono-C$_{1-6}$ alkylcarbamoyloxy group", which is exemplified by N-methylcarbamoyloxy or N-ethylcarbamoyloxy.

The dialkylcarbamoyl group of "dialkylcarbamoyloxy group" is preferably a di-C$_{1-6}$ alkylcarbamoyl group mentioned above, hence "dialkylcarbamoyloxy group" being hereinafter sometimes called "di-C$_{1-6}$ alkylcarbamoyloxy group", which is exemplified by N,N-dimethylcarbamoyloxy or N,N-diethylcarbamoyloxy.

The alkyl group of "alkylsulfonyl group" is preferably a C$_{1-6}$alkyl group mentioned above, hence "alkylsulfonyl group" being hereinafter sometimes called "C$_{1-6}$ alkylsulfonyl group", which is exemplified by methanesulfonyl or ethanesulfonyl.

The aryl group of "arylsulfonyl group" is preferably a C$_{6-10}$ aryl group mentioned above, hence "arylsulfonyl group" being hereinafter sometimes called "C$_{6-10}$ arylsulfonyl group", which is exemplified by, among others, benzenesulfonyl.

The aralkyl group of "aralkylsulfonyl group" is preferably a C$_{7-19}$aralkyl group mentioned above, hence "aralkylsulfonyl group" being hereinafter sometimes called "C$_{7-19}$ aralkylsulfonyl group", which is exemplified by phenylmethanesulfonyl or diphenylmethanesulfonyl.

The alkylsulfonyl group of "alkylsulfonyloxy group" is preferably a C$_{1-6}$alkylsulfonyl group mentioned above, hence "alkylsulfonyloxy group" being hereinafter sometimes called "C$_{1-6}$ alkylsulfonyloxy group", which is exemplified by methanesulfonyloxy or ethanesulfonyloxy.

The arylsulfonyl group of "arylsulfonyloxy group" is preferably a C$_{6-10}$arylsulfonyl group, hence "arylsulfonyloxy group" being hereinafter sometimes called "C$_{6-10}$ arylsulfonyloxy group", which is exemplified by, among others, benzenesulfonyloxy.

The aralkylsulfonyl group of "aralkylsulfonyloxy group" is preferably a C$_{7-19}$ aralkylsulfonyl group mentioned above, hence "aralkylsulfonyloxy group" being hereinafter sometimes called "C$_{7-19}$ arylsulfonyloxy group", which is exemplified by phenylmethanesulfonyloxy or diphenylmethanesulfonyloxy.

"Amino acid residue" means acyl groups formed by removing hydroxyl group of the carboxyl group of conventional amino acids, which is exemplified by glycyl, alanyl, valyl, leucyl, isoleucyl, seryl, threonyl, cysteinyl, cystinyl, methionyl, aspartyl, glutamyl, lysyl, arginyl, phenylglycyl, phenylalanyl, tyrosyl, histidyl, tryptophanyl or prolyl.

"Nitrogen-containing heterocyclic ring" means 5-8 membered ring containing one to several, preferably 1-4, nitrogen atoms (optionally oxidized) or fused ring thereof, which may contain, besides nitrogen atoms, one to several, preferably 1-2, hetero atoms such as oxygen atom or sulfur atom.

"Nitrogen-containing heterocyclic group" means a group formed by removing one hydrogen atom from a carbon atom constituting the above nitrogen-containing heterocyclic ring.

"Heterocyclic group" means a group formed by removing one hydrogen atom from a carbon atom constituting the heterocyclic ring, which means 5-8 membered ring containing one to several, preferably 1-4, hetero atoms such as nitrogen atom (optionally oxidized), oxygen atom or sulfur atom, or fused ring thereof, which is exemplified by 2- or 3-pyrrolyl, 3-, 4- or 5-pyrazolyl, 2-, 4- or 5-imidazolyl, 1,2,3- or 1,2,4-triazolyl, 1H- or 2H-tetrazolyl, 2- or 3-furyl, 2- or 3-thienyl, 2-, 4- or 5-oxazolyl, 3-, 4- or 5-isoxazolyl, 1,2,3-oxadiazol-4- or 5-yl, 1,2,4-oxadiazol-3- or 5-yl, 1,2,5- or 1,3,4-oxadiazolyl, 2-, 4- or 5-thiazolyl, 3-, 4- or 5-isothiazolyl, 1,2,3-thiadiazol-4- or 5-yl, 1,2,4-thiadiazol-3- or 5-yl, 1,2,5- or 1,3,4-thiadiazolyl, 2- or 3-pyrrolidinyl, 2-, 3- or 4-pyridyl, 2-, 3- or 4-pyridyl-N-oxide, 3- or 4-pyridazinyl, 3- or 4-pyridazinyl-N-oxide, 2-, 4- or 5-pyrimidinyl, 2-, 4- or 5-pyrimidinyl-N-oxide, pyrazinyl, 2-, 3- or 4-piperidinyl, piperazinyl, 3H-indol-2- or 3-yl, 2-, 3- or 4-pyranyl, 2-, 3- or 4-thiopyranyl, benzopyranyl, quinolyl, pyrido[2,3-d]pyrimidyl, 1,5-, 1,6-, 1,7-, 1,8-, 2,6- or 2,7-naphthylidyl, thieno[2,3-d]pyridyl, pyrimidopyrimidyl, pyrazinoquinolyl, or benzopyranyl.

Heterocyclic groups of "heterocycle-oxy group", "heterocycle-thio group", "heterocycle-amino group", "heterocycle-carbonyl group", "heterocycle-acetyl group" and "heterocycle-carboxamido group" are all preferably "heterocyclic group" mentioned above.

"Quaternary ammonium group" means a group formed by quaternarizing one of the tertiary nitrogen atoms constituting the above-mentioned nitrogen-containing heterocyclic ring, and is necessarily accompanied with a counter anion. The quaternary ammonium group is isothiazolium, pyridinium or quinolinium. The anion is exemplified by hydroxide ion, halogenide ion (e.g. chloride ion, bromide ion or iodide ion), sulfate ion, nitrate ion, carbonate ion, organic carboxylate ion (e.g. oxalate ion or trifluoroacetate ion) or organic sulfonate ion (e.g. p-toluenesulfonate ion), and in the latter two cases they are often present as intramolecular ion pair.

The groups bearing asterisk * at the right shoulder are "optionally substituted groups". For example, alkyl* group means "optionally substituted alkyl group". The number of substituents is not always restricted to one, but may be, depending on the substituents, two to several, preferably 2-3, and those substituents may be of the same or different kind.

"C$_{6-10}$ aryl* group", "C$_{7-12}$ aralkyl* group", "C$_{6-10}$ aryl*oxy group" and "C$_{7-19}$ aralkyl*oxy group" are preferably "phenyl* group", "benzyl* group", "phenoxy* group" and "benzyl*oxy group", respectively.

In the compound [I] of the present invention, the substituent R$^0$ stands for hydrogen atom, nitrogen-containing heterocyclic group, acyl group or amino-protecting group. Among them, those compounds [I] in which R$^0$ is nitrogen-containing heterocyclic group or acyl group have a strong antibacterial action against various bacteria, especially against cephalosporin-resistant bacteria, and they show specific antibacterial action against bacteria belonging to the genus Pseudomonas. On the other hand, compounds [I], wherein $R^0$ is hydrogen atom or amino-protecting group, are useful intermediates for producing compounds [I] wherein $R^0$ is nitrogen-containing heterocyclic group or acyl group.

The nitrogen-containing heterocyclic group (hereinafter sometimes denoted as the symbol $R^a$) as the substituent $R^0$ is a "nitrogen-containing heterocyclic group" as mentioned above, which is exemplified by 2-pyrrolyl, 3-pyrrolyl, 3-pyrazolyl, 4-pyrazolyl, 5-pyrazolyl, 2-imidazolyl, 4-imidazolyl, 5-imidazolyl, 1,2,3-triazolyl, 1,2,4-triazolyl, 1H-tetrazolyl, 2H-tetrazolyl, 2-oxazolyl, 4-oxazolyl, 5-oxazolyl, 3-isoxazolyl, 4-isoxazolyl, 5-isoxazolyl, 1,2,3-oxadiazol-4-yl, 1,2,3-oxadiazol-5-yl, 1,2,4-oxadiazol-3-yl, 1,2,4-oxadiazol-5-yl, 1,2,5-oxadiazolyl, 1,3,4-oxadiazolyl, 2-thiazolyl, 4-thiazolyl, 5-thiazolyl, 4-isothiazolyl, 4-isothiazolyl, 5-isothiazolyl, 1,2,3-thiadiazol-4-yl, 1,2,3-thiadiazol-5-yl, 1,2,4-thiadiazol-3-yl, 1,2,4-thiadiazol-5-yl, 1,2,5-thiadiazolyl, 1,3,4-thiadiazolyl, 2-pyrrolidinyl, 3-pyrrolidinyl, 2-pyridyl, 3-pyridyl, 4-pyridyl, 2-pyridyl-N-oxide, 3-pyridyl-N-oxide, 4-pyridyl-N-oxide, 3-pyridazinyl, 4-pyridazinyl, 3-pyridazinyl-N-oxide, 4-pyridazinyl-N-oxide, 2-pyrimidinyl, 4-pyrimidinyl, 5-pyrimidinyl, 2-pyrimidinyl-N-oxide, 4-pyrimidinyl-N-oxide, 5-pyrimidinyl-N-oxide, pyrazinyl, 2-piperidinyl, 3-piperidinyl, 4-piperidinyl, piperazinyl, 3H-indol-2-yl, or 3H-indol-3-yl, especially preferably 2-pyridyl, 3-pyridyl, 4-pyridyl, 2-imidazolyl, 4-imidazolyl or 5-imidazolyl.

The above-mentioned nitrogen-containing heterocyclic groups may have one or more substituents on the ring, in the number of two to several, preferably 2-3, which may be the same or different depending on the kinds of the substituents. These substituents on the nitrogen-containing heterocyclic ring are exemplified by an alkyl group, cycloalkyl group, aryl group, aralkyl group, hydroxyl group, alkoxy group, mercapto group, alkylthio group, amino group, monoalkylamino group, dialkylamino group, halogen atom, nitro group, azido group, cyano group, carboxyl group, alkoxycarbonyl group, alkanoyl group, alkanoyloxy group, carbamoyl group, monoalkylcarbamoyl group, dialkylcarbamoyl group, carbamoyloxy group, monoalkylcarbamoyloxy group or dialkylcarbamoyloxy group.

As the nitrogen-containing heterocyclic group having one or more substituents, especially preferable are 2-imidazolyl group having as substituents the above-mentioned alkyl group, aryl group or halogen atom, or N-substituted pyridinium-4-yl groups having as substituents the above-mentioned alkyl group or aralkyl group on the nitrogen atom of the 4-pyridyl group to thereby quaternarize the nitrogen atom. The substituted 2-imidazolyl group is exemplified by 1-methyl-2-imidazolyl or 4-chloro-2-imidazolyl, and the N-substituted pyridinium-4-yl group is exemplified by N-methylpyridinium-4-yl, N-ethylpyridinium-4-yl, N-benzylpyridinium-4-yl or N-(p-fluorobenzyl)pyridinium-4-yl, respectively.

The acyl group (hereinafter sometimes denoted as the symbol $R^b$) as the substituent $R^0$ means the acyl group substituted on the amino group at the 6-position of conventional penicillin derivatives or the acyl group substituted on the amino group at the 7-position of conventional cephalosporin derivatives. Such an acyl group is exemplified by alkanoyl group, alkenoyl group, cycloalkyl-carbonyl group, cycloalkenyl-carbonyl group, aryl-carbonyl group or heterocycle-carbonyl group which may be substituted, and more specifically $C_{1-6}$ alkanoyl* group, $C_{3-5}$ alkenoyl* group, $C_{3-10}$ cycloalkyl-carbonyl group, $C_{5-6}$ cycloalkenyl-carbonyl group, $C_{6-10}$ aryl*-carbonyl group and heterocycle*carbonyl group, respectively.

The $C_{1-6}$ alkanoyl group is exemplified by formyl, acetyl, propionyl, butyryl, isobutyryl, valeryl, isovaleryl and pivaloyl.

The substituents of "optionally substituted $C_{1-6}$ alkanoyl group" represented by the $C_{1-6}$ alkanoyl* group are exemplified by (1) heterocycle*carbonyl group in case of $C_1$ alkanoyl (i.e. formyl) and (2) "substituent $S^1$" described below in case of $C_{2-6}$ alkanoyl group (i.e. acetyl, propionyl, butyryl, isobutyryl valeryl, isovaleryl, pivaloyl, etc.). The "substituent $S^1$" is exemplified by $C_{3-10}$ cycloalkyl* group $C_{5-6}$ cycloalkenyl* group, $C_{6-10}$ aryl* group, hydroxyl group, $C_{1-6}$ alkoxy group, $C_{3-10}$ cycloalkyloxy group, $C_{6-10}$ aryl*oxy group, $C_{7-19}$ aralkyl*oxy group, mercapto group, $C_{1-6}$ alkyl*thio group, amino $C_{1-6}$ alkylthio group, $C_{2-6}$ alkenyl*thio group, $C_{3-10}$ cycloalkylthio group, $C_{6-10}$ aryl*thio group, $C_{7-19}$ aralkyl*thio group, amino group, mono-$C_{1-6}$ alkylamino group, di-$C_{1-6}$ alkylamino group, $C_{3-10}$ cycloalkylamino group, $C_{6-10}$ aryl*amino group, $C_{7-19}$ aralkyl*amino group, cyclic amino* group, halogen atom, nitro group, azido group, cyano group, carboxyl group, acyl+ group, substituted oxycarbonyl group, $C_{1-6}$ alkylthio-carbonyl group, acyl+oxy group, acyl+amino group, acyl+aminoalkylthio group, carbamoyl group, mono-$C_{1-6}$ alkylcarbamoyl group, di-$C_{1-6}$ alkylcarbamoyl group, carbamoyloxy group, mono-$C_{1-6}$ alkylcarbamoyloxy group, di-$C_{1-6}$ alkylcarbamoyloxy group, sulfo group, hydroxysulfonyloxy group, $C_{1-6}$ alkylsulfonyl group, $C_{6-10}$ aryl*sulfonyl group, $C_{7-19}$ aralkyl*sulfonyl group, $C_{1-6}$ alkylsulfonyloxy group, $C_{6-10}$ aryl*sulfonyloxy group, $C_{7-19}$ aralkyl*sulfonyloxy group, ureido* group, sulfamoyl* group, heterocyclic* group, heterocycle*oxy group, heterocycle*thio group, heterocycle*amino group, heterocycle*carbonyl group, heterocycle*carboxamido group or quaternary ammonium* group. The number of these substituents is not restricted to one, and in case there are two or more substituents, these substituents may be the same or different. To state further, two of these substituents may be combined to form C=C double bond or C=N double bond as described below.

The substituents (hereinafter referred to as "substituent $S^2$") of "optionally substituted $C_{3-5}$ alkenoyl group" are exemplified by $C_{3-10}$ cycloalkyl group, $C_{6-10}$ aryl* group, $C_{1-6}$ alkoxy group, $C_{6-10}$ aryl*oxy group, $C_{7-19}$ aralkyl*oxy group, halogen atom, cyano group, carboxyl group, acyl+ group, substituted oxycarbonyl group, acyl+oxy group, heterocyclic* group or quaternary ammonium* group.

The substituents of "optionally substituted $C_{6-10}$ arylcarbonyl group" represented by $C_{6-10}$ aryl*carbonyl group as well as "optionally substituted heterocyclic group" represented by heterocycle*carbonyl group (hereinafter collectively referred to as "substituent $S^3$" are exemplified by $C_{1-6}$ alkyl group, $C_{2-6}$ alkenyl group, $C_{6-10}$ aryl group, $C_{7-12}$ aralkyl group, di-$C_{6-10}$ arylmethyl group, tri-$C_{6-10}$ aryl-methyl group, hydroxyl group, $C_{1-6}$ alkoxy group, $C_{6-10}$ aryloxy group, $C_{7-19}$ aralkyloxy group, mercapto group, $C_{1-6}$ alkylthio group, $C_{6-10}$ arylthio group, $C_{7-19}$ aralkylthio group, amino group, mono-$C_{1-6}$ alkylamino group, di-$C_{1-6}$ alkylamino group, hydroxy $C_{1-6}$ alkyl group, mercapto $C_{1-6}$ alkyl group, halogeno-$C_{1-6}$ alkyl group, carboxy $C_{1-6}$ alkyl group, halogen atom, nitro group, azido group, cyano group, carboxyl group, substituted oxycarbonyl group, acyl+ group, acyl+oxy group, acyl+amino group, carbamoyl group, thiocarbamoyl group, $C_{1-6}$ alkylsulfonyl group, $C_{6-10}$ arylsulfonyl group or $C_{7-19}$ aralkylsulfonyl group.

Among the above-mentioned substituents ($S^1$, $S^2$ and $S^3$) of $C_{1-6}$ alkanoyl group, $C_{3-5}$ alkenoyl group, $C_{6-10}$ aryl-carbonyl group and heterocycle*carbonyl group, those which are not described below are of the same meaning as afore-mentioned.

The substituents of the $C_{6-10}$ aryl group of $C_{6-10}$ aryl* group, phenyl* group, $C_{6-10}$ aryl*oxy group, phenoxy* group, $C_{6-10}$ aryl*thio group, $C_{6-10}$ aryl*amino group, $C_{6-10}$ aryl*sulfonyl group and $C_{6-10}$ aryl*sulfonyloxy group are also of the class of the above-mentioned substituents $S^3$.

The substituents of the aromatic ring of the $C_{7-12}$ or $C_{7-19}$ aralkyl groups of $C_{7-12}$ aralkyl* group, benzyl* group, $C_{7-19}$ aralkyl*oxy group, benzyl*oxy group, $C_{7-19}$ aralkyl*thio group, $C_{7-19}$ aralkyl*amino group, $C_{7-19}$ aralkyl*sulfonyl group and $C_{7-19}$ aralkyl*sulfonyloxy group are also of the class of the above-mentioned substituents $S^3$.

The substituents of the heterocyclic ring of heterocyclic* group, heterocycle*oxy group, heterocycle*thio group, heterocycle*amino group, heterocycle*acetyl group and heterocycle*carboxamido group are also of the class of the above-mentioned substituents $S^3$.

The substituents on the nitrogen-containing heterocyclic ring of quaternary ammonium* group are also of the class of the above-mentioned substituents $S^3$.

The substituents of the $C_{1-6}$ alkyl group of "optionally substituted $C_{1-6}$ alkyl group" representable by $C_{1-6}$ alkyl* group are also of the class of the above-mentioned substituents $S^1$.

The substituents of the "optionally substituted $C_{3-10}$ cycloalkyl group" and "optionally substituted $C_{5-6}$ cycloalkenyl group" representable by $C_{3-10}$ cycloalkyl group and $C_{5-6}$ cycloalkenyl* group are also of the class of the above-mentioned substituents $S^3$.

The substituents of the $C_{1-6}$ alkylthio groups of "optionally substituted $C_{1-6}$ alkylthio group" representable by $C_{1-6}$ alkyl*thio group (these substituents are hereinafter referred to as "substituent $S^4$") are exemplified by hydroxyl group, $C_{1-6}$ alkoxy group, $C_{3-10}$ cycloalkyloxy group, $C_{6-10}$ aryl*oxy group, $C_{7-19}$ aralkyl*oxy group, mercapto group, $C_{1-6}$ alkylthio group, $C_{3-10}$ cycloalkylthio group, $C_{6-10}$ aryl*thio group, $C_{7-19}$ aralkyl*thio group, amino group, mono-$C_{1-6}$ alkylamino group, di-$C_{1-6}$ alkylamino group, cyclic amino* group, halogen atom, cyano group, carboxyl group, carbamoyl group, acyl+oxy group, sulfo group, or quaternary ammonium* group.

The substituents of the $C_{2-6}$ alkenylthio group of "optionally substituted $C_{2-6}$ alkenylthio group" representable by a $C_{2-6}$ alkenyl*thio group (these substituents are hereinafter referred to as "substituent $S^5$") are exemplified by halogen atom, cyano group, carboxyl group, carbamoyl group, mono-$C_{1-6}$ alkylcarbamoyl group, di-$C_{1-6}$ alkylcarbamoyl group or thiocarbamoyl group.

"Acyl+ group" means the above-mentioned $C_{1-6}$ alkanoyl group, $C_{6-10}$ aryl*carbonyl group, $C_{7-19}$ aralkyl*carbonyl group, heterocycle*carbonyl group or heterocycle*acetyl group. Representative acyl+ groups are exemplified by formyl, acetyl, propionyl, n-butyryl, isobutyryl, valeryl, pivaloyl, n-hexanoyl, chloroacetyl, dichloroacetyl, trichloroacetyl, 3-oxobutyryl, 4-chloro-3-oxobutyryl, 3-carboxypropionyl, 4-carboxybutyryl, 3-ethoxycarbamoylpropionyl, benzoyl, naphthoyl, p-methylbenzoyl, p-hydroxybenzoyl, p-methoxybenzoyl, p-chlorobenzoyl, p-nitrobenzoyl, o-carboxybenzoyl, o-(ethoxycarbonylcarbamoyl)benzoyl, o-(ethoxycarbonylsulfamoyl)benzoyl, phenylacetyl, p-methylphenylacetyl, p-hydroxyphenylacetyl, p-methoxyphenylacetyl, 2,2-diphenylacetyl, 2-thienylcarbonyl, 2-furylcarbonyl, 2-, 4- or 5-thiazolylacetyl, 2- or 3-thienylacetyl, 2- or 3-furylacetyl, 2-amino-4- or 5-thiazolylacetyl or 5-amino-3-thiadiazolylacetyl.

The acyl+ group of "acyl+oxy group and "acyl+amino group" means the above-mentioned acyl+ group. Therefore, "acyl+oxy group" is exemplified by formyloxy, acetoxy, propionyloxy, butyryloxy, valeryloxy, pivaloyloxy, chloroacetoxy, dichloroacetoxy, trichloroacetoxy, 3-oxobutyryloxy, 4-chloro-3-oxobutyryloxy, 3-carboxypropionyloxy, 4-carboxybutyryloxy, 3-ethoxycarbamoylpropionyloxy, benzoyloxy, naphthoyloxy, p-methylbenzoyloxy, p-methoxybenzoyloxy, p-chlorobenzoyloxy, o-carboxybenzoyloxy, o-(ethoxycarbonylcarbamoyl)benzoyloxy, o-(ethoxycarbonylsulfamoyl)benzoyloxy, phenylacetyloxy, p-methylphenylacetyloxy, p-methoxyphenylacetyloxy, p-chlorophenylacetyloxy, 2,2-diphenylacetyloxy, thienylcarbonyloxy, furylcarbonyloxy, thiazolylacetyloxy, thienylacetyloxy or furylacetyloxy, and "acyl+amino group" is exemplified by acetamido ($CH_3CONH-$), benzamido ($C_6H_5CONH-$), phenylacetamido ($C_6H_5CH_2CONH-$) or 2-thienylacetamido

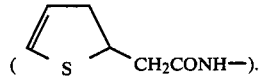

The acyl+amino group and alkylthio group of "acyl+aminoalkylthio group" mean respectively the above-mentioned acyl+amino group and $C_{1-6}$ alkylthio group, hence such "acyl+amino $C_{1-6}$ alkylthio group" are exemplified by acetamidomethylthio or 2-acetamidoethylthio.

"Arylacyl+ group" is preferably "$C_{6-10}$ aryl-acyl+ group", which is exemplified by benzoyl, phthaloyl. naphthoyl or phenylacetyl.

"Arylacyl+oxy group" is preferably "$C_{6-10}$ arylacyl+oxy group", as exemplified by benzoyloxy, naphthoyloxy or phenylacetyloxy.

The substituents of the ureido group of "optionally substituted ureido group" represented by "ureido* group" are exemplified by $C_{1-6}$ alkyl group, $C_{6-10}$ aryl* group, $C_{7-19}$ aralkyl* group, acyl+ group, carbamoyl group, sulfo group (which may form a salt with e.g. sodium or potassium), sulfamoyl group or amidino group.

The substituents of the sulfamoyl group of "optionally substituted sulfamoyl group" represented by "sulfamoyl* group" are exemplified by $C_{1-6}$ alkyl group or amidino group.

The substituents of "optionally substituted carbamoyl group" representable by "carbamoyl* group" and "carbamoyl*oxy group" are exemplified by $C_{1-6}$ alkyl group, $C_{6-10}$ aryl* group, $C_{7-12}$ aralkyl* group or acyl+ group, including the case where the nitrogen atom of carbamoyl group is the ring-forming nitrogen atom of the nitrogen-containing heterocyclic ring.

The substituents of "optionally substituted thiocarbamoyl group" represented by "thiocarbamoyl* group" are exemplified by $C_{1-6}$ alkyl group, $C_{6-10}$ aryl* group, $C_{7-12}$ aralkyl* group or acyl+ group, including the case where the nitrogen atom of thiocarbamoyl group is the ring-forming nitrogen atom of the nitrogen-containing heterocyclic ring.

The substituents of the cyclic amino group of "optionally substituted cyclic amino group" represented by cyclic amino* group" (these substituents are hereinafter referred to as "substituent $S^6$") are exemplified by $C_{1-6}$ alkyl group, $C_{2-6}$ alkenyl group, $C_{3-10}$ cycloalkyl group, $C_{6-10}$ aryl* group, $C_{7-12}$ aralkyl* group, di-$C_{6-10}$ aryl-methyl group, tri-$C_{6-10}$ aryl-methyl group, hydroxyl group, $C_{1-6}$ alkoxy group, $C_{6-10}$ aryl*oxy group, $C_{7-19}$ aralkyl*oxy group, mercapto group, $C_{1-6}$ alkylthio group, $C_{6-10}$ aryl*thio group, $C_{7-19}$ aralkyl*thio group, amino group, mono-$C_{1-6}$ alkylamino group, di-$C_{1-6}$ alkylamino group, $C_{6-10}$ aryl*amino group, $C_{7-19}$ aralkyl-*amino group, halogen atom, nitro group, azido group, oxo group, thioxo group, cyano group, carboxyl group, acyl+ group, substituted oxycarbonyl group, acyl-+oxy group, acyl+amino group, carbamoyl group, carbamoyloxy group, thiocarbamoyl group or sulfo group.

The formyl group substituted with the heterocycle*-carbonyl group mentioned above as one of the $C_{1-6}$ alkanoyl* groups is an acyl group having a formula of heterocycle*-CO—CO—, and the heterocyclic* group is also depicted here by those groups exemplified before, but preferably is, optionally substituted oxazolyl group, thiazolyl group, oxadiazolyl group or thiadiazolyl group, for example. These heterocycle*-CO—CO— groups are exemplified by 2-(2-, 4- or 5-oxazolyl)-2-oxoacetyl, 2-(2-, 4- or 5-thiazolyl)-2-oxoacetyl, 2-(2-amino-4-thiazolyl)-2-oxoacetyl, 2-(1,2,4-oxadiazol-3- or 5-yl)-2-oxoacetyl, 2-(1,2,4-thiadiazol-3- or 5-yl)-2-oxoacetyl or 2-(5-amino-1,2,4-thiadiazol-3-yl)-2-oxoacetyl.

The $C_{2-6}$ alkanoyl* group is most preferably a substituted acetyl group. The number of substituents of the substituted acetyl group is 1–3, and, as these substituents, "substituent $S^1$" mentioned above as substituents of $C_{1-6}$ alkanoyl groups are also mentioned here. When the number of substituents is 2–3, these substituents may be the same or different, and two of them may be combined to form a double bond. Mono- and di-substituted acetyl groups can be shown by $R^{15}CH_2CO—$ and

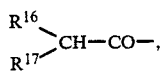

respectively. On the other hand, preferable tri-substituted acetyl groups are those in which two of the substituents are combined to form C=C double bond or C=N double bond, which can be shown by

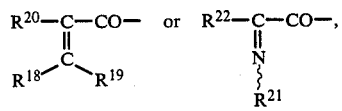

respectively,
wherein $R^{15}$–$R^{17}$, $R^{20}$ and $R^{22}$ mean the above-mentioned substituent ($S^1$), and $R^{18}$, $R^{19}$ and $R^{21}$ will be described hereafter. The detailed description about acetyl groups having these substituents ($R^{15}$–$R^{22}$) is given as follows.

$$R^{15}CH_2CO— \quad (i)$$

The symbol $R^{15}$ means the above-mentioned substituents ($S^1$) of a $C_{1-6}$ alkyl group, and use is often made of particularly a $C_{5-6}$ cycloalkenyl group, $C_{6-10}$ aryl* group, $C_{6-10}$ aryl*oxy group, $C_{1-6}$ alkyl*thio group, $C_{2-6}$ alkenyl*thio group, $C_{6-10}$ aryl*thio group, amino group, cyclic amino group, cyano group, acyl+ group, acyl-+oxy group, heterocyclic* group, heterocycle*thio group or quaternary ammonium* group, for example. Acyl groups of $R^{15}CH_2CO—$ are exemplified by 1,4-cyclohexadienylacetyl, phenylacetyl, p-tolylacetyl, p-hydroxyphenylacetyl, p-methoxyphenylacetyl, p-chlorophenylacetyl, o-aminomethylphenylacetyl, phenoxyacetyl, p-hydroxyphenoxyacetyl, p-chlorophenoxyacetyl, cyanomethylthioacetyl, difluoromethylthioacetyl, trifluoromethylthio acetyl, (2-carboxyethyl)thioacetyl, (2-amino-2-carboxyethyl)thioacetyl, (2-chlorovinyl)thioacetyl, (2-carboxyvinyl)thioacetyl, (2-fluoro-2-carbamoylvinyl)thioacetyl, (1,2-dichlorovinyl)thioacetyl, (2-chloro-2-carboxyvinyl)thioacetyl, phenylthioacetyl, p-hydroxyphenylthioactyl, glycyl, 1H-tetrazolyl-1-ylacetyl, 3,5-dichloro-4-oxo-1,4-dihydropyridin-1-yl -acetyl, cyanoacetyl, acetoacetyl, benzoylacetyl, furylcarbonylacetyl, thienylcarbonylacetyl, (1H-tetrazolyl)acetyl, 1-methyl-1H-tetrazolylacetyl, (2-furyl)acetyl, (2-thienyl)acetyl, (3-thienyl)acetyl, (4-oxazolyl)acetyl, (4-thiazolyl)acetyl, (2-amino-4-thiazolyl)acetyl, (1,2,4-thiadiazol-3-yl)acetyl, (5-amino-1,2,4-thiadiazol-3-yl)acetyl, (2-pyridyl)acetyl, (4-pyridyl)acetyl, (2-imidazolyl)thioacetyl, (2-pyridyl)thioacetyl, (4-pyridyl)thioacetyl, (2-thienyl)thioacetyl, hydroxypyridylthioacetyl, (5-isothiazolyl)thioacetyl, (3-methylthio-5-isothiazolyl)thioacetyl, (4-cyano-5-isothiazolyl)thioacetyl, (4-cyano-2-methyl-3-oxo-2,3-dihydroisothiazol-5-yl)thioacetyl, pyridiniumacetyl or quinoliniumacetyl.

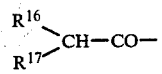

(ii)

The symbol $R^{16}$ means the above-mentioned substituents ($S^1$), and use is often made of particularly a $C_{5-6}$ cycloalkenyl group, $C_{6-10}$ aryl* group, $C_{6-10}$ aryl*oxy group, $C_{1-6}$ alkyl*thio group, $C_{2-6}$ alkenyl*thio group, $C_{6-10}$ aryl*thio group, cyclic amino group, cyano group, heterocyclic* group, heterocycle*thio group, heterocycle*carboxamido group or quaternary ammonium* group for example. The symbol $R^{17}$ means the above-mentioned substituents, especially preferable being hydroxyl group, mercapto group, amino group, amino group substituted with amino acid residue, hydrazino group, azido group, ureido* group, acyl+oxy group, acyl+amino group, carboxyl group, substituted oxycarbonyl group, sulfo group, sulfamoyl group, carbamoyl group or heterocycle* carboxamido group, for example. Among them, those wherein the substituent $R^{17}$ is amino (i.e.

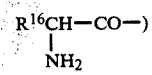

are sometimes especially classified as "amino acid residue". The acyl group

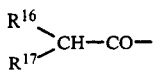

is exemplified by 2-amino-2-(1,4-cyclohexadienyl)acetyl, mandelyl, α-azidophenylacetyl, α-carboxyphenylacetyl, α-(phenoxycarbonyl)phenylacetyl, α-(o-hydroxyphenyl)oxycarbonylphenylacetyl, α-(p-tolyloxycarbonyl)phenylacetyl, α-sulfophenylacetyl, α-sulfo-p-hydroxyphenylacetyl, α-ureidophenylacetyl, α-(Nγ-sulfoureido)phenylacetyl, α-carboxy-p-hydroxyphenylacetyl, α-(formyloxy)phenylacetyl, α-(2-amino-3-carboxypropionamido)phenylacetyl, α-(3-amino-3-carboxypropionamido)phenylacetyl, α-(3,4-dihydroxybenzamido)phenylacetyl, α-(5-carboxy-4-imidazolylcarboxamido)phenylacetyl, α-(1,3-dimethyl-4-pyrazolylcarboxamido)phenylacetyl, 5-phenyl-3-isoxazolylcarboxamido)phenylacetyl, α-[1-(p-methoxyphenyl)-4-chloro-1,2,3-triazol-5-ylcarboxamido]phenylacetyl, α-(4-oxo-1,4-dihydropyridin-3-ylcarboxamido)phenylacetyl, α-[2-oxo-5-(3,4-dihydroxyphenyl)-1,2-dihydropyridin-3-ylcarboxamido]phenylacetyl, α-(4-oxo-4H-1-thiopyran-3-ylcarboxamido)phenylactyl, α-(4-hydroxy-1,5-naphthylidin-3-ylcarboxamido)phenylacetyl, α-(4-ethyl-2,3-dioxopiperazinocarboxamido)phenylacetyl, α-(4-ethyl-2,3-dioxopiperazinocarboxamido)-p-hydroxyphenylacetyl, α-(4-ethyl-2,3-dioxopiperazinocarboxamido)-p-benzyloxyphenylacetyl, α-(4-ethyl-2,3-dioxopiperazinocarboxamido)-p-sulfophenylacetyl, α(4-ethyl-2,3-dioxopiperazinocarboxamido)-p-methoxyphenylacetyl, α-(2-oxoimidazolidinocarboxamido)phenylacetyl, α-(2-oxo-3-methanesulfonylimidazolidinocarboxamido)phenylacetyl, α-(6,7-dihydroxy-4-oxo-4H-benzopyran-3-yl-carboxamido)phenylacetyl, α-(6,7-dihydroxy-2-oxo-2H-benzopyran-3-ylcarboxamido)phenylacetyl, α-hydroxy-2-thienylacetyl, α-hydroxy-3-thienylacetyl, α-carboxy-3-thienylacetyl, α-amino-α-(2-aminothiazol-4-yl)acetyl, α-formamido-α-(2-aminothiazol-4-yl)acetyl, α-acetamido-α-(2-aminothiazol-4-yl)acetyl, α-formamido-α-(2-amino-5-chlorothiazol-4-yl)acetyl, α-acetamido-α-(2-amino-5-chlorothiazol-4-yl)acetyl, α-formamido-α-(5-amino-1,2,4-thiadiazol-3-yl)acetyl, α-acetamido-α-(5-amino-1,2,4-thiadiazol-3-yl)acetyl, α-hydrazino-α-(2-aminothiazol-4-yl)acetyl, α-hydroxy-α-(2-aminothiazol-4-yl)acetyl, α-ureido-α-(2-aminothiazol-4-yl)acetyl, α-[Nγ-(m-hydroxyphenyl)ureido]phenylacetyl, α-[Nγ-(2-methyl-6-hydroxypyrimidin-5-yl)ureido]phenylacetyl, α-[Nγ-(3,4-diacetoxybenzoyl)ureido]phenylacetyl, α-[Nγ-(3,4-dihydroxycinnamoyl)ureido]phenylacetyl, α-[Nγ-(3,4-diacetoxybenzamidoacetyl)ureido]phenylacetyl, α-[Nγ-(2-furylcarbonyl)ureido]phenylacetyl, α-[Nγ-(6,7-dihydro-4-oxo-4H-benzopyran-3-ylcarbonyl)ureido]phenylacetyl, α-(2-chlorovinylthio)phenylacetyl, α-carbamoyl-α-(2-chlorovinylthio)acetyl, α-(4-ethyl-2,3-dioxopiperazinocarboxamido)-α-(2-chlorovinylthio)acetyl, α,α-bis(4-ethyl-2,3-dioxo-1-piperazinocarboxamido)acetyl, α-(2-amino-4-thiazolyl)-α-(4-ethyl-2,3-dioxo-1-piperazinocarboxamido)acetyl, α-(4-hydroxy-6-methylnicotinamide)-α-phenylacetyl, α-(4-hydroxy-6-methylnicotinamide)-α-(4-hydroxyphenyl)acetyl, α-[5,8-dihydro-2-(4-formyl-1-piperazinyl)-5-oxopyrido[2,3-d]pyrimidine-6-carboxamido]-α-phenylacetyl, α-(3,5-dioxo-1,2,4-triazine-6-carboxamido)-α-(4-hydroxyphenyl)acetyl, α-(3-furfurylideneamino-2-oxoimidazolidine-1-carboxamido)-α-phenylacetyl, α-(coumarine-3-carboxamido)-α-phenylacetyl, α-(4-hydroxy-7-methyl-1,8-naphthylidine-3-carboxamido)-α-phenylacetyl, α-(4-hydroxy-7-trifluoromethylquinoline-3-carboxamido)-α-phenylacetyl, N-[2-(2-amino-4-thiazolyl)acetyl]-D-phenylglycyl, α-(6-bromo-1-ethyl-1,4-dihydro-4-oxothieno[2,3-b]pyridine-3-carboxamido)-α-phenylacetyl, α-(4-ethyl-2,3-dioxo-1-piperazinocarboxamido)-α-thienylacetyl, α-(4-n-pentyl-2,3-dioxo-1-piperazinocarboxamido-α-thienylacetyl, α-(4-n-octyl-2,3-dioxo-1-piperazinocarboxamido)-α-thienylacetyl, α-(4-cyclohexyl-2,3-dioxo-1-piperazinocarboxamido)-α-thienylacetyl, α-[4-(2-phenylethyl)-2,3-dioxo-1-piperazinocarboxamido]-α-thienylacetyl or α-(3-furfurylideneamino-2-oxoimidazolidine-1-carboxamido)-α-(4-hydroxyphenyl)acetyl. And the amino acid residue

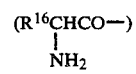

is also here exemplified by alanyl, valyl, leucyl, isoleucyl, seryl, threonyl, cysteinyl, cystinyl, methionyl, aspartyl, glutamyl, lysyl, arginyl, phenylglycyl, phenylalanyl, tyrosyl, histidyl, tryptophanyl or prolyl. The amino group of these amino acid residues may be protected with an amino-protecting group as mentioned below. The amino-protected amino acid residue is exemplified by N-benzyloxycarbonylalanyl or N-benzyloxycarboxamidophenylglycyl. The amino group of the amino acid residue may be further substituted with another amino acid residue. Such acyl group is the residue of dipeptide, as exemplified by phenylglycyl-alanyl, benzyl Nα-benzyloxycarbonyl-γ-glutamylalanyl, alanyl-phenylglycyl, γ-aspartyl-phenylglycyl or γ-glutamyl-alanyl. The amino group of the amino acid residue may be substituted with cyclic carbamoyl group. Such acyl group is exemplified by N-(4-ethyl-2,3-dioxo-1-piperazinocarbonyl)alanyl, N-(4-ethyl-2,3-dithioxo-1-piperazinocarbonyl)phenylglycyl or N-(4-ethyl-2,3-dioxo-1-piperazinocarbonyl)threonyl. As one of the acyl groups

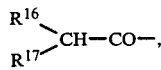

an acyl group representable by

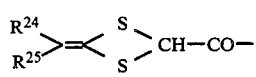

wherein $R^{24}$ and $R^{25}$ are the same or different and stand for hydrogen atom, halogen atom (fluorine, chlorine, bromine and iodine), hydroxymethyl group, difluoromethyl group, trifluoromethyl group, formyl group, cyano group, azido group, carboxyl group, carbamoyl group, $C_{1-6}$ alkylthio group or $C_{6-10}$ aryl*thio group is used as well, which is exemplified by

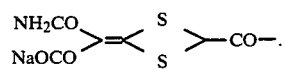

-continued

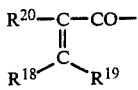 (iii)

The symbol $R^{20}$ means above-mentioned substituents ($S^1$), and use is often made particularly of $C_{6-10}$ aryl* group, $C_{6-10}$ aryl*oxy group, $C_{6-10}$ aryl*thio group, heterocyclic* group or heterocycle*thio group, for example. The symbol $R^{18}$ stands for hydrogen atom or halogen atom (fluorine, chlorine, bromine and iodine), preferably chlorine. The symbol $R^{19}$ stands for $C_{1-6}$ alkyl group, $C_{6-10}$ aryl* group, $C_{1-6}$ alkylthio group, halogen atom, cyano group, amino group, $C_{1-6}$ alkylsulfonyl group, $C_{6-10}$ aryl*sulfonyl group, carbamoyl group, $C_{1-6}$ alkoxyimidoyl group or heterocyclic* group. The $C_{1-6}$ alkoxy group of the $C_{1-6}$ alkoxyimidoyl group is preferably the above-mentioned $C_{1-6}$ alkoxy group, hence the $C_{1-6}$ alkoxyimidoyl group being exemplified by methoxyimidoyl $$(-C\underset{OCH_3}{\overset{NH}{\diagup\hspace{-0.5em}\diagdown}})$$

or ethoxyimidoyl. Those groups other than the above ones are depicted also here by those mentioned in the foregoing explanation Hence, the acyl group

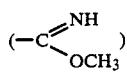

is exemplified by 2-(2-amino-4-thiazolyl)-3-chloroacryloyl, 2-(2-amino-4-thiazolyl)crotonoyl, 2-(2-amino-4-thiazolyl)cinnamoyl, 2-(2-amino-4-thiazolyl)-3-methanesulfonylacryloyl, 2-(2-amino-4-thiazolyl)-3-benzenesulfonylacryloyl, 2-(5-amino-1,2,4-thiadiazol-3-yl)-2-pentenoyl, 2-(5-amino-1,2,4-thiadiazol-3-yl)-3-chloroacryloyl, 2-(5-amino-1,2,4-thiadiazol-3-yl)crotonoyl, 2-(2-amino-5-chloro-4-thiazolyl)-3-chloroacryloyl or 2-(2-amino-5-chloro-4-thiazolyl)crotonoyl.

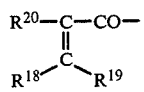 (iv)

The symbol $R^{22}$ means the afore-mentioned substituents ($S^1$), and use is often made of especially $C_{3-10}$ cycloalkyl* group, $C_{5-6}$ cycloalkenyl* group, $C_{6-10}$ aryl* group, $C_{1-6}$ alkoxy group, $C_{6-10}$ aryl*oxy group, $C_{1-6}$ alkyl*thio group, amino $C_{1-6}$ alkylthio group, $C_{6-10}$ aryl*thio group, $C_{7-19}$ aralkyl*thio group, cyano group, acyl+ group, carbamoyl group or heterocyclic* group. Among them, especially preferable are $C_{6-10}$ aryl* group and heterocyclic* group. Substituents of these $C_{6-10}$ aryl group and heterocyclic groups are preferably $C_{1-6}$ alkyl group, hydroxyl group, amino group and halogen atom (fluorine, chlorine, bromine and iodine). Hence, the groups preferably included in the substituent $R^{22}$ are exemplified by phenyl, p-hydroxyphenyl, 2-furyl, 2-thienyl, 4-oxazolyl, 2-amino-4-oxazolyl, 2-amino-5-chloro-4-oxazolyl, 4-thiazolyl, 2-amino-4-thiazolyl, 2-amino-5-chloro-4-thiazolyl, 2-amino-5-bromo-4-thiazolyl, 2-amino-5-fluoro-4-thiazolyl, 2-amino-4-thiazolyl-3-oxide, 2-imino-3-hydroxythiazolin-4-yl, 3-isoxazolyl, 5-amino-3-isoxazolyl, 3-isothiazolyl, 5-amino-3-isothiazolyl, 1,2,4-oxadiazol-3-yl, 5-amino-1,2,4-oxadiazol-3-yl, 1,2,4-thiadiazol-3-yl, 1,2,4-thiadiazol-3-yl, 5-amino-1,2,4-thiadiazol-3-yl, 1,3,4-oxadiazolyl, 2-amino-1,3,4-oxadiazol-5-yl, 1,3,4-thiadiazolyl, 2-amino-1,3,4-thiadiazol-5-yl, 1-($C_{1-6}$ alkyl-5-amino-1,2,4-triazol-3-yl, 4-($C_{1-6}$ alkyl)-5-amino-1,2,4-triazol-3-yl, 1-($C_{1-6}$ alkyl)-2-amino-4-imidazolyl, 2-amino-6-pyridyl, 4-amino-2-pyrimidyl, 2-amino-5-pyrimidyl, 3-pyrazolyl or 4-pyrazolyl. The symbol $R^{21}$ stands for $OR^{23}$ group (wherein $R^{23}$ stands for hydrogen atom or optionally substituted hydrocarbon residue). Here, groups representable by

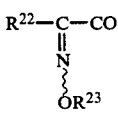

are syn-isomers representable by

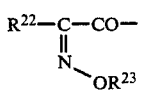

or anti-isomers representable by

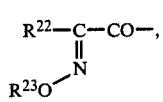, or a mixture thereof.

Among them are preferable those wherein the substituent $R^{22}$ is heterocyclic* group, which are syn-isomers. These acyl groups are shown by the formula;

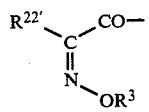

wherein $R^{22'}$ stands for heterocyclic* group and $R^3$ stands for hydrogen atom or optionally substituted hydrocarbon residue. Among them, most preferable ones are those in which the heterocyclic*group $R^{22'}$ is a substituted thiazolyl group or thiadiazolyl group, namely those representable by the formula;

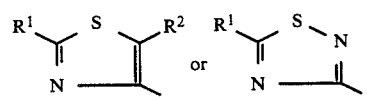

wherein $R^1$ stands for optionally protected amino group and $R^2$ stands for hydrogen atom, halogen atom or nitro group. Hence, most preferable $R^b$ group is representable by the formula;

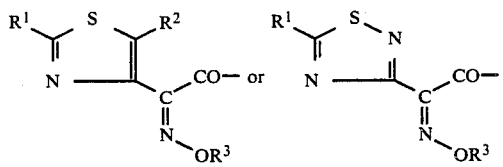

Syn-isomer (Z configuration) Syn-isomer (Z configuration) Accordingly, preferable ones of compound [I] having the acyl group $R^b$ as the substituent $R^o$ are those of the following structure;

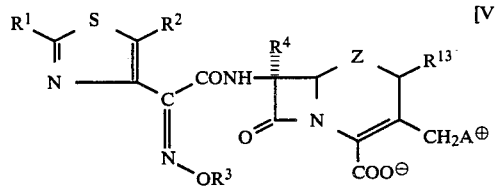   [VII]

or

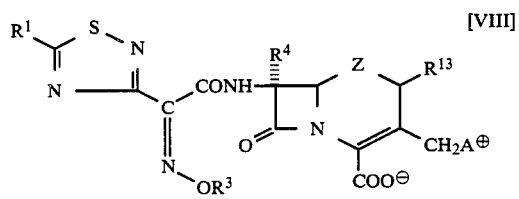   [VIII]

wherein each symbol is as defined above.

Detailed description about the substituents $R^1$, $R^2$ and $R^3$ is as follows.

$R^1$ stands for an optionally protected amino group. In the field of synthesis of β-lactam and peptide, protecting groups of amino group have been extensively studied, and the method of protection has already been established. In the present invention as well, any of those known amino-protecting groups may suitably be employed. As such amino-protecting groups, there may be mentioned for example $C_{1-6}$ alkanoyl* group, $C_{3-5}$ alkenoyl* group, $C_{6-10}$ aryl*carbonyl group, phthaloyl group, heterocycle*carbonyl group, $C_{1-6}$ alkyl*sulfonyl group, camphorsulfonyl group, $C_{6-10}$ aryl*sulfonyl group, substituted oxycarbonyl group, carbamoyl* group, thiocarbamoyl* group, $C_{6-10}$ aryl*methyl group, di-$C_{6-10}$ aryl*methyl group, tri-$C_{6-10}$ aryl*methyl group, $C_{6-10}$ aryl*methylene group, $C_{6-10}$ aryl*thio group, substituted silyl group or 2-$C_{1-10}$ alkoxy-carbonyl-1-methyl-1-ethenyl group.

As "$C_{1-6}$ alkanoyl* group", there may concretely be mentioned here formyl, acetyl, propionyl, butyryl, valeryl, pivaloyl, succinyl, glutaryl, monochloroacetyl, dichloroacetyl, trichloroacetyl, monobromoacetyl, monofluoroacetyl, difluoroacetyl, trifluoroacetyl, monoiodoacetyl, 3-oxobutyryl, 4-chloro-3-oxobutyryl, phenylacetyl, p-chlorophenylacetyl, phenoxyacetyl or p-chlorophenoxyacetyl. As "$C_{3-5}$ alkenoyl* group", there may concretely be mentioned here acryloyl, crotonoyl, maleoyl, cinnamoyl, p-chlorocinnamoyl or β-phenylcinnamoyl.

As "$C_{6-10}$ aryl*carbonyl group", there may be mentioned, for example, benzoyl, naphthoyl, p-toluoyl, p-tert-butylbenzoyl, p-hydroxybenzoyl, p-methoxybenzoyl, p-tert-butoxybenzoyl, p-chlorobenzoyl or p-nitrobenzoyl.

As the heterocycle*carbonyl group, there may be mentioned those as described hereinafter.

As "$C_{1-6}$ alkyl*sulfonyl group", there may be mentioned, for example, methanesulfonyl or ethanesulfonyl.

As "$C_{6-10}$ aryl*sulfonyl group", there may be mentioned here benzenesulfonyl, naphthalenesulfonyl, p-toluenesulfonyl, p-tert-butylbenzenesulfonyl, p-methoxybenzenesulfonyl, p-chlorobenzenesulfonyl or p-nitrobenzenesulfonyl, for example.

"Substituted oxycarbonyl group" means not only the the above-mentioned one, i.e. $C_{1-10}$ alkoxy-carbonyl group, $C_{6-10}$ aryloxy-carbonyl group or $C_{7-19}$ aralkyloxycarbonyl group, but contains here one having a substituent, and therefore there may be mentioned here methoxycarbonyl, ethoxycarbonyl, n-propoxycarbonyl, isopropoxycarbonyl, n-butoxycarbonyl, tert-butoxycarbonyl, cyclohexyloxycarbonyl, norbornyloxycarbonyl, phenoxycarbonyl, naphthyloxycarbonyl, benzyloxycarbonyl, methoxymethyloxycarbonyl, acetylmethyloxycarbonyl, 2-trimethylsilylethoxycarbonyl, 2-methanesulfonylethoxycarbonyl, 2,2,2-trichloroethoxycarbonyl, 2-cyanoethoxycarbonyl, p-methylphenoxycarbonyl, p-methoxyphenoxycarbonyl, p-chlorophenoxycarbonyl, p-methylbenzyloxycarbonyl, p-methoxybenzyloxycarbonyl, p-chlorobenzyloxycarbonyl, p-nitrobenzyloxycarbonyl, benzhydryloxycarbonyl, cyclopropyloxycarbonyl, cyclopentyloxycarbonyl or cyclohexyloxycarbonyl, for example.

"Carbamoyl* group" is exemplified here by carbamoyl, N-methylcarbamoyl, N-ethylcarbamoyl, N,N-dimethylcarbamoyl, N,N-diethylcarbamoyl, N-phenylcarbamoyl, N-acetylcarbamoyl, N-benzoylcarbamoyl or N-(p-methoxyphenyl)carbamoyl.

"Carbamoyl*oxy group" is exemplified here by carbamoyloxy, N-methylcarbamoyloxy, N,N-dimethylcarbamoyloxy, N-ethylcarbamoyloxy or N-phenylcarbamoyloxy.

"Thiocarbamoyl* group" is exemplified here by thiocarbamoyl, N-methylthiocarbamoyl or N-phenylthiocarbamoyl, for example.

"$C_{6-10}$ aryl*methyl group" is exemplified by benzyl, naphthylmethyl, p-methylbenzyl, p-methoxybenzyl, p-chlorobenzyl or p-nitrobenzyl.

"Di-$C_{6-10}$ aryl*methyl group" is exemplified by benzhydryl or di-(p-tolyl)methyl.

"Tri-$C_{6-10}$ aryl*methyl group" is exemplified by trityl or tri-(p-tolyl)methyl.

"$C_{6-10}$ aryl*methylene group" is exemplified by benzylidene, p-methylbenzylidene or p-chlorobenzylidene.

"$C_{6-10}$ aryl*thio group" is exemplified by o-nitrophenylthio.

"Substituted silyl group" means a silyl group, together with the amino group to be protected, representable by the general formula; $R^6R^7R^8SiNH$, $(R^6R^7R^8Si)_2N$ or

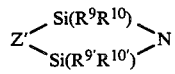

[wherein $R^6$, $R^7$, $R^8$, $R^9$, $R^{10}$, $R^{9'}$ and $R^{10'}$ are the same or different and stand for $C_{1-6}$ alkyl group or $C_{6-10}$ aryl* group, and Z' stands for $C_{1-3}$ alkylene group e.g. methylene, ethylene or propylene], which is exemplified by trimethylsilyl, tert-butyldimethylsilyl or $-Si(CH_3)_2CH_2CH_2Si(CH_3)_2-$.

The $C_{1-10}$ alkoxy-carbonyl group of "2-$C_{1-10}$ alkoxycarbonyl-1-methyl-1-ethenyl group" is preferably one of those as mentioned in the foregoing. Hence, 2-$C_{1-10}$ alkoxycarbonyl-1-methyl-1-ethenyl group is exemplified by 2-methoxycarbonyl-1-methyl-1-ethenyl, 2-ethoxycarbonyl-1-methyl-1-ethenyl, 2-tert-butoxycarbonyl-1-methyl-1-ethenyl, 2-cyclohexyloxycarbonyl-1-methyl-1-ethenyl or 2-norbornyloxycarbonyl-1-methyl-1-ethenyl.

The symbol $R^2$ stands for hydrogen atom, halogen atom or nitro group. As the halogen atom are mentioned here fluorine, chlorine, bromine, etc., preferably chlorine.

The symbol $R^3$ stands for hydrogen atom or a substituted hydrocarbon residue. The hydrocarbon residue may be exemplified by $C_{1-6}$ alkyl group, $C_{2-6}$ alkenyl group, $C_{2-6}$ alkynyl group, $C_{3-10}$ cycloalkyl group or $C_{5-6}$ cycloalkenyl group, especially preferably, $C_{1-3}$ alkyl group or a substituted $C_{1-3}$ alkyl group. The $C_{1-6}$ alkyl group is, also here, preferably one of those described in the foregoing and may be exemplified by methyl, ethyl, n-propyl, isopropyl, n-butyl, isobutyl, sec-butyl, tert-butyl, n-pentyl or n-hexyl, especially preferably, methyl, ethyl and n-propyl. The $C_{2-6}$ alkenyl group is, also here, preferably one of those described in the foregoing and may be exemplified by vinyl, allyl, isopropenyl, methallyl, 1,1-dimethylallyl, 2-butenyl or 3-butenyl. The $C_{2-6}$ alkynyl group may be exemplified by ethynyl, 1-propynyl, 2-propynyl or propargyl. The $C_{3-10}$ cycloalkyl group is, also here, preferably the above-mentioned $C_{3-8}$ cycloalkyl group and may be exemplified by cyclopropyl, cyclobutyl, cyclopentyl, cyclohexyl, cycloheptyl or adamantyl. The $C_{5-6}$ cycloalkenyl group may be exemplified by 2-cyclopentenyl, 3-cyclopentenyl, 2-cyclohexenyl, 3-cyclohexenyl, cyclopentadienyl or cyclohexadienyl. Substituents of these hydrocarbon residues may be exemplified by hydroxyl group, $C_{1-6}$ alkyl group, $C_{2-6}$ alkenyl group, $C_{2-6}$ alkynyl group, $C_{3-10}$ cycloalkyl group, $C_{5-6}$ cycloalkenyl group, $C_{6-10}$ aryl group, $C_{7-19}$ aralkyl group, heterocyclic group, $C_{1-6}$ alkoxy group, $C_{3-10}$ cycloalkyloxy group, $C_{6-10}$ aryloxy group, $C_{7-19}$ aralkyloxy group, heterocycle-oxy group, mercapto group, $C_{1-6}$ alkylthio group, $C_{3-10}$ cycloalkylthio group, $C_{6-10}$ arylthio group, $C_{7-19}$ aralkylthio group, heterocycle-thio group, amino group, mono-$C_{1-6}$ alkylamino group, di-$C_{1-6}$ alkylamino group, tri-$C_{1-6}$ alkylammonium group, $C_{3-10}$ cycloalkylamino group, $C_{6-10}$ arylamino group, $C_{7-19}$ aralkylamino group, heterocycle-amino group, cyclic amino group, azido group, nitro group, halogen atom, cyano group, carboxyl group, $C_{1-10}$ alkoxycarbonyl group, $C_{6-10}$ aryloxy-carbonyl group, $C_{7-19}$ aralkyloxy-carbonyl group, $C_{6-10}$ aryl-acyl+ group, $C_{1-6}$ alkanoyl group, $C_{3-5}$ alkenoyl group, $C_{6-10}$ aryl-acyl+oxy group, $C_{2-6}$ alkanoyloxy group, $C_{3-5}$ alkenoyloxy group, carbamoyl* group, thiocarbamoyl* group, carbamoyl*oxy group, phthalimido group, $C_{1-6}$ alkanoylamino group, $C_{6-10}$ aryl-acyl+amino group, carboxyamino group, $C_{1-10}$ alkoxy-carboxamido group, $C_{6-10}$ aryloxy-carboxamido group or $C_{7-19}$ aralkyloxy-carboxamido group, and two or more of them, same or different, may be present. As substituents of the hydrocarbon residues, more specifically stating, the $C_{1-6}$ alkyl group stands for the above-mentioned groups, i.e. methyl, ethyl, n-propyl, isopropyl, n-butyl, isobutyl, sec-butyl, tert-butyl, n-pentyl or n-hexyl, the $C_{2-6}$ alkenyl group stands for the above-mentioned groups, i.e. vinyl, allyl, isopropenyl, methallyl, 1,1-dimethylallyl, 2-butenyl or 3-butenyl, the $C_{2-6}$ alkynyl group stands for the above-mentioned groups, i.e. ethynyl, 1-propynyl, 2-propynyl or propargyl, the $C_{3-10}$ cycloalkyl group stands for the above-mentioned groups, i.e. cyclopropyl, cyclobutyl, cyclopentyl, cyclohexyl, cycloheptyl or adamantyl, the $C_{5-6}$ cycloalkenyl group stands for the above-mentioned groups, i.e. cyclopropenyl, 2-cyclopentenyl, 3-cyclopentenyl, 2-cyclohexenyl, 3-cyclohexenyl, cyclopentadienyl or cyclohexadienyl, the $C_{6-10}$ aryl group stands for the above-mentioned groups, i.e. phenyl, naphthyl or biphenylyl, the $C_{7-19}$ aralkyl group stands for the above-mentioned groups, i.e. benzyl, 1-phenylethyl, 2-phenylethyl, phenylpropyl, naphthylmethyl or benzhydryl, the $C_{1-16}$ alkoxy group stands for the above-mentioned groups, i.e. methoxy, ethoxy, n-propoxy, isopropoxy, n-butoxy, tert-butoxy, n-pentyloxy or n-hexyloxy, the $C_{3-10}$ cycloalkyloxy group stands for the above-mentioned groups, i.e. cyclopropyloxy or cyclohexyloxy, the $C_{6-10}$ aryloxy group stands for the above-mentioned groups, i.e. phenoxy or naphthyloxy, the $C_{7-19}$ aralkyloxy group stands for the above-mentioned groups, i.e. benzyloxy, 1-phenylethyloxy, 2-phenylethyloxy or benzhydryloxy, the $C_{1-6}$ alkylthio group stands for the above-mentioned groups, i.e. methylthio, ethylthio, n-propylthio or n-butylthio, the $C_{3-10}$ cycloalkylthio group stands for the above-mentioned groups, i.e. cyclopropylthio or cyclohexylthio, the $C_{6-10}$ arylthio group stands for the above-mentioned groups, i.e. phenylthio or naphthylthio, the $C_{7-19}$ aralkylthio group stands for the above-mentioned groups, i.e. benzylthio, phenylethylthio or benzhydrylthio, the mono-$C_{1-6}$ alkylamino group stands for the above-mentioned groups, i.e. methylamino, ethylamino, n-propylamino, or n-butylamino, the di-$C_{1-6}$ alkylamino group stands for the above-mentioned groups, i.e. dimethylamino, diethylamino, methylethylamino, di-(n-propyl)amino or di-(n-butyl)amino, the tri-$C_{1-6}$ alkylammonium group stands for the above-mentioned groups, i.e. trimethylammonium or triethylammonium, the $C_{3-10}$ cycloalkylamino group stands for the above-mentioned groups, i.e. cyclopropylamino, cyclopentylamino or cyclohexylamino, the $C_{6-10}$ arylamino group stands for the above-mentioned groups, i.e. anilino or N-methylanilino, the $C_{7-19}$ aralkylamino group stands for the above-mentioned groups, i.e. benzylamino, 1-phenylethylamino, 2-phenylethylamino or benzhydrylamino, the cyclic amino group stands for the above-mentioned groups, i.e. pyrrolidino, piperidino, piperazino, morpholino or 1-pyrrolyl, the halogen atom stands for here fluorine, chlorine, bromine or iodine, the $C_{1-10}$ alkoxy-carbonyl group stands for the above-mentioned groups, i.e. methoxycarbonyl, ethoxycarbonyl, n-propoxycarbonyl, isopropoxycarbonyl, n-butoxycarbonyl, isobutoxycarbonyl, tert-butoxycarbonyl, cyclopentyloxycarbonyl, cyclohexyloxycarbonyl or norbornyloxycarbonyl, the $C_{6-10}$ aryloxy-carbonyl group stands for the above-mentioned groups, i.e. phenoxycarbonyl or naphthyloxycarbonyl, the $C_{7-19}$ aralkyloxycarbonyl group stands for the above-mentioned groups, i.e. benzyloxycarbonyl or benzhydryloxycarbonyl, the $C_{6-10}$ aryl-acyl+ group stands for the above-mentioned groups, i.e. benzoyl, naphthoyl, phthaloyl or phenylacetyl, the $C_{1-6}$ alkanoyl group stands for the above-mentioned groups, i.e. formyl acetyl, propionyl, butyryl, valeryl, pivaloyl, succinyl or glutaryl, the $C_{3-5}$ alkenoyl group stands for the above-mentioned groups, i.e. acryloyl, crotonoyl or maleoyl, the $C_{6-10}$ aryl-acyl+oxy group stands for the above-mentioned groups, i.e. benzoyloxy, naphthoyloxy or phenylacetoxy, the $C_{2-6}$ alkanoyloxy group stands for the above-mentioned groups, i.e. acetoxy, propionyloxy, butyryloxy, valeryloxy or pivaloyloxy, the $C_{3-5}$ alkenoyloxy group stands for the above-mentioned groups, i.e. acryloyloxy or crotonoyloxy, the carbamoyl* group stands for the above-mentioned groups, i.e. carbamoyl, N-methylcarbamoyl, N,N-dimethylcarbamoyl, N-ethylcarbamoyl, N,N-diethylcarbamoyl, N-phenylcarbamoyl, N-acetylcarbamoyl, N-benzoylcarbamoyl, N-(p-methoxyphenyl)carbamoyl and, in addition, pyrrolidinocarbonyl, piperidinocarbonyl, piperazinocarbonyl or morpholinocarbonyl, the thiocarbamoyl* group stands for the above-mentioned groups, i.e. thiocarbamoyl, N-methylthiocarbamoyl or N-phenylthiocarbonyl, the carbamoyl*oxy group stands for the above-mentioned group, i.e. carbamoyloxy, N-methylcarbamoyloxy, N,N-dimethylcarbamoyloxy, N-ethylcarbamoyloxy or N-phenylcarbamoyloxy, "$C_{1-6}$ alkanoylamino group" stands for e.g. acetamido, propionamido, butyramido, valeramido or pivalamido, "$C_{6-10}$ aryl-acyl+amino group" stands for e.g. benzamido, naphthoylamino or phthalimido, "$C_{1-10}$ alkoxy-carboxamido group" stands for e.g. methoxycarboxamido ($CH_3OCONH-$), ethoxycarboxamido or tert-butoxycarboxamido, "$C_{6-10}$ aryloxy-carboxamido group" stands for e.g. phenoxycarboxamido ($C_6H_5OCONH-$), and "$C_{7-19}$ aralkyloxy-carboxamido group" stands for e.g. benzyloxycarboxamido ($C_6H_5CH_2OCONH-$) or benzhydryloxycarboxamido. The heterocyclic group, heterocyclic groups of heterocycle-oxy group, heterocycle-thio group and heterocycle-amino group are also here such groups as formed by removing one hydrogen atom bonding to the carbon atom of the heterocyclic ring. Such a heterocyclic ring as above may be exemplified by a 5- to 8-membered ring containing one to several, preferably 1–4, hetero atoms such as oxygen atom or sulfur atom. Such heterocyclic groups may be exemplified also here by those concretely mentioned above, including 2-pyrrolyl, as they are. Hence, "heterocycle-oxy group" is exemplified by thiazolyloxy, and "heterocycle-thio group" is exemplified by thiazolylthio, and "heterocycle-amino group" is exemplified by thiazolylamino or thiadiazolylamino. Preferable substituted hydrocarbon residues are $C_{1-3}$ alkyl groups ($C_{1-3}$ alkyl group means methyl, ethyl, n-propyl, isopropyl, etc.) substituted with e.g. hydroxyl group, cycloalkyl group, alkoxy group, alkylthio group, amino group, trialkylammonium group, halogen atom, carboxyl group, alkoxycarbonyl group, carbamoyl group, cyano group, azido group or heterocyclic group, which may concretely be mentioned, among many others, cyclopropylmethyl, methoxymethyl, ethoxymethyl, 1-methoxyethyl, 2-methoxyethyl, 1-ethoxyethyl, 2-hydroxyethyl, methylthiomethyl, 2-aminoethyl, 2-(trimethylammonium)ethyl, 2-(triethylammonium)ethyl, fluoromethyl, difluoromethyl, trifluoromethyl, 2-fluoroethyl, 2,2-difluoroethyl, chloromethyl, 2-chloroethyl, 2,2-dichloroethyl, 2,2,2-trichloroethyl, 2-bromoethyl, 2-iodoethyl, 2,2,2-trifluoroethyl, carboxymethyl, 1-carboxyethyl, 2-carboxyethyl, 2-carboxypropyl, 3-carboxypropyl, 1-carboxybutyl, cyanomethyl, 1-carboxy-1-methylethyl, methoxycarbonylmethyl, ethoxycarbonylmethyl, tert-butoxycarbonylmethyl, 1-methoxycarbonyl-1-methylethyl, 1-ethoxycarbonyl-1-methylethyl, 1-tert-butoxycarbonyl-1-methylethyl, 1-benzyloxycarbonyl-1-methylethyl, 1-pivaloyloxycarbonyl-1-methylethyl, carbamoylmethyl, 2-azidoethyl, 2-(pyrazolyl)ethyl, 2-(imidazolyl)ethyl, 2-(2-oxopyrrolidin-3-yl)ethyl or 2-amino-4-thiazolylmethyl. Most preferable ones among the above-exemplified hydrocarbon residues are straight-chain $C_{1-3}$ alkyl groups, e.g. methyl, ethyl and n-propyl; straight-chain or branched $C_{1-3}$ alkyl groups substituted with halogen atom, hydroxyl group, alkoxy group, carboxyl group, alkoxycarbonyl group or cyano group, e.g. 2-fluoroethyl, 2-chloroethyl, 2-hydroxyethyl, 2-methoxyethyl, cyanomethyl, carboxymethyl, tert-butoxycarbonylmethyl, 1-carboxy-1-methylethyl or 1-tert-butoxycarbonyl-1-methylethyl; allyl group and propargyl group. If the symbol $R^{3'}$ represents a preferable hydrocarbon residue exemplified above or hydrogen atom, the compounds [I] of this invention having as $R^0$ an acyl group of

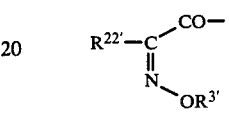

wherein $R^{22'}$ stands for a heterocyclic* group possess strong antibacterial activity, and, especially against resistant-bacteria, show excellent bactericidal action. As mentioned in the foregoing, compounds whose heterocyclic* group $R^{22'}$ is shown by the formula

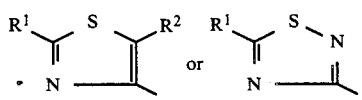

wherein $R^1$ stands for an optionally protected amino group and $R^2$ stands for hydrogen atom, halogen atom or nitro group are most preferable. Hence, especially preferable compounds [I] are those having the following structural formula.

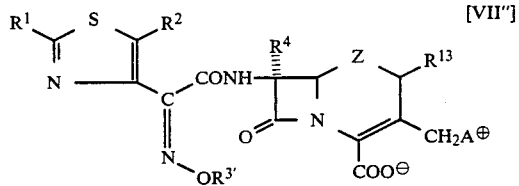  [VII"]

or

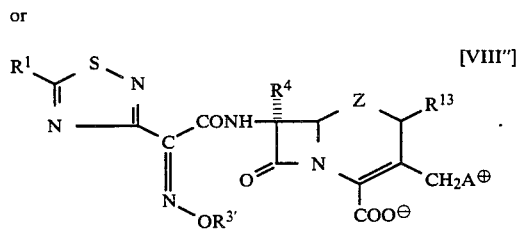  [VIII"]

wherein symbols are of the same meaning as defined above.

Preferable examples of the acyl group shown by

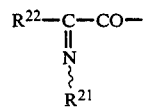

are 2-(2-aminothiazol-4-yl)-2(Z)-(hydroxyimino)acetyl, 2-(2-aminothiazol-4-yl)-2(Z)-(methoxyimino)acetyl, 2-(2-chloroacetamidothiazol-4-yl)-2(Z)-(methoxyimino)acetyl, 2-(2-aminothiazol-4-yl)-2(Z)-(ethoxyimino)acetyl, 2-(2-aminothiazol-4-yl)-2(Z)-(n-propoxyimino)acetyl, 2-(2-aminothiazol-4-yl)-2(Z)-(isopropoxyimino)acetyl, 2-(2-aminothiazol-4-yl)-2(Z)-(n-butoxyimino)acetyl, 2-(2-aminothiazol-4-yl)-2(Z)-(n-hexyloxyimino)acetyl, 2-(2-aminothiazol-4-yl)-2(Z)-(cyclopropylmethyloxyimino)acetyl, 2-(2-aminothiazol-4-yl)-2(Z)-(benzyloxyimino)acetyl, 2-(2-aminothiazol-4-yl)-2(Z)-(allyloxyimino)acetyl, 2-(2-aminothiazol-4-yl)-2(Z)-(propargyloxyimino)acetyl, 2-(2-aminothiazol-4-yl)-2(Z)-(methoxymethyloxyimino)acetyl, 2-(2-aminothiazol-4-yl)-2(Z)-(ethoxymethyloxyimino)acetyl, 2-(2-aminothiazol-4-yl)-2(Z)-[(1-methoxyethyl)oxyimino]acetyl, 2-(2-aminothiazol-4-yl)-2(Z)-[(2-methoxyethyl)oxyimino]acetyl, 2-(2-aminothiazol-4-yl)-2(Z)-[(2-ethoxyethyl)oxyimino]acetyl, 2-(2-aminothiazol-4-yl)-2(Z)-[(1-ethoxyethyl)oxyimino]acetyl, 2-(2-aminothiazol-4-yl)-2(Z)-[(2-hydroxyethyl)oxyimino]acetyl, 2-(2-aminothiazol-4-yl)-2(Z)-(methylthiomethyloxyimino)acetyl, 2-(2-aminothiazol-4-yl)-2(Z)-[(2-aminoethyl)oxyimino]acetyl, 2-(2-aminothiazol-4-yl)-2(Z)-(fluoromethyloxyimino)acetyl, 2-(2-aminothiazol-4-yl)-2(Z)-(difluoromethyloxyimino)acetyl, 2-(2-aminothiazol-4-yl)-2(Z)-(trifluoromethyloxyimino)acetyl, 2-(2-aminothiazol-4-yl)-2(Z)-[(2-fluoroethyl)oxyimino]acetyl, 2-(2-aminothiazol-4-yl)-2(Z)-[(2,2-difluoroethyl)oxyimino]acetyl, 2-(2-aminothiazol-4-yl)-2(Z)-(chloromethyloxyimino)acetyl, 2-(2-aminothiazol-4-yl)-2(Z)-[(2-chloroethyl)oxyimino]acetyl, 2-(2-aminothiazol-4-yl)-2(Z)-[(2,2-dichloroethyl)oxyimino]acetyl, 2-(2-aminothiazol-4-yl)-2(Z)-[(2,2,2-trichloroethyl)oxyimino]acetyl, 2-(2-aminothiazol-4-yl)-2(Z)-[(2-bromoethyl)oxyimino]acetyl, 2-(2-aminothiazol-4-yl)-2(Z)-[(2-iodoethyl)oxyimino]acetyl, 2-(2-aminothiazol-4-yl)-2(Z)-[(2,2,2-trifluoroethyl)oxyimino]acetyl, 2-(2-aminothiazol-4-yl)-2(Z)-(carboxymethyloxyimino)acetyl, 2-(2-aminothiazol-4-yl)-2(Z)-(1-carboxyethyloxyimino)acetyl, 2-(2-aminothiazol-4-yl)-2(Z)-[(2-carboxyethyl)oxyimino]acetyl, 2-(2-aminothiazol-4-yl)-2(Z)-(1-carboxypropyloxyimino)acetyl, 2-(2-aminothiazol-4-yl)-2(Z)-[(3-carboxypropyl)oxyimino]acetyl, 2-(2-aminothiazol-4-yl)-2(Z)-[(1-carboxybutyl)oxyimino]acetyl, 2-(2-aminothiazol-4-yl)-2(Z)-(cyanomethyloxyimino)acetyl, 2-(2-aminothiazol-4-yl)-2(Z)-[(1-carboxy-1-methylethyl)oxyimino]acetyl, 2-(2-aminothiazol-4-yl)-2(Z)-(methoxycarbonylmethyloxyimino)acetyl, 2-(2-aminothiazol-4-yl)-2(Z)-(ethoxycarbonylmethyloxyimino)acetyl, 2-(2-aminothiazol-4-yl)-2(Z)-[(tert-butoxycarbonylmethyl)oxyimino]acetyl, 2-(2-aminothiazol-4-yl)-2(Z)-[1-(tert-butoxycarbonyl)ethoxyimino]acetyl, 2-(2-aminothiazol-4-yl)-2(Z)-[(1-methoxycarbonyl-1-methylethyl)oxyimino]acetyl, 2-(2-aminothiazol-4-yl)-2(Z)-[(1-ethoxycarbonyl-1-methylethyl)oxyimino]acetyl, 2-(2-aminothiazol-4-yl)-2(Z)-[(1-tert-butoxycarbonyl-1-methylethyl)oxyimino]acetyl, 2-(2-aminothiazol-4-yl)-2(Z)-[1-(tert-butoxycarbonyl)propoxyimino]acetyl, 2-(2-aminothiazol-4-yl)-2(Z)-[(1-benzyloxycarbonyl-1-methylethyl)oxyimino]acetyl, 2-(2-aminothiazol-4-yl)-2(Z)-[(1-pivaloyloxycarbonyl-1-methylethyl)oxyimino]acetyl, 2-(2-aminothiazol-4-yl)-2(Z)-(carbamoylmethyloxyimino)acetyl, 2-(2-aminothiazol-4-yl)-2(Z)-[1-(1-carbamoyl-1-methyl)ethyloxyimino]acetyl, 2-(2-aminothiazol-4-yl)-2(Z)-(2-azidoethyloxyimino)acetyl, 2-(2-aminothiazol-4-yl)-2(Z)-(phenoxycarbonyloxyimino)acetyl, 2-(2-amino-5-chlorothiazol-4-yl)-2(Z)-(hydroxyimino)acetyl, 2-(2-amino-5-chlorothiazol-4-yl)-2(Z)-(methoxyimino)acetyl, 2-(2-amino-5-chlorothiazol-4-yl)-2(Z)-(ethoxyimino)acetyl, 2-(2-amino-5-chlorothiazol-4-yl)-2(Z)-(n-propoxyimino)acetyl, 2-(2-amino-5-chlorothiazol-4-yl)-2(Z)-[(2-fluoroethyl)oxyimino]acetyl, 2-(2-amino-5-chlorothiazol-4-yl)-2(Z)-[(2-chloroethyl)oxyimino]acetyl, 2-(2-amino-5-chlorothiazol-4-yl)-2(Z)-(carboxymethyloxyimino)acetyl, 2-(2-amino-5-chlorothiazol-4-yl)-2(Z)-[(tert-butoxycarbonylmethyl)oxyimino]acetyl, 2-(2-amino-5-chlorothiazol-4-yl)-2(Z)-[(1-carboxy-1-methylethyl)oxyimino]acetyl, 2-(2-amino-5-chlorothiazol-4-yl)-2(Z)-[(1-tert-butoxycarbonyl-1-methylethyl)oxyimino]acetyl, 2-(2-amino-5-bromothiazol-4-yl)-2(Z)-(ethoxyimino)acetyl, 2-(5-amino-1,2,4-thiadiazol-3-yl)-2(Z)-(hydroxyimino)acetyl, 2-(5-amino-1,2,4-thiadiazol-3-yl)-2(Z)-(methoxyimino)acetyl, 2-(5-amino-1,2,4-thiadiazol-3-yl)-2(Z)-(ethoxyimino)acetyl, 2-(5-amino-1,2,4-thiadiazol-3-yl)-2(Z)-(ethoxyimino)acetyl, 2-(5-amino-1,2,4-thiadiazol-3-yl)-2(Z)-[(2-fluoroethyl)oxyimino]acetyl, 2-(5-amino-1,2,4-thiadiazol-3-yl)-2(Z)-[(2-chloroethyl)oxyimino]acetyl, 2-(5-amino-1,2,4-thiadiazol-3-yl)-2(Z)-(carboxymethyloxyimino)acetyl, 2-(5-amino-1,2,4-thiadiazol-3-yl)-2(Z)-[(1-carboxy-1-methylethyl)oxyimino]acetyl, 2-(5-amino-1,2,4-thiadiazol-3-yl)-2(Z)-[(1-tert-butoxycarbonyl-1-methylethyl)oxyimino]acetyl, 2-(5-aminoisoxazol-3-yl)-2(Z)-(ethoxyimino)acetyl, 2-(5-amino-1,2,4-oxadiazol-3-yl)-2(Z)-(ethoxyimino)acetyl, 2-(2-imino-3-hydroxythiazolin-4-yl)-2(Z)-(ethoxyimino)acetyl, 2-(2-amino-3-oxidothiazol-4-yl)-2(Z)-(ethoxyimino)acetyl, 2-thienyl-2(Z)-(methoxyimino)acetyl, 2-thienyl-2(Z)-(ethoxyimino)acetyl, 2-furyl-2(Z)-(methoxyimino)acetyl, 2-furyl-2(Z)-(ethoxyimino)acetyl, 2-(1,3,4-thiadiazolyl)-2(Z)-(ethoxyimino)acetyl, 2-(p-hydroxyphenyl)-2(Z)-(ethoxyimino)acetyl, 2-phenyl-2(Z)-(ethoxyimino)acetyl, 2-phenyl-2(Z)-(hydroxyimino)acetyl, 2-[p-(γ-D-glutamyloxy)phenyl]-2(Z)-(hydroxyimino)acetyl or 2-[p-(3-amino-3-carboxypropoxy)phenyl]-2(Z)-(hydroxyimino)acetyl.

The $C_{1-6}$ alkanoyl* group described as one of the acyl groups ($R^b$) includes, besides the above-mentioned $C_{1-6}$ alkanoyl group, heterocycle*-CO—CO—, $R^{15}CH_2CO$—,

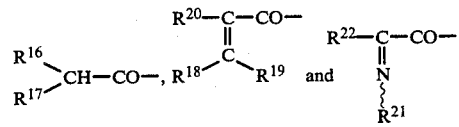

trifluoroacetyl, 4-carboxybutyl, 5-amino-5-carboxyvaleryl, 5-oxo-5-carboxyvaleryl, N-[2-(2-amino-4-thiazolyl)-2(Z)-(methoxyimino)acetyl]-D-alanyl, N-[2-(2-amino-4-thiazolyl-2(Z)-(methoxyimino)acetyl]-D-phenylglycyl or 2-(2-amino-4-thiazolyl)-2-[2-(2-amino-4-thiazolyl)-2(Z)-(methoxyimino)acetamido]acetyl.

The $C_{3-5}$ alkenoyl* groups as acyl groups ($R^b$) other than $C_{1-6}$ alkanoyl* groups, may be mentioned also here the afore-mentioned acryloyl, crotonoyl, maleoyl, cinnamoyl, p-chlorocinnamoyl or β-phenylcinnamoyl; the $C_{3-10}$ cycloalkyl-carbonyl groups may be mentioned also here the afore-mentioned cyclopropylcarbonyl, cyclobutylcarbonyl, cyclopentylcarbonyl, cyclohexylcarbonyl, cycloheptylcarbonyl or adamantylcarbonyl; $C_{5-6}$ cycloalkenyl-carbonyl groups may be mentioned also here the afore-mentioned cyclopentenylcarbonyl, cyclopentadienylcarbonyl, cyclohexenylcarbonyl or cyclohexadienylcarbonyl; $C_{6-10}$ aryl*carbonyl group may be mentioned also here benzoyl, naphthoyl, p-toluoyl, p-tert-butylbenzoyl, p-hydroxybenzoyl, p-methoxybenzoyl, p-tert-butoxybenzoyl, p-chlorobenzoyl or p-nitrobenzoyl; and "heterocycle*carbonyl group" is exemplified by 2- or 3-pyrrolylcarbonyl, 3-, 4- or 5-pyrazolylcarbonyl, 2-, 4- or 5-imidazolylcarbonyl, 1,2,3- or 1,2,4-triazolylcarbonyl, 1H- or 2H-tetrazolylcarbonyl, 2- or 3-furylcarbonyl, 2- or 3-thienylcarbonyl, 2-, 4- or 5-oxazolylcarbonyl, 3-, 4- or 5-isoxazolylcarbonyl, 1,2,3-oxadiazol-4- or 5-ylcarbonyl, 1,2,4-oxadiazol-3- or 5-ylcarbonyl, 1,2,5- or 1,3,4-oxadiazolylcarbonyl, 2-, 4- or 5-thiazolylcarbonyl, 2-amino-4-thiazolylcarbonyl, 3-, 4- or 5-isothiazolylcarbonyl, 1,2,3-thiadiazol-4- or 5-ylcarbonyl, 1,2,4-thiadiazol-3- or 5-ylcarbonyl, 5-amino-1,2,4-thiadiazol-3-ylcarbonyl, 1,2,5- or 1,3,4-thiadiazolylcarbonyl, 2- or 3-pyrrolidinylcarbonyl, 2-, 3- or 4-pyridylcarbonyl, 2-, 3- or 4-pyridylcarbonyl-N-oxide, 3- or 4-pyridazinylcarbonyl, 3- or 4-pyridazinylcarbonyl-N-oxide, 2-, 4- or 5-pyrimidinylcarbonyl, 2-, 4- or 5-pyrimidinylcarbonyl-N-oxide, 2-pyrazinylcarbonyl, 2-, 3- or 4-piperidinylcarbonyl, piperazinylcarbonyl, 3H-indol-2- or 3-ylcarbonyl, 2-, 3- or 4-pyranylcarbonyl, 2-, 3- or 4-thiopyranylcarbonyl, benzopyranylcarbonyl, quinolylcarbonyl, pyrido[2,3-d]pyrimidylcarbonyl, 1,5-, 1,6-, 1,7-, 1,8-, 2,6- or 2,7-naphthylidylcarbonyl, thieno[2,3-b]pyridylcarbonyl, pyrimidopyridylcarbonyl, pyrazinoquinolylcarbonyl, or 3-(2,6-dichlorophenyl)-5-methylisoxazol-4-ylcarbonyl.

As the amino-protecting groups (hereinafter sometimes denoted as the symbol $R^c$) included in the substituents $R^o$, those listed before as amino-protecting groups of optionally protected amino groups shown by $R^1$ can also be applied here, and oxycarbonyl groups mentioned therein are more favorable. Hence, the aforementioned methoxycarbonyl, ethoxycarbonyl, n-propoxycarbonyl, isopropoxycarbonyl, n-butoxycarbonyl, tert-butoxycarbonyl, cyclohexylcarbonyl, norbornyloxycarbonyl, phenoxycarbonyl, naphthyloxycarbonyl, benzyloxycarbonyl, methoxymethyloxycarbonyl, acetylmethyloxycarbonyl, 2-trimethylsilylethoxycarbonyl, 2-methanesulfonylethoxycarbonyl, 2,2,2-trichloroethoxycarbonyl, 2-cyanoethoxycarbonyl, p-methylphenoxycarbonyl, p-methoxyphenoxycarbonyl, p-chlorophenoxycarbonyl, p-methylbenzyloxycarbonyl, p-methoxybenzyloxycarbonyl, p-chlorobenzyloxycarbonyl, p-nitrobenzyloxycarbonyl, benzhydryloxycarbonyl, cyclopropyloxycarbonyl, cyclopentyloxycarbonyl or cyclohexyloxycarbonyl can favorably be mentioned here also.

The substituent $R^4$ in the compounds [I] of this invention stands for hydrogen atom, methoxy group or formamido group (HCONH—).

The substituent $R^{13}$ in the compounds [I] of this invention stands for hydrogen atom, methyl group, hydroxyl group or halogen atom. The halogen atom means here fluorine, chlorine, bromine or iodine.

In the compounds [I] of this invention, the substituent A stands for pyrazol-2-yl group which has another ring fused at the 1,5-position. The fused ring means the pyrazole ring having a 5- to 6-membered aromatic heterocyclic ring fused therewith, and it may optionally be further fused with another aromatic ring or aromatic heterocyclic ring. The mark $\oplus$ attached to the right shoulder of the substituent A means that A has a monovalent positive electric charge. The optionally substituted pyrazol-2-yl group ($A^\oplus$) forming the fused ring at 1,5-position is shown by the general formula;

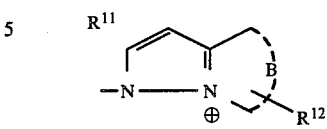

wherein B stands for a group forming a 5- to 6-membered aromatic heterocyclic ring which may be fused with another aromatic ring or aromatic heterocyclic ring, $R^{11}$ stands for hydrogen atom or a substituent (or substituents) on the pyrazole ring and $R^{12}$ stands for hydrogen atom or a substituent (or substituents) on the ring which may be fused with the pyrazole ring. B consists of one or more carbon atoms, nitrogen atoms, oxygen atoms and/or sulfur atoms, and, among them, the carbon atom combines with one hydrogen atom or one substituent, or forms another fused ring together with the adjacent carbon atom. The pyrazol-2-yl group may be embodied as follows, for example;

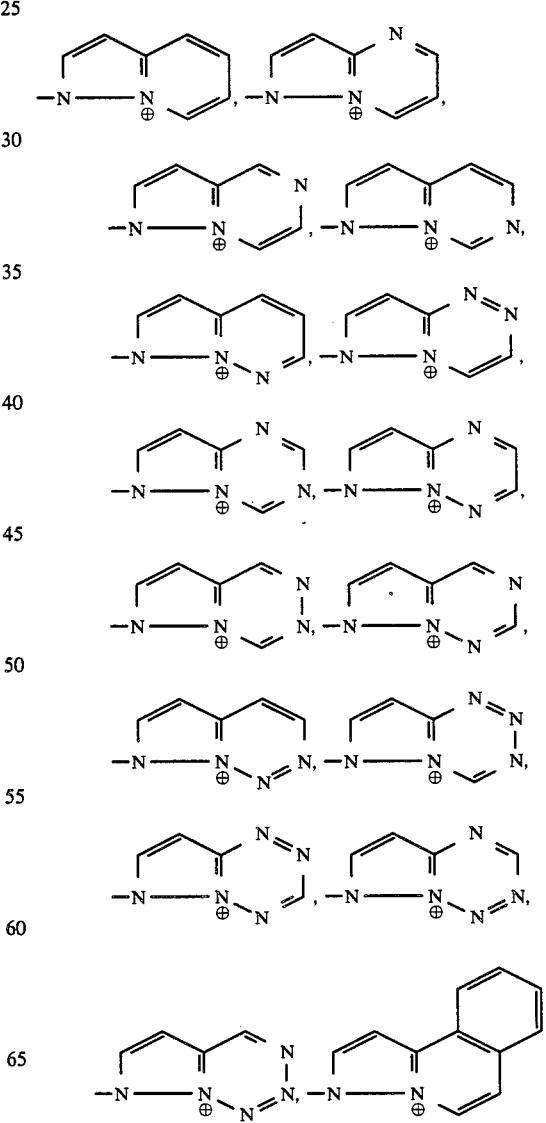

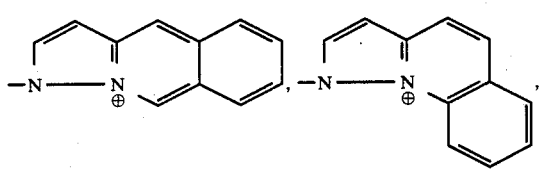

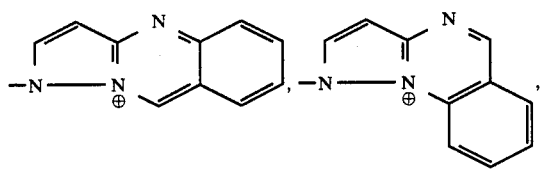

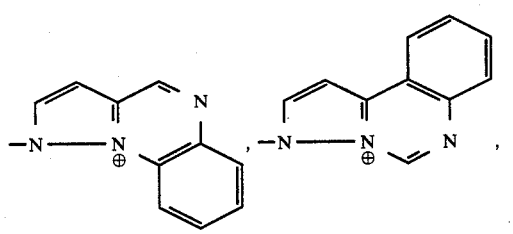
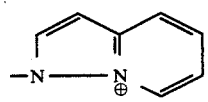

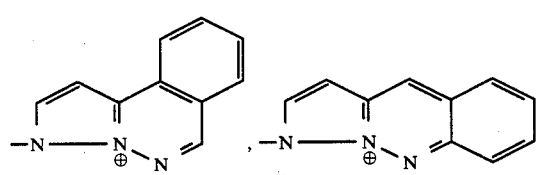
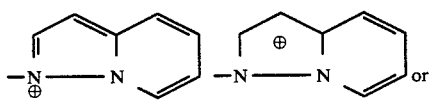
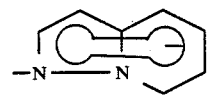

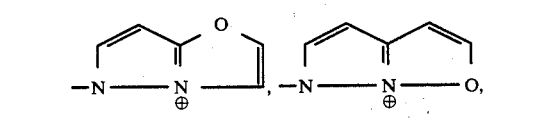

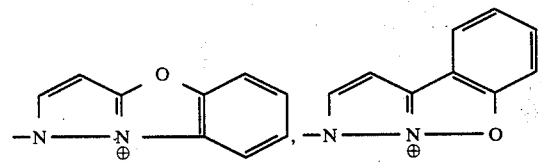

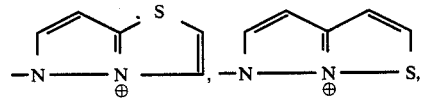

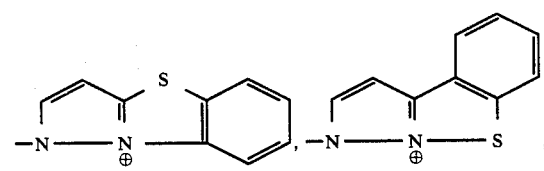

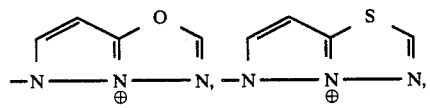

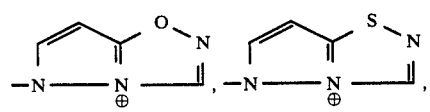

In the above pyrazol-2-yl groups as well as groups embodied as above, the positive electric charge $A^{\oplus}$ is applied, for convenience sake, to the nitrogen atom at the 1-position of pyrazol, but there may be a case where the said quaternary nitrogen is that of the nitrogen atom at the 2-position. Further, there may be cases where the monovalent positive electric charge is delocalized at the pyrazole ring, or even delocalized on the entire fused ring. Therefore, the above may include The position which this positive electric charge takes varies with, among others, the state (solid or in solution) of the compound [I], kinds of solvents, pH, temperature or kinds of substituents. Accordingly, the present invention includes all the cases where the positive electric charge is localized at a nitrogen atom or is delocalized on the entire fused ring. The substituents $R^{11}$ and $R^{12}$ on the fused ring A may be exemplified by a hydroxyl group, hydroxy $C_{1-6}$ alkyl group, $C_{1-6}$ alkyl group, $C_{2-6}$ alkenyl group, $C_{2-6}$ alkynyl group, $C_{4-6}$ alkadienyl group, $C_{3-10}$ cycloalkyl group, $C_{5-6}$ cycloalkenyl group, $C_{3-10}$ cycloalkyl $C_{1-6}$ alkyl group, $C_{6-10}$ aryl group, $C_{7-12}$ aralkyl group, di-$C_{6-10}$ arylmethyl group, tri-$C_{6-10}$ arylmethyl group, heterocyclic group, $C_{1-6}$ alkoxy group, $C_{1-6}$ alkoxy $C_{1-6}$ alkyl group, $C_{3-10}$ cycloalkyloxy group, $C_{6-10}$ aryloxy group, $C_{7-19}$ aralkyloxy group, mercapto group, mercapto $C_{1-6}$ alkyl group, sulfo group, sulfo $C_{1-6}$ alkyl group, $C_{1-6}$ alkylthio group, $C_{1-6}$ alkylthio $C_{1-6}$ alkyl group, $C_{3-10}$ cycloalkylthio group, $C_{6-10}$ arylthio group, $C_{7-19}$ aralkylthio group, amino group, amino $C_{1-6}$ alkyl group, mono-$C_{1-6}$ alkylamino group, di-$C_{1-6}$ alkylamino group, mono-$C_{1-6}$ alkylamino $C_{1-6}$ alkyl group, di-$C_{1-6}$ alkylamino $C_{1-6}$ alkyl group, $C_{3-10}$ cycloalkylamino group, $C_{6-10}$ arylamino group, $C_{7-19}$ aralkylamino group, cyclic amino group, cyclic amino $C_{1-6}$ alkyl group, cyclic amino $C_{1-6}$ alkylamino group, azido group, nitro group, halogen atom, halogeno $C_{1-6}$ alkyl group, cyano group, cyano $C_{1-6}$ alkyl group, carboxyl group, carboxy $C_{1-6}$ alkyl group, $C_{1-10}$ alkoxy-carbonyl group, $C_{1-10}$ alkoxy-carbonyl $C_{1-6}$ alkyl group, $C_{6-10}$ aryloxycarbonyl group, $C_{7-19}$ aralkyloxy-carbonyl group, $C_{6-10}$ aryl-acyl$^+$ group, $C_{1-6}$ alkanoyl group, $C_{2-6}$ alkanoyl $C_{1-6}$ alkyl group, $C_{3-5}$ alkenoyl group, $C_{6-10}$ arylacyl$^+$oxy group, $C_{2-6}$ alkanoyloxy group, $C_{2-6}$ alkanoyloxy $C_{1-6}$ alkyl group, $C_{3-5}$ alkenoyloxy group, carbamoyl $C_{1-6}$ alkyl group, carbamoyl* group, thiocarbamoyl* group, carbamoyl-*oxy group, carbamoyloxy $C_{1-6}$ alkyl group, $C_{1-6}$ alkanoylamino group, $C_{6-10}$ aryl-acyl+amino group, sulfonamido group, carboxyamino group, $C_{1-10}$ alkoxycarboxamido group, $C_{6-10}$ aryloxy-carboxamido group or $C_{7-19}$ aralkyloxy-carboxamido group. Among the above-mentioned substituents, "$C_{4-6}$ alkadienyl group" is exemplified by 1,3-butadienyl, "$C_{3-10}$ cycloalkyl $C_{1-6}$ alkyl group" is exemplified by cyclopentylmethyl or cyclohexylmethyl, and halogen atom means here fluorine, chlorine or bromine. All the groups other than the above may be exemplified as in the foregoing.

These substituents may occur singly or in plurality with the same or different ones. The number of the substituent(s) is favorably 0 to 2 in $R^{11}$ and 0 to 3 in $R^{12}$. In addition, the 3,4-position or pyrazole ring may be fused with an alicyclic ring, aromatic ring or heterocyclic ring. As examples, the following may be counted:

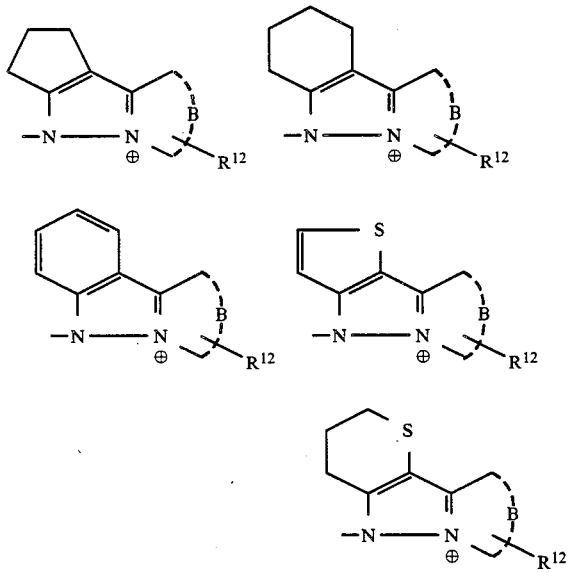

In the above, B and $R^{12}$ are of the same significance as afore-defined. The above-mentioned $R^{11}$ and $R^{12}$ may be further substituted.

In the above compound [I], the mark ⊖ attached to the right shoulder of the carboxyl substituent (—COO) means that the said carboxyl group is a carboxylate anion and forms an internal salt by making a pair with the positive electric charge on the substituent A. On the other hand, the compound [I] may be physiologically or pharmaceutically acceptable salts or esters. As the physiologically or pharmaceutically acceptable salts, there may be mentioned, among others, inorganic base salts, ammonium salt, organic base salts, inorganic acid addition salts, organic acid addition salts and basic amino acid salts. These may be exemplified by an alkali metal (e.g. sodium, potassium, etc.) or an alkaline earth metal (e.g. calcium) as an inorganic base capable of giving the inorganic base salts; procaine, 2-phenylethylbenzylamine, dibenzylethylenediamine, ethanolamine, diethanolamine, tris-hydroxymethylaminomethane, poly-hydroxyalkylamine or N-methylglucosamine as an organic base capable of giving the organic base salts; hydrochloric acid, hydrobromic acid, sulfuric acid, nitric acid or phosphoric acid as an inorganic acid capable of giving the inorganic acid addition salts; p-toluenesulfonic acid, methanesulfonic acid, formic acid, trifluoroacetic acid or maleic acid as an organic acid capable of giving the organic acid addition salts; and lysine, arginine, ornithine or histidine as a basic amino acid capable of giving the basic amino acid salts.

Among these salts, basic salts (i.e. inorganic base salts, ammonium salt, organic base salts and basic amino acid salts) mean salts derivable in case there is (are) acidic group(s) e.g. carboxyl group, sulfo group etc. on the substituent $R^o$ or A of the compound [I], and acid addition salts (i.e. inorganic acid addition salts and organic acid addition salts) mean salts derivable in case there is(are) basic group(s) e.g. amino group, monoalkylamino group, dialkylamino group, cycloalkylamino group, arylamino group, aralkylamino group, cyclic amino group, nitrogen-containing heterocyclic group etc. on the substituent $R^o$ or A of the compound [I]. Additionally, the acid addition salt also includes an intramolecular salt of the compound [I], i.e. a salt having carboxyl(COOH) group at the 4-position and $CH_2A^{\oplus}.M^{\ominus}$ group wherein $M^{\ominus}$ denotes an anion formed by removal of a proton ($H^{\oplus}$) from inorganic acid or organic acid; such an anion is exemplified by chloride ion, bromide ion, sulfate ion, p-toluenesulfonate ion, methanesulfonate ion, trifluoroacetate ion at the 3-position, which is formed through addition of one mole of acid to carboxylate($COO^{\ominus}$) group of the 4-position and $CH_2A^{\oplus}$ group of the 3-position of the compound [I]. The ester derivatives of the compound [I] mean esters derivable by esterifying the carboxyl group contained in the molecule, which include esters usable as synthetic intermediates and bioavailably unstable non-toxic esters. The esters usable as synthetic intermediates are exemplified by $C_{1-6}$ alkyl* ester, $C_{2-6}$ alkenyl ester, $C_{3-10}$ cycloalkyl ester, $C_{3-10}$ cycloalkyl $C_{1-6}$ alkyl ester, $C_{6-10}$ aryl* ester, $C_{7-12}$ aralkyl* ester, di-$C_{6-10}$ arylmethyl ester, tri-$C_{6-10}$ aryl-methyl ester or substituted silyl ester. There may be exemplified, as "$C_{1-6}$ alkyl* group" capable of giving $C_{1-6}$ alkyl* ester, methyl, ethyl, n-propyl, isopropyl, n-butyl, isobutyl, sec-butyl, tert-butyl, n-pentyl, n-hexyl, benzyloxymethyl, 2-methylsulfonylethyl, 2-trimethylsilylethyl, 2,2,2-trichloroethyl, 2-iodoethyl, acetylmethyl, p-nitrobenzoylmethyl, p-mesylbenzoylmethyl, phthalimidomethyl, succinimidomethyl, benzenesulfonylmethyl, phenylthiomethyl, dimethylaminoethyl, pyridine-1-oxido-2-methyl, methylsulfinylmethyl, or 2-cyano-1,1-dimethylethyl; as $C_{2-6}$ alkenyl group capable of giving $C_{2-6}$ alkenyl ester, the afore-mentioned ones, i.e. vinyl, allyl, 1-propenyl, isopropenyl, 1-butenyl, 2-butenyl, 3-butenyl, methallyl, 1,1-dimethylallyl or 3-methyl-3-butenyl; as $C_{3-10}$ cycloalkyl group capable of giving $C_{3-10}$ cycloalkyl ester, the afore-mentioned ones, i.e. cyclopropyl, cyclobutyl, cyclopentyl, cyclohexyl, cycloheptyl, norbornyl or adamantyl; as $C_{3-10}$ cycloalkyl $C_{1-6}$ alkyl group capable of giving $C_{3-10}$ cycloalkyl $C_{1-6}$ alkyl ester, the afore-mentioned ones, i.e. cyclopropylmethyl, cyclopentylmethyl or cyclohexylmethyl; as "$C_{6-10}$ aryl* group" capable of giving $C_{6-10}$ aryl* ester, phenyl, α-naphthyl, β-naphthyl, biphenylyl, p-nitrophenyl or p-chlorophenyl; as "$C_{7-12}$ aralkyl* group" capable of giving $C_{7-12}$ aralkyl* ester, benzyl, 1-phenylethyl, 2-phenylethyl, phenylpropyl, naphthylmethyl, p-nitrobenzyl, p-methoxybenzyl, 1-indanyl, phenacyl or 3,5-di-tert-butyl-4-hydroxybenzyl; as di-$C_{6-10}$ aryl-methyl group capable of giving di-$C_{6-10}$ arylmethyl ester, the afore-mentioned ones, i.e. benzhydryl or bis(p-methoxyphenyl)methyl; as tri-$C_{6-10}$ aryl-methyl group capable of giving tri-$C_{6-10}$ aryl-methyl ester, the afore-mentioned ones, i.e. trityl; and as substituted silyl group capable of giving substituted silyl ester, the afore-mentioned ones, i.e. trimethylsilyl, tert-butyldimethylsilyl or $—Si(CH_3)_2CH_2CH_2Si(CH_3)_2—$. The above esters include esters at the 4-position. Such compound having above ester group at the 4-position forms an intramolecular salt of $CH_2A^{\oplus}.M^{\ominus}$ wherein $M^{\ominus}$ has the same meaning as defined above at the 3-position.

As the bioavailably unstable and non-toxic esters, those which have been confirmed as employable in the fields of penicillin and cephalosporin can conveniently be employed also in the present invention, which may be exemplified by $C_{2-6}$ alkanoyloxy $C_{1-6}$ alkyl ester, 1-($C_{1-6}$ alkoxy)$C_{1-6}$ alkyl ester or 1-($C_{1-6}$ alkylthio)$C_{1-6}$ alkyl ester. The $C_{2-6}$ alkanoyloxy $C_{1-6}$ alkyl ester is exemplified by acetoxymethyl ester, 1-acetoxyethyl ester, 1-acetoxybutyl ester, 2-acetoxyethyl ester, propionyloxymethyl ester, pivaloyloxymethyl ester. The 1-($C_{1-6}$ alkoxy)$C_{1-6}$ alkyl ester is exemplified by methoxymethyl ester, ethoxymethyl ester, isopropoxymethyl ester, 1-methoxyethyl ester or 1-ethoxyethyl ester. The 1-($C_{1-6}$ alkylthio)$C_{1-6}$ alkyl ester is exemplified by methylthiomethyl ester or ethylthiomethyl ester. The present invention includes, besides the above-mentioned ester derivatives, physiologically or pharmaceutically acceptable compounds which are convertible in vivo to the compound [I]. The above-mentioned esters usable as synthetic intermediates and bioavailably unstable non-toxic esters include esters at the 4-position. Such esters at the 4-position usually form an intramolecular salt of $CH_2A^{\oplus}.M^{\ominus}$ wherein $M^{\ominus}$ has the same meaning as defined above at the 3-position.

When a compound [I] has a hydroxyl group, the hydroxyl group may be protected. Groups usable for protecting hydroxyl group include those which are usually employed for protecting hydroxyl group in the field of β-lactam and organic chemistry, which may be exemplified by, besides the afore-mentioned $C_{2-6}$ alkanoyl groups, substituted oxycarbonyl group, tert-butyl group, $C_{7-12}$ aralkyl* group, di-$C_{6-10}$ aryl-methyl group, tri-$C_{6-10}$ aryl-methyl group, 1-($C_{1-6}$ alkoxy)$C_{1-6}$ alkyl group, 1-($C_{1-6}$ alkylthio)$C_{1-6}$ alkyl group and substituted silyl group, acetal residues e.g. 2-tetrahydropyranyl or 4-methoxy-4-tetrahydropyranyl.

When a compound [I] additionally has an amino group other than those mentioned above, the amino group may also be protected. Groups employable for protecting those amino groups are exemplified also here by those referred to in the protection of the afore-mentioned amino groups.

Among the compounds [I] of this invention, one in which the substituent $R^o$ is nitrogen-containing heterocyclic group ($R^a$) or acyl group ($R^b$) has a broad antibacterial spectrum and can be used for prophylaxis and therapy of various diseases of men and animals caused by pathogenic bacteria, for example, infections of respiratory tract or of urinary passages. Characteristic features of the antibacterial spectrum of the antibacterial compound [I] ($R^o=R^a$ or $R^b$) are mentioned as follows:

(1) remarkably strong activity against a variety of gram-negative bacteria;
(2) strong activity against gram-positive bacteria (e.g. *Staphylococcus aureus* or *Corynebacterium diphtheriae*);
(3) remarkably effective against *Pseudomonas aeruginosa* which are not sensitive to therapy with conventional cephalosporin-type antibiotics; and
(4) Strong activity against a variety of β-lactamase-producing gram-negative bacteria (e.g. the genera Escherichia, Enterobacter, Serratia or Proteus).

Especially against bacteria belonging to the genus Pseudomonas, to which aminoglycoside antibiotics such as Amikacin or Gentamicin have been used, the antibacterial compound [I] shows antibacterial activity comparable to these aminoglycosides with remarkably lower toxicity to men and animals, which is counted as one of the great advantages.

Besides, the antibacterial compound [I] ($R^o=R^a$ or $R^b$) of this invention has the following characteristic features, i.e. excellent stability, high concentration in blood, long duration of effect and remarkably high concentration is tissue.

How to make the compound [I] of this invention, its salts or esters will be described in detail as follows. A compound [I] or its salt or ester can be produced by a conventional method or an analogous one thereto.

PRODUCTION METHOD (1)

Synthesis of Compound [II] ([I], $R^0$=hydrogen atom)

For example, 7-amino compound [II] ([I], $R^0$=hydrogen atom) can be synthesized by allowing a compound representable by the general formula;

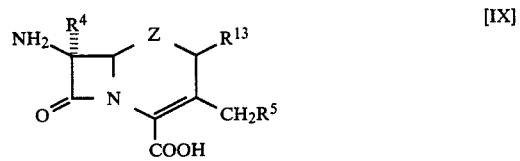

[IX]

wherein the symbol $R^5$ stands for hydroxyl group, acyloxy group, carbamoyloxy group, substituted carbamoyloxy or halogen atom, and other symbols are of respectively the same meanings as defined above or a salt or ester thereof to react with a pyrazole compound representable by the general formula A' wherein A' means optionally substituted pyrazole forming a fused ring at 1,5-position or a salt thereof.

The reaction scheme is as follows:

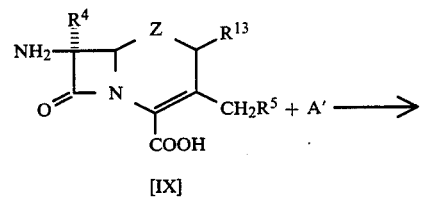

[IX]

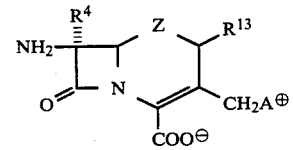

[II]([I], $R^0$ = hydrogen) atom wherein Z, $R^4$, $R^{13}$, $R^5$ and A are of the same meaning as defined above.

The starting compound [IX] or a salt or ester thereof is a compound which can be easily produced by a conventional method or an analogous one thereto. As salts and esters of the compound [IX] can be also mentioned here the same described hereafter as those of the compound [II].

As the acyloxy group representable by the symbol $R^5$, the above-mentioned acyl+oxy group can be employed also here, especially preferable being acetoxy, chloroacetoxy, propionyloxy, butyryloxy, pivaloyloxy, 3-oxobutyryloxy, 4-chloro-3-oxobutyryloxy, 3-carboxypropionyloxy, 4-carboxybutyryloxy, 3-ethoxycarbamoylpropionyloxy, benzoyloxy, o-carboxybenzoyloxy, o-(ethoxycarbonylcarbamoyl)benzoyloxy and o-(ethoxycarbonylsulfamoyl)benzoyloxy. As the substituted carbamoyloxy group representable by the symbol $R^5$, the above-mentioned ones can be employed also here, especially preferable being methylcarbamoyloxy and N,N-dimethylcarbamoyloxy. Halogen atoms representable by the symbol $R^5$ are preferably chlorine, bromine and iodine. As to the pyrazole compound A' and its salts, detailed description will be given hereafter.

Even in case where the amino group at the 7-position is protected, the above reaction proceeds likewise. When necessary, the protecting group may be removed after the reaction to thereby give a 7-amino compound [II] ([I], $R^0$=hydrogen atom).

PRODUCTION METHOD (2)

Synthesis of Compound [$I^a$] ($R^0 = R^a$; $R^a$ denotes nitrogen-containing heterocyclic group)

For example, (2-1): By allowing the 7-amino compound [II] obtained in the preceding section (1) or a salt or ester thereof (description about the salt and ester will be made hereafter) to react with a compound representable by the general formula $R^a$Hal wherein $R^a$ stands for a nitrogen-containing heterocyclic group and Hal stands for a halogen atom e.g. fluorine, chlorine, bromine or iodine or its salt, a compound [$I^a$] ($R^0 = R^a$) can be synthesized.

The reaction scheme is as follows:

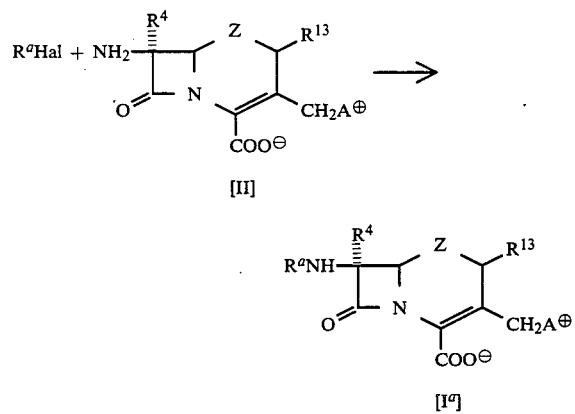

wherein the symbol $R^a$ stands for nitrogen containing heterocyclic group, and Z, $R^4$, $R^{13}$, A and Hal are of the same meaning as defined above.

As the halogen atom (Hal) of the compound $R^a$Hal, use is most often made of fluorine. As salts of the compound $R^a$Hal are exemplified inorganic acid addition salts such as hydrochloride, hydrobromide, sulfate, nitrate or phosphate, or organic acid addition salts such as formate, acetate, trifluoroacetate, methanesulfonate or p-toluenesulfonate. The reaction is generally conducted by mixing a compound $R^a$Hal or its salt with a 7-amino compound [II] or a salt or ester thereof in water or an aqueous solvent at room temperature (about 15°–30° C.). For preventing hydrolysis of the compound $R^a$Hal prior to its reaction with the 7-amino compound [II], it is necessary to control the pH of the reaction solution. Optimal pH ranges from 6 to 8.5. For the purpose of eliminating from the reaction system hydrogen halogenide formed during the reaction, use may be made of a deacidifying agent, for example, inorganic bases such as sodium carbonate, potassium carbonate, calcium carbonate or sodium hydrogen carbonate; tertiary amines such as triethylamine, tri-(n-propyl)amine, tri-(n-butyl)amine, diisopropylethylamine, cyclohexyldimethylamine, pyridine, lutidine, γ-collidine, N,N-dimethylaniline, N-methylpiperidine, N-methylpyrrolidine or N-methylmorpholine; or alkylene oxides such as propylene oxide or epichlorohydrin. For preventing the pH to shift to alkaline side too far, an inorganic acid such as hydrochloric acid, hydrobromic acid, sulfuric acid, nitric acid or phosphoric acid may sometimes be employed. When an aqueous solvent is employed, the organic solvent to be mixed with water may be exemplified by dimethylsulfoxide, sulfolane, or hexamethyl phosphoramide, besides ethers such as dioxane, tetrahydrofuran, diethyl ether, tert-butyl methyl ether or diisopropyl ether, amides such as formamide, N,N-dimethylformamide or N,N-dimethylacetamide and ketones such as acetone, methyl ethyl ketone or methyl isobutyl ketone. The amount of the compound $R^a$Hal is usually 1–3 mol., preferably 1–2 mol., relative to 1 mol. of the 7-amino compound [II]. While the reaction time varies with kinds of 7-amino compound [II] and the compound $R^a$Hal, kinds of the solvent employed and reaction temperatures, it usually ranges from one minute to 48 hours, preferably from 15 minutes to 3 hours.

The compound $R^a$Hal and its salt can be easily produced by a conventional method or an analogous one thereto.

According to the method mentioned above, compounds having the following general formula can be synthesized, for example.

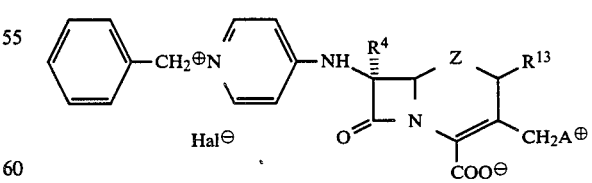

When the compound $R^a$Hal is too reactive and liable to be hydrolyzed, the reaction may be conducted in e.g. anhydrous dimethylsulfoxide in the presence of an organic base e.g. anhydrous triethylamine. According to this method, compounds of the following general formula can be synthesized, for example.

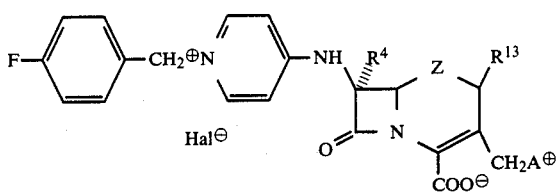

The above reaction is sometimes conducted in the presence of an organic acid e.g. p-toluenesulfonic acid, methanesulfonic acid, ethanesulfonic acid, acetic acid or butyric acid, or an inorganic acid e.g. hydrochloric acid, sulfuric acid or carbonic acid. In this case also, as the halogen atom (Hal) of $R^a$Hal, fluorine is most frequently employed. The reaction is usually conducted in a solvent such as dimethylformamide, tetrahydrofuran, dioxane, chloroform, methanol, acetonitrile, benzene, acetone or water, or an optional mixture thereof. The reaction temperature ranges from 0° C. to 150° C., preferably 20° C. to 80° C. The reaction time usually ranges from 30 minutes to 20 hours. According to this method, compounds of the following general formula can be synthesized, for example.

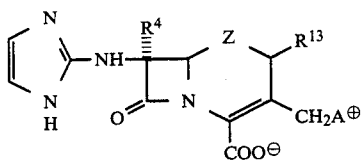

(2-2): After allowing the starting compound [IX] employed in the preceding section(1) or a salt or ester thereof to react with the compound $R^a$Hal or a salt thereof, pyrazole compound A' wherein A' is of the same meaning as defined above is further allowed to react with the reaction product to synthesize a corresponding compound [$I^a$] ($R^0=R^a$). The reaction is shown by the following scheme:

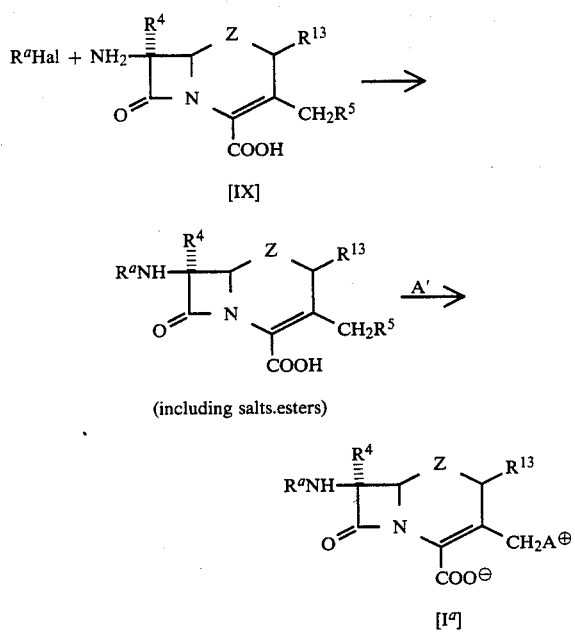

wherein the symbol $R^a$ stands for nitrogen-containing heterocyclic group, and the symbols Z, $R^4$, $R^{13}$, $R^5$, A and Hal are of the same meaning as defined above.

The starting compound [IX], its salts and esters, and the compound $R^a$Hal and its salts can be exemplified also here by those mentioned in the foregoing. About the pyrazole compound A' and its salts, detailed description will be given later. The reactions of Production Method (2-1) and (1) can be applied as they are.

PRODUCTION METHOD (3)

Synthesis of compound [$I^b$] ($R^0=R^b$; $R^b$ denotes acyl group)

For example.

(3-1): By allowing the 7-amino compound [II] obtained in the section (1) or a salt or ester thereof to react with a carboxylic acid representable by the general formula $R^b$OH wherein $R^b$ denotes acyl group or a salt or reactive derivative thereof, a compound [$I^b$] ($R^0=R^b$) can be synthesized. The reaction is shown by the following scheme:

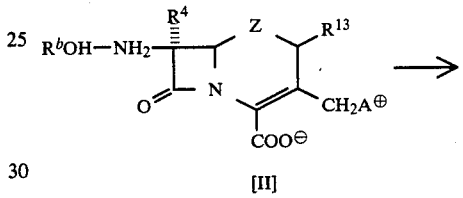

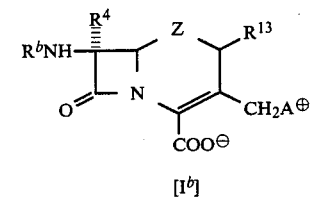

wherein the symbol $R^b$ stands for acyl group, and the symbols Z, $R^4$, $R^{13}$, and A are of the same meaning as defined above.

This is a method of subjecting a 7-amino compound [II] to acylation with carboxylic acid $R^b$OH or a salt or reactive derivative thereof. In this method, the carboxylic acid $R^b$OH in the free form, a salt or reactive derivative thereof is used as the acylating agent of the 7-amino group of the 7-amino compound [II]. More concretely, the free acid $R^b$OH or a reactive derivative of the free acid $R^b$OH, such as inorganic salt, organic salt, acid halide, acid azide, acid anhydride, mixed acid anhydride, active amide, active ester or active thioester is used for the acylation. There may be mentioned, among others, as inorganic salts, alkali metal salts (e.g. sodium salt, potassium salt, etc.) or alkaline earth metal salts (e.g. calcium salt, etc.); as organic salts, trimethylamine salt, triethylamine salt, tert-butyldimethylamine salt, dibenzylmethylamine salt, benzyldimethylamine salt, N,N-dimethylaniline salt, pyridine salt or quinoline salt; as acid halide, acid chloride or acid bromide; as mixed acid anhydride, mono-$C_{1-6}$ alkyl carbonic acid mixed anhydride (e.g. mixed acid anhydride of the free acid $R^b$OH with, for example, monomethyl carbonic acid, monoethyl carbonic acid, monoisopropyl carbonic acid, monoisobutyl carbonic acid, mono-tert-butyl carbonic acid, monobenzyl carbonic acid, mono(p-nitrobenzyl)-carbonic acid, or monoallyl carbonic acid), $C_{1-6}$ aliphatic carboxylic acid mixed anhydride (e.g. mixed acid anhydride of the free acid R$^b$OH with, for example, acetic acid, trichloroacetic acid, cyanoacetic acid, propionic acid, butyric acid, isobutyric acid, valeric acid, isovaleric acid, pivalic acid, trifluoroacetic acid, trichloroacetic acid or acetoacetic acid), C$_{7-12}$ aromatic carboxylic acid mixed anhydride (e.g. mixed acid anhydride of the free acid R$^b$OH with, for example, benzoic acid, p-toluic acid or p-chlorobenzoic acid), organic sulfonic acid mixed anhydride (e.g. mixed acid anhydride of the free acid R$^b$OH with, for example, methanesulfonic acid, ethanesulfonic acid, benzenesulfonic acid or p-toluenesulfonic acid); as active amide, an amide with a nitrogen-containing heterocyclic compound (e.g. acid amide of the free acid R$^b$OH with, for example, pyrazole, imidazole or benzotriazole, these nitrogen-containing heterocyclic compounds being optionally substituted with afore-mentioned C$_{1-6}$ alkyl group, C$_{1-6}$ alkoxy group, halogen atom, oxo group, thioxo group or C$_{1-6}$ alkylthio group). As the active ester, those which can be used for the same purpose in the fields of β-lactam and peptide synthesis can all be used, which are exemplified by, —besides organic phosphoric acid ester (e.g. diethoxy phosphoric acid ester or diphenoxy phosphoric acid)—, p-nitrophenyl ester, 2,4-dinitrophenyl ester, cyanomethyl ester, pentachlorophenyl ester, N-hydroxysuccinimide ester, N-hydroxyphthalimide ester, 1-hydroxybenzotriazole ester, 6-chloro-1-hydroxybenzotriazole ester, 1-hydroxy-1H-2-pyridone ester. The active thioester can be exemplified by esters with aromatic heterocyclic thiol compounds (e.g. 2-pyridylthio ester, 2-benzothiazolylthiol ester, these heterocyclic rings being substituted with afore-mentioned C$_{1-6}$ alkyl group, C$_{1-6}$ alkoxy group, halogen atom or C$_{1-6}$ alkylthio group). On the other hand, the 7-amino compound [II] can be used as free, a salt or ester thereof. Salts of the 7-amino compound [II] are exemplified by inorganic base salts, ammonium salt, organic base salts, inorganic acid addition salts or organic acid addition salts. There may be mentioned, as inorganic base salts, alkali metal salts (e.g. sodium salts or potassium salts) and alkaline earth metal salts (e.g. calcium salts); as organic base salts, for example trimethylamine salts, triethylamine salts, tert-butyldimethylamine salts, dibenzylmethylamine salts, benzyldimethylamine salts, N,N-dimethylaniline salts, pyridine salts or quinoline salts; as inorganic acid addition salts, for example hydrochlorides, hydrobromides, sulfates, nitrates or phosphates; and as organic acid addition salts, formates, acetates, trifluoroacetates, methanesulfonates, or p-toluenesulfonates. As the esters of the 7-amino compound [II], esters already referred to as ester derivatives of the compound [I] can also be counted, more concretely, C$_{1-6}$ alkyl* ester, C$_{2-6}$ alkenyl ester, C$_{3-10}$ cycloalkyl ester, C$_{3-6}$ cycloalkyl C$_{1-6}$ alkyl ester, C$_{6-10}$ aryl* ester, C$_{7-12}$ aralkyl* ester, di-C$_{6-10}$ aryl-methyl ester, tri-C$_{6-10}$ aryl-methyl ester or C$_{2-6}$ alkanoyloxy C$_{1-6}$ alkyl ester. The starting material R$^b$OH as well as salts and reactive derivatives thereof can be easily prepared by known methods or analogous methods thereto. A reactive derivative of the compound R$^b$OH, after isolation from the reaction mixture, can be allowed to react with a 7-amino compound [II], or as the reaction mixture containing the reactive derivative of the compound R$^b$OH before the isolation, it can be allowed to react with a 7-amino compound [II]. When the carboxylic acid R$^b$OH is used in the state of its free acid or salt, a suitable condensing agent is employed. As the condensing agents, there may be counted N,N'-di-substituted carbodiimides e.g. N,N'-dicyclohexylcarbodiimide; azolides e.g. N,N'-carbonyldiimidazole or N,N'-thiocarbonyldiimidazole; dehydrating agents e.g. N-ethoxycarbonyl-2-ethoxy-1,2-dihydroquinoline, phosphorus oxychloride or alkoxyacetylene; 2-halogenopyridinium salts e.g. 2-chloropyridinium methyl iodide or 2-fluoropyridinium methyl iodide. The reactions where these condensing agents are employed are considered to proceed via reactive derivatives of the carboxylic acid R$^b$OH. These reactions are generally conducted in a solvent which does not hamper the reaction. These solvents may be exemplified by ethers such as dioxane, tetrahydrofuran, diethyl ether, tert-butyl methyl ether, diisopropyl ether or ethylene glycol dimethyl ether; esters such as ethyl formate, ethyl acetate or n-butyl acetate; halogenated hydrocarbons such as dichloromethane, chloroform, carbon tetrachloride, trichlene or 1,2-dichloroethane; hydrocarbons such as n-hexane, benzene or toluene; amides such as formamide, N,N-dimethylformamide or N,N-dimethylacetamide; ketones such as acetone, methyl ethyl ketone or methyl isobutyl ketone; or nitriles such as acetonitrile or propionitrile, and, besides, dimethyl sulfoxide, sulfolane, hexamethylphosphoramide or water, singly or in combination. The amount of acylating agent (R$^b$OH) is usually 1–5 mol., preferably 1–2 mol., relative to 1 mol. of the 7-amino compound [II]. The reaction is conducted within the temperature range of −80°∼80° C., preferably −40°∼50° C., most preferably −30°∼30° C. The reaction time varies with kinds of the 7-amino compound [II] and carboxylic acid R$^b$OH, kinds of the solvent (mixture ratio as well when mixture solvents are used) and reaction temperatures, but it is usually within the range from one minute to 72 hours, preferably from 15 minutes to three hours. When an acid halide is employed as the acylating agent, the reaction can be conducted in the presence of a deacidifying agent for the purpose of eliminating from the reaction system the hydrogen halogenide to be liberated. The deacidifying agent may be exemplified by inorganic bases such as sodium carbonate, potassium carbonate, calcium carbonate or sodium hydrogen carbonate; tertiary amines such as triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine or N-methylmorpholine; or alkylene oxides such as propylene oxide or epichlorohydrin.

By the method mentioned above, the compound [VII] described in the foregoing can be synthesized. The reaction scheme is as follows:

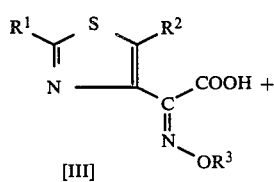

-continued

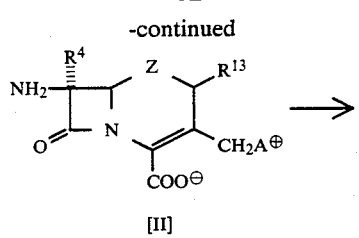

[II]

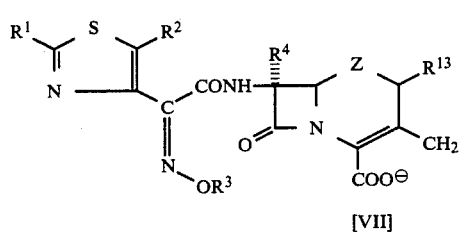

[VII]

The carboxylic acid [III] can be easily prepared by a known process or a process analogous thereto.

(3-2): By allowing a compound representable by the general formula:

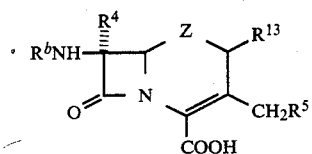 [X]

wherein $R^b$ stands for acyl group, and other symbols are of the same meaning as defined above or a salt or ester thereof to react with a pyrazole compound of the general formula A′ wherein A′ is of the same meaning as defined above or a salt thereof, a compound $[I^b]$ ($R^0 = R^b$) can be synthesized, which is shown by the following reaction scheme:

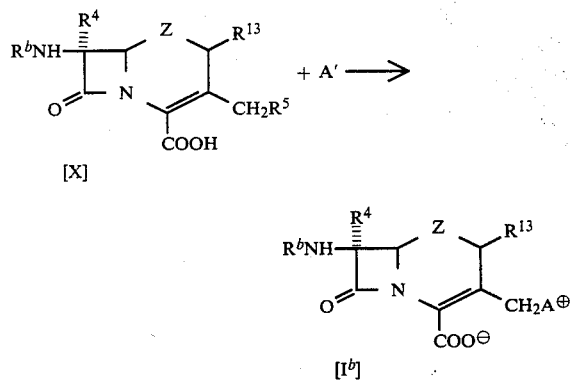

wherein the symbol $R^b$ stands for acyl group and the symbols Z, $R^4$, $R^{13}$, $R^5$ and A are of the same meaning as defined above.

This reaction is substantially the same as that mentioned in the Production Method (1) above, namely, pyrazole compound A′ or a salt thereof is allowed to react with a compound [X] or a salt or ester thereof to cause nucleophilic substitution to thereby synthesize a compound $[I^b]$ ($R^0 = R^b$). In the compound [X], $R^5$ stands for, also here, hydroxyl group, acyloxy group, carbamoyloxy group, substituted carbamoyloxy group or halogen atom. The compound [X] can be used in the free state, or salts or esters thereof. The salts and esters of the compound [X] are those mentioned as salts and esters of the 7-amino compound [II] in the above Production Method (3-1). The compound [X], salts and esters thereof can be easily prepared by known methods or analogous ones thereto. On the other hand, the pyrazole compound A′ stands for an optionally substituted pyrazole forming a fused ring at the 1,5-position. The fused ring means a form of fusing between the pyrazole ring and the 5- to 6-membered aromatic heterocyclic ring. Thus-fused ring may be further fused with another aromatic ring or aromatic heterocyclic ring. The optionally substituted pyrazole (A′) forming a fused ring at the 1,5-position may be represented by the general formula;

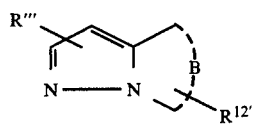

The symbol B in the formulae of fused pyrazole A′ is of the same meaning as that of Symbol B in A groups defined in the above. Hence, the compound A′ is exemplified by

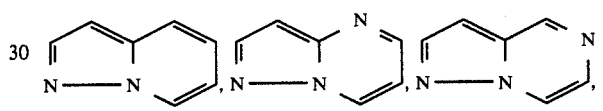

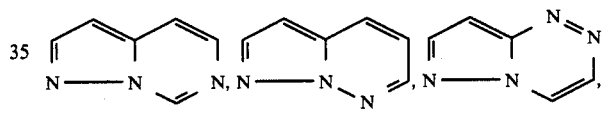

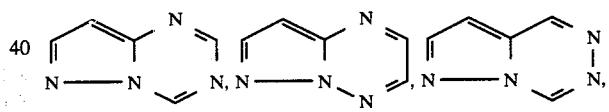

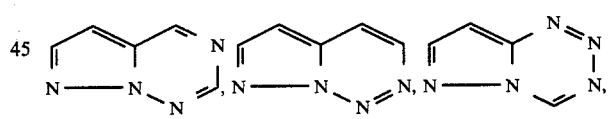

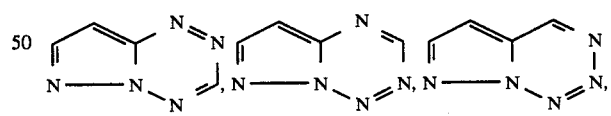

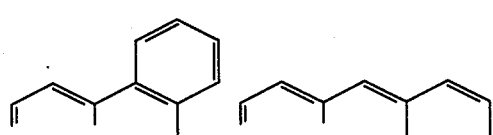

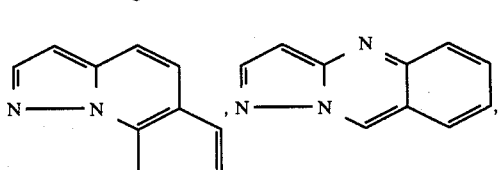

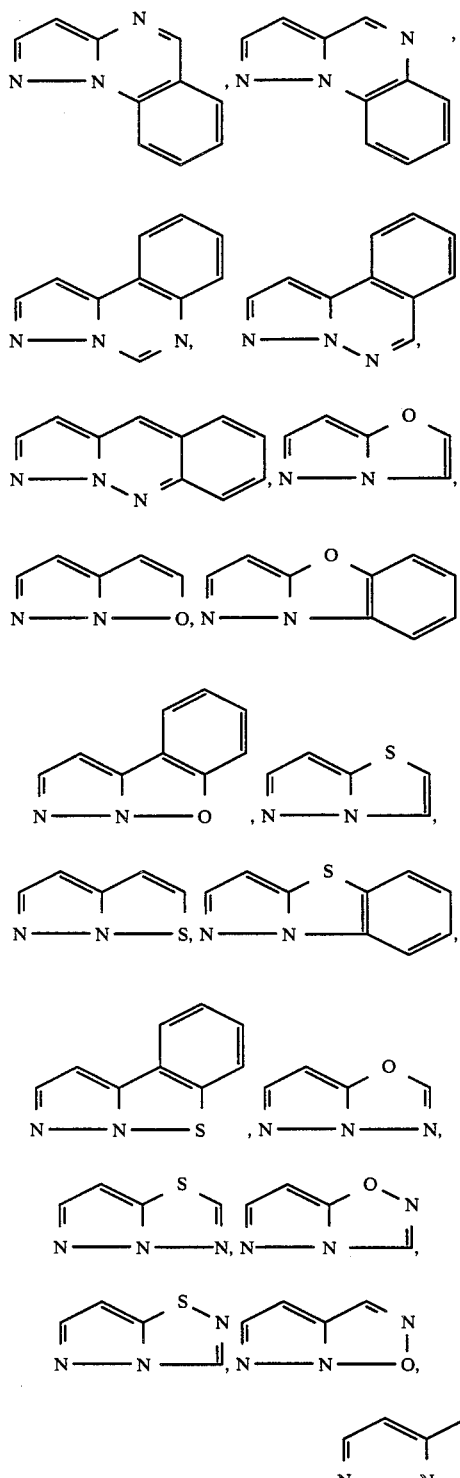

The substituents $R^{11'}$ and $R^{12'}$ on the pyrazole compound A' are those mentioned on the substituents $R^{11}$ and $R^{12}$ of the group A. And, in the compound A', the 3,4-position of the pyrazole ring may be fused with an alicyclic ring, aromatic ring or heterocyclic ring, which may be exemplified by In the above, B and $R^{12'}$ are of the same meaning as defined in the foregoing. The above-mentioned substituents $R^{11'}$ and $R^{12'}$ may be further substituted. The pyrazole compound A' may be used as salts thereof, which may be exemplified by inorganic acid addition salts e.g. hydrochloride, hydrobromide, sulfate, nitrate or phosphate, or organic acid addition salts e.g. formate, acetate, trifluoroacetate, methanesulfonate or p-toluenesulfonate. The pyrazole compound A' and its salt may be synthesized, in general, by known methods described in literature references or by analogous methods thereto. The nucleophilic substitution to the compound [X] with the pyrazole compound A' is a per se well known reaction, which is usually conducted in a solvent, for example, ethers, esters, halogenated hydrocarbons, hydrocarbons, amides, ketones, nitriles or water, which are used in the Production Method (3-1). Besides, alcohols such as methanol, ethanol, n-propanol, isopropanol, ethylene glycol or 2-methoxyethanol may be used as well. When the pyrazole compound A' is in liquid state, it may be sometimes used in a large excess amount (e.g. 10-200 mol.) relative to the compound [X] to allow it to act as also the solvent. In this case, use of the above-mentioned solvents is unnecessary, or the pyrazole A' may be used as a mixture solvent with any of the above-mentioned solvents.

(3-2-1): The case where $R^5$ stands for acyloxy group, carbamoyloxy group or a substituted carbamoyloxy group Preferable solvents are water and mixture solvents of water-miscible organic solvents and water. Among the water-miscible organic solvents, preferable ones are exemplified by acetone, methyl ethyl ketone and acetonitrile. The amount of the nucleophilic reagent A' is usually 1-5 moles, preferably 1-3 moles, relative to 1 mole of the compound [X]. The reaction is conducted within a temperature ranging from 10° C. to 100° C., preferably from 30° C. to 80° C. The reaction time depends on the kinds of the compound [X] and the compound A', kinds of solvents (mixture ratios when mixture solvents are used), or reaction temperature, and ranges usually from 30 minutes to five days, preferably from one hour to five hours. The reaction is advantageously conducted at pH 2–8, preferably near neutral pH, i.e., pH 5–8. The reaction readily proceeds usually in the presence of 2–30 equivalents of an iodide or thiocyanate. These salts are exemplified by sodium iodide, potassium iodide, sodium thiocyanate and potassium thiocyanate. In addition to the above exemplified salts, a surface-active quaternary ammonium salt such as trimethylbenzylammonium bromide, triethylbenzylammonium bromide or triethylbenzylammonium hydroxide may be sometimes used for allowing the reaction to proceed smoothly.

(3-2-2): The case where $R^5$ stands for hydroxyl group

The reaction is conducted in the presence of an organic phosphorus compound according to the manner described in, for example, Publication of Unexamined Patent Application (Kokai) in Japan, No. Sho 58-43979. The organic phosphorus compound is exemplified by o-phenylene phosphorochloridate, o-phenylene phosphorofluoridate, methyl o-phenylene phosphate, ethyl o-phenylene phosphate, propyl o-phenylene phosphate, isopropyl o-phenylene phosphate, butyl o-phenylene phosphate, isobutyl o-phenylene phosphate, sec.-butyl o-phenylene phosphate, cyclohexyl o-phenylene phosphate, phenyl o-phenylene phosphate, p-chlorophenyl o-phenylene phosphate, p-acetylphenyl o-phenylene phosphate, 2-chloroethyl o-phenylene phosphate, 2,2,2-trichloroethyl o-phenylene phosphate, ethoxycarbonylmethyl o-phenylene phosphate, carbamoylmethyl o-phenylene phosphate, 2-cyanoethyl o-phenylene phosphate, 2-methylsulfonylethyl o-phenylene phosphate, benzyl o-phenylene phosphate, 1,1-dimethyl-2-propenyl o-phenylene phosphate, 2-propenyl o-phenylene phosphate, 3-methyl-2-butenyl o-phenpylene phosphate, 2-thienylmethyl o-phenylene phosphate, 2-furfurylmethyl o-phenylene phosphate, bis-o-phenylene pyrophosphate, 2-phenyl-1,3,2-benzodioxaphosphole-2-oxide, 2-(p-chlorophenyl)-1,3,2-benzodioxaphosphole-2-oxide, 2-butyl-1,3,2-benzodioxaphosphole-2-oxide, 2-anilino-1,3,2-benzodioxaphosphole-2-oxide, 2-phenylthio-1,3,2-benzodioxaphosphole-2-oxide, 2-methoxy-5-methyl-1,3,2-benzodioxaphosphole-2-oxide, 2-chloro-5-ethoxycarbonyl-1,3,2-benzodioxaphosphole-2-oxide, 2-methoxy-5-ethoxycarbonyl-1,3,2-benzodioxaphosphole-2-oxide, 5-ethoxycarbonyl-2-phenyl-1,3,2-benzodioxaphosphole-2-oxide, 2,5-dichloro-1,3,2-benzodioxaphosphole-2-oxide, 4-chloro-2-methoxy-1,3,2-benzodioxaphosphole-2-oxide, 2-methoxy-4-methyl-1,3,2-benzodioxaphosphole-2-oxide, 2,3-naphthalene methyl phosphate, 5,6-dimethyl-2-methyoxy-1,3,2-benzodioxaphosphole-2-oxide, 2,2-dihydro-4,5,6,7-tetrachloro-2,2,2-trimethoxy-1,3,2-benzodioxaphosphole, 2,2-dihydro-4,5,6,7-tetrachloro-2,2,2-triphenoxy-1,3,2-benzodioxaphosphole, 2,2-dihydro-2,2-ethylenedioxy-2-methoxy-1,3,2-benzodioxaphosphole, 2,2-dihydro-benzyl-2,2-dimethoxy-1,3,2-benzodioxaphosphole, 2,2-dihydro-4,5-benzo-2,2,2-trimethoxy-1,3,2,-benzodioxaphosphole, 2,2-dihydro-2,2,2-triphenoxy-1,3,2-benzodioxaphosphole, 2,2-dihydro-2,2-(o-phenylenedioxy)-2-phenoxy-1,3,2-benzodioxaphosphole, 2-chloro-2,2-dihydro-2,2-(o-phenylenedioxy)-1,3,2,-benzodioxaphosphole 2,2-dihydro-2-methoxy-2,2-(o-phenylenedioxy)-1,3,2-benzodioxaphosphole, 2,2-dihydro-2,2,2-trichloro-1,3,2-benzodioxaphosphole, 9,10-phenanthrenedioxytrimethoxyphosphorus, o-phenylen phosphorochloridite, o-phenylene phosphorobromidite, o-phenylene phosphorofluoridite, methyl o-phenylene phosphite, butyl o-phenylene phosphite methoxycarbonylmethyl o-phenylene phosphite, phenyl o-phenylene phosphite, p-chloro (or p-nitro)phenyl o-phenylene phosphite, 2-phenyl-1,3,2-benzodioxaphosphole, bis-o-phenylene pyrophosphite, 2-methoxy-5-methyl-1,3,2-benzodioxaphosphole, 5-acetyl-2-phenoxy-1,3,2-benzodioxaphosphole, 9,10-phenanthrene phosphorochloridite, 2-chloro-4-methyl-1,3,2-benzodioxaphosphole,5-ethoxycarbonyl-2-phenyl-1,3,2-benzodioxaphosphole,2-chloro-2-thioxo-1,3,2-benzodioxaphosphole,2-phenoxy-2-oxo-1,3,2-benzodiazaphosphole,2-phenoxy-1,3,2-benzodioxaazaphosphole,2,2-dihydro-2-oxo-2-methoxy-4,5-dimethyl-1,3,2-dioxaphosphole,2,2-dihydro-2-oxo-2-chloro-4,5-dimethyl-1,3,2-dioxaphosphole,2,2-dihydro-2-oxo-2-(1-imidazolyl)-4,5-dimethyl-1,3,2-dioxaphosphole,2,2-dihydro-2,2-ethylenedioxy-2-methoxy-4,5-dimethyl-1,3,2-dioxaphospole,2,2-dihydro-2,2-dimethoxy-2-phenoxy-4,5dimethyl-1,3,2-dioxaphosphole,2,2-dihydro-2,2,2-trimethoxy-4,5-dimethyl-1,3,2-dioxaphosphole,2,2-dihydro-2,2,2-triphenoxy-4,5-dimethyl-1,3,2-dioxaphosphole,2,2-dihydro-2,2,2-triethoxy-4,5-diphenyl-1,3,2-dioxaphosphole,2,2-dihydro-2,2,2-trimethoxy-4,5-diphenyl-1,3,2-dioxaphosphole,2,2-dihydro-2-oxo-2-methoxy-4,5-diphenyl-1,3,2-dioxaphospole, 2,2-dihydro-2,2,2-trimethoxy-1,3,2-dioxaphosphole,2,2-dihydro-2,2,2-trimethoxy-4-phenyl-1,3,2-dioxaphosphole,2,2-dihydro-2,2,2-trimethoxy-4-methyl-1,3,2-dioxaphosphole,2,2-dihydro-2,2,2-trimethoxy-4-methyl-5-phenylcarbamoyl-1,3,2-dioxaphosphole,2,2,4,5,6,7-hexahydro-2,2,2-trimethoxy-1,3,2-benzodioxaphosphole,2,2'-oxybis(4,5-dimethyl-2,2-dihydro-1,3,2-dioxaphosphole) and 2,2'-oxybis(4,5-dimethyl-2,2-dihydro-1,3,2-dioxaphosphole-2-oxide). For the reaction, any solvent can be employed if only it does not hamper the reaction, and, preferably, the afore-mentioned ethers, esters, halogenated hydrocarbons, hydrocarbons, amides, ketones and nitriles may be used singly or in a mixture thereof. Especially, use of dichloromethane, acetonitrile, formamide, a mixture of formamide and acetonitrile, or a dichloromethane and acetonitrile brings about a preferable result. The amounts of the nucleophilic reagent A' and the organic phosphorus compound are respectively, relative to 1 mole of the compound [X], 1–5 moles and 1–10 moles, more preferably 1–3 moles and 1–6 moles. The reaction is conducted within the temperature range from −80° C. to 50° C., preferably from −40° C. to 40° C. The reaction time is usually within the range of one minute to 15 hours, preferably five minutes to two hours. To the reaction system may be added an organic base. As the organic base may be exemplified amines such as triethylamine, tri-(n-butyl)amine, di-(n-butyl)amine, diisobutylamine, dicyclohexylamine or 2,6-lutidine. The amount of the base to be added is preferably 1–5 moles relative to 1 mole of the compound [X].

(3-2-3): The case where $R^5$ stands for halogen atom

Preferable solvents are the afore-mentioned ethers, esters, halogenated hydrocarbons, hydrocarbons, amides, ketones, nitriles, alcohols and water. The amount of the nucleophilic reagent A' to be used is usually, relative to one mole of the compound [X], 1–5 moles, preferably 1–3 moles. The reaction is conducted within a temperature range of 0°–80° C., preferably 20°–60° C. The reaction time is usually 30 minutes to 15 hours, preferably 1–5 hours. For accelerating the reaction, the reaction may be conducted in the presence of a dehalogenating agent. As such dehalogenating agents, there may be counted deacidifying agents such as inorganic bases, tertiary amines and alkylene oxides mentioned in the Production Method (3-1), while the nucleophilic reagent A' itself may be allowed to act as the dehalogenating agent also. In this case, the compound A' is used in an amount of two moles or more relative to one mole of the compound [X]. The halogen atom shown by $R^5$ is exemplified by chlorine, bromine and iodine, and preferably iodine. The compound [X] wherein $R^5$ stands for iodine can be easily produced in accordance with the method described in, for example, Publication of Unexamined Patent Application (Kokai) in Japan, No. Sho 58-57390 or a method analogous thereto.

By the method described here, the afore-mentioned compound [VII] or [VIII] for example can be synthesized. The reaction schemes are as follows:

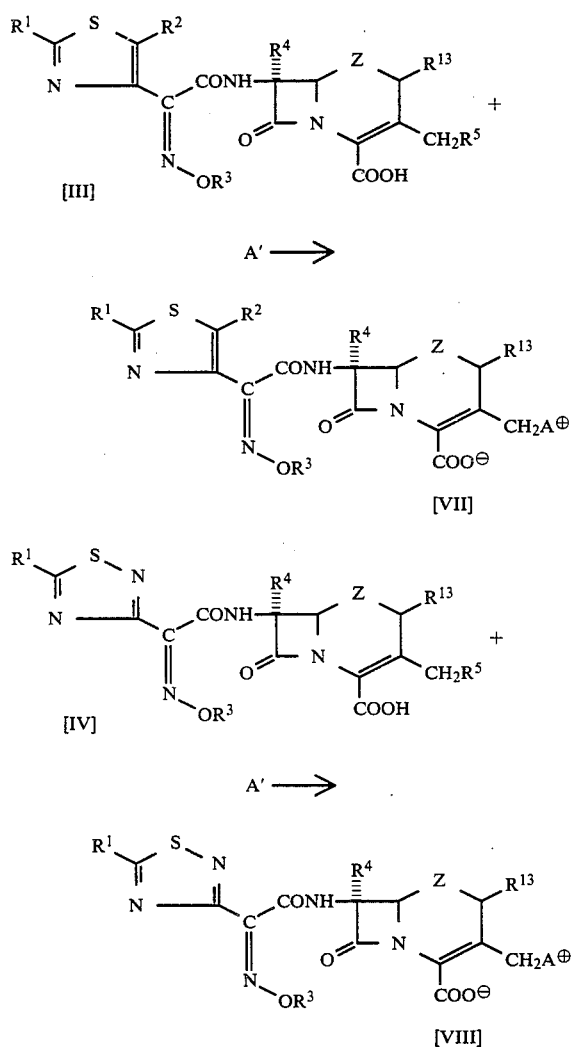

The compounds [III] and [IV] can be easily prepared by a known method or a method analogous thereto.

The following compound [X] including the compounds [VII] and [VIII] can also be prepared by, besides the above-mentioned Production Method (3-1) or (3-2), the Production Method (3-3) to be described later. The compound [VII] can also be prepared by, besides the Production Method (3-1), (3-2) or (3-3), the Production Method (3-4) to be described later. (3-3):

The reaction scheme is as follows:

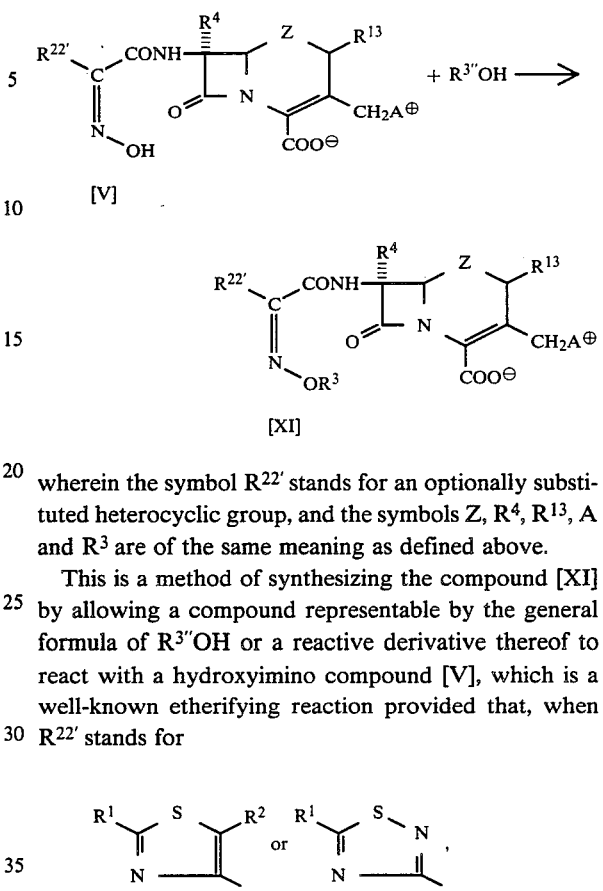

wherein the symbol $R^{22'}$ stands for an optionally substituted heterocyclic group, and the symbols Z, $R^4$, $R^{13}$, A and $R^3$ are of the same meaning as defined above.

This is a method of synthesizing the compound [XI] by allowing a compound representable by the general formula of $R^{3''}OH$ or a reactive derivative thereof to react with a hydroxyimino compound [V], which is a well-known etherifying reaction provided that, when $R^{22'}$ stands for the resultant compounds [XI] are respectively [VII] or [VIII]. $R^{3''}$ stands for an optionally substituted hydrocarbon residue which is the same as that referred to in $R^3$. $R^{3''}OH$ may be employed as it is or as a reactive derivative thereof. Reactive derivatives of $R^{3''}OH$ are representable by the general formula $R^{3''}Y$, having a group to be liberated together with the hydrogen atom of the hydroxyimino compound [V]. The group Y to be liberated together with hydrogen atom may be exemplified by halogen atom, sulfo group or mono-substituted sulfonyloxy group. The halogen atom may be exemplified by chlorine, bromine or iodine. The mono-substituted sulfonyloxy group may be exemplified by $C_{1-6}$ alkylsulfonyloxy and $C_{6-10}$ arylsulfonyloxy groups e.g. methanesulfonyloxy, ethanesulfonyloxy, benzenesulfonyloxy or p-toluenesulfonyloxy. When a $C_{1-4}$ alkylether derivative of the compound [V] is intended, there may be used, besides the above-mentioned reaction derivatives, $C_{1-4}$ diazoalkane such as diazomethane or diazoethane, and di-$C_{1-4}$ alkyl sulfate such as dimethyl sulfate or diethyl sulfate.

The compound [V] can be prepared by the acylation as mentioned above in the Production Method (3-1) or the nucleophilic substitution as mentioned above in the Production Method (3-2). The reaction schemes are as follows, respectively:

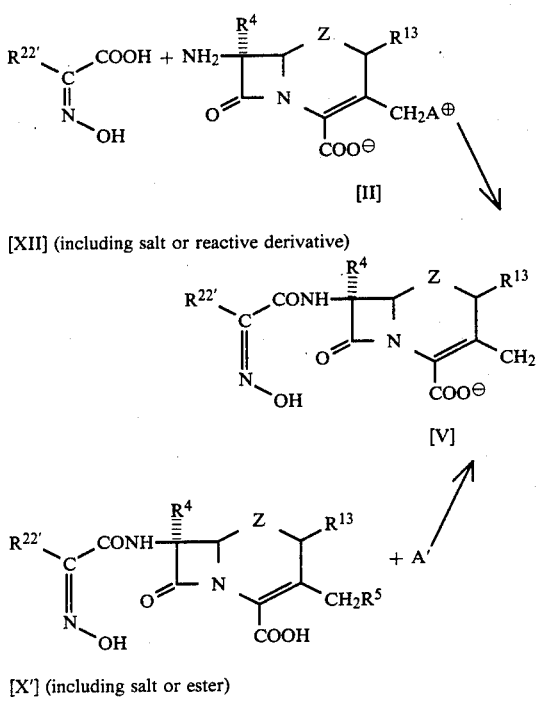

[XII] (including salt or reactive derivative)

[V]

[X'] (including salt or ester)

The starting materials [XII] and [X'] can be easily prepared by a known method or an analogous one thereto. The compound R³"OH and the reactive derivative thereof can also be easily prepared by a known method or an analogous one thereto.

(3-3-1): The case where R³"OH is used

A suitable dehydrating agent is allowed to react with a hydroxyimino compund [V] to synthesize a compound [XI]. The dehydrating agent may be exemplified by phosphorus oxychloride, thionyl chloride, dialkyl azodicarboxylate (usally used in the presence of phosphine) or N,N-dicylohexylcarbodiimide, and preferably diethyl azodicarboxylate in the presence of triphenyl phosphine. The reaction in which diethyl azodicarboxylate is used in the presence of triphenyl phosphine is usually conducted in an anhydous solvent such as ethers or hydrocarbons mentioned above. Relative to 1 mole of the compound [V], 1–1.5 mole each of the compound R³"OH, ethyl azodicarboxylate and triphenyl phosphine is employed. The reaction requires 1–4 days at a temperature range of 0°–50° C.

(3-3-2): The case where R³"Y is used

The reaction between R³"Y and a hydroxyimino compound [V] is a conventional etherification reaction, which is conducted in a solvent. The solvent is exemplified also here by those as mentioned in the Production Method (3-1) above, i.e., ethers, esters, hydrogenated hydrocarbons, hydrocarbons, amides, ketones, nitriles, alcohols, water or a mixture of any of them, preferably a mixture solvent of a water-miscible solvent and water (e.g. aqueous methanol, aqueous ethanol, aqueous acetone and aqueous diemethyl sulfoxide). The reaction may also be allowed to proceed smoothly in the presence of a suitable base. The base may be exemplified by inorganic bases such as alkali metal salts e.g. sodium carbonate, sodium hydrogencarbonate or potassium carbonate, or alkali metal hydroxides e.g. sodium hydroxide or potassium hydroxide. This reaction may be conducted in a buffer solution of pH 7.5-8.5. The mole numbers of a reagent R³"Y and the base relative to 1 mole of the starting compound [V] are respectively 1–5 and 1–10, preferably 1–3 and 1–5, respectively. The reaction temperature is in the range from −30° C. to 100° C., preferably, 0° C. to 80° C. The reaction time ranges from 10 minutes to 15 hours, preferably from 30 minutes to 5 hours.

(3-3-3): The case where C₁₋₄ diazoalkane is used

The reaction is usually conducted in a solvent. As the solvent are employed, for example, the afore-mentioned ethers and hydrocarbons. A hydroxyimino compound [V] is dissolved in a solvent, to which is then added a solution of a diazoalkane compound, whereupon the reaction proceeds. The reagent is used, relative to 1 mole of the compound [V], in an amount of 1–10 moles, preferably 1–5 moles. The reaction is conducted at a relatively low temperature range of from −50° C. to 20° C., preferably from −30° C. to 0° C. The reaction time ranges from 1 minute to 5 hours, preferably 10 minutes to one hour.

(3-3-4): The case where di-C₁₋₄ alkylsulfate is used

The reaction is conducted usually in water or a mixture solvent of a water-miscible solvent and water. The mixture solvents are those mentioned in the Production Method (3-3-2). This reaction is usually conducted in the presence of an inorganic base, for example, an alkali metal hydroxide such as sodium hydroxide and potassium hydroxide. The reagent is used in an amount of 0.5-10 moles, preferably 1–2 moles, relative to 1 mole of the compound [V]. The reaction temperature ranges from 20° C. to 100° C., preferably 50°–100° C. The reaction time ranges from 10 minutes to 5 hours, preferably from 30 minutes to 3 hours.

(3-4): The reaction scheme is as follows:

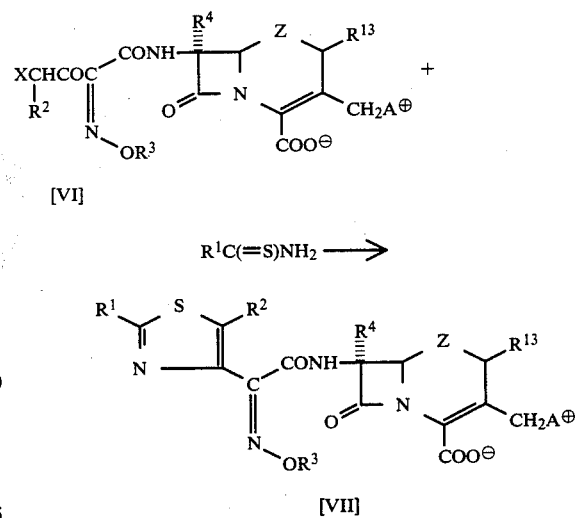

wherein the symbols Z, R⁴, R¹³, A, R¹, R² and R³ are of the same meaning as defined above.

This is a method of synthesizing the end product [VII] by allowing a compound [VI] to react with a thiourea representable by the general formula R¹C(=S)NH₂ or a derivative thereof. The compound [VI] is employed in its free state or as a salt or ester thereof. X in the compound [VI] stands for a halogen atom e.g. chlorine, bromine or iodine. Salts of the compound [VI] include those (inorganic base salts, ammonium salt, organic base salts, inorganic acid addition salts or organic acid addition salts, for example) of the 7-amino compound [II] exemplified in the Production Method (3-1). Easters of the compound [VI] as well mentioned those of the 7-amino compound [II] exemplified in the Production Method (3-1) ($C_{1-6}$ alkyl* ester, $C_{2-6}$ alkenyl ester, $C_{3-10}$ cycloalkyl ester, $C_{3-6}$ cycloalkyl $C_{1-6}$ alkyl ester, $C_{6-10}$ aryl* ester, $C_{7-12}$ aralkyl* ester, di-$C_{6-10}$ aryl-methyl ester, tri-$C_{6-10}$ arylmethyl ester and $C_{2-6}$ alkanoyloxy $C_{1-6}$ alkyl ester). The starting compound [VI] can be prepared by allowing a compound representable by the general formula:

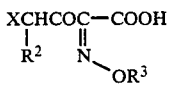

wherein the symbols are of the same meaning as defined above or a salt or reactive derivative thereof to react with the afore-mentioned 7-amino compound [II] or a salt or ester thereof according to the manner as described in the Production Method (3-1) above. Compounds representable by the general formula;

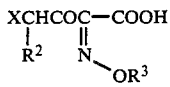

or reactive derivatives thereof can be easily prepared by a per se conventional process or an analogous one thereto. The reaction between a compound [VI] and $R^1C(=S)NH_2$ is usually conducted in a solvent. The solvent may be exemplified by ethers such as dioxane, tetrahydrofuran and diethyl ether, alcohols such as methanol, ethanol and n-propanol, or amides such as dimethylformamide and dimethylacetamide. The amount of thiourea or a reactive derivative thereof representable by $R^1C(=C)NH_2$ is usually, relative to the compound [VI], 1-5 moles, preferably 1-3 moles. The reaction is conducted at temperatures ranging form 0° C. to 100° C., preferably 20°-60° C. The reaction time usually ranges from 30 minutes to 15 hours, preferably 1-5 hours.

When the compounds [$I^b$] produced by the above-mentioned Production Methods (3-1) to (3-4) have hydroxyimino (or substituted hydroxyimino) group in the substituent $R^b$, e.g. in the case of the compounds [VII], [VIII] and so on, there may sometimes be the cases where the compounds [$I^b$] are obtained as a mixture of syn[Z]- and anti[E]-isomers.

In the above-mentioned Production Method (3-1)-(3-4), there may sometimes be the cases where the compound [XI] including the compounds [VII] and [VIII] are obtained as a mixture of syn[Z]- and anti[E]-isomers. For isolating the desired syn-isomer from the mixture, a per se known process or analogous ones thereto may be employed. These processes may be exemplified by fractionation by utilizing the differences in, for example, solubilities or crystallizability, isolation by means of chromatography, or isolation utilizing the differences in hydrolysis rates between the respective ester derivatives.

PRODUCTION METHOD (4)

Compound [I] ($R^0 = R^c$; $R^c$ denotes amino-protecting group)

For example, (4-1): By allowing the 7-amino compound [II] ([I], $R^0$=hydrogen atom) obtained by the above Production Method (1) or a salt or ester thereof to react with an amino-protecting reagent e.g. an oxycarbonylation reagent, [I] ($R^0 = R^c$) can be synthesized. The oxycarbonylation reagent

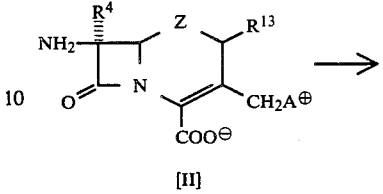

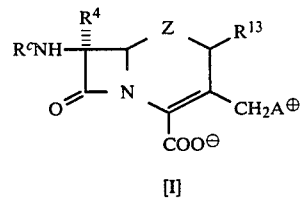

($R^0 = R^c$)

is exemplified by substituted oxycarbonyl halide (e.g. chlorine, bromine or iodine as halogen), substituted oxycarbonyl azide, substituted oxycarbonic anhydride, substituted oxycarbonyl sulfide or substituted oxycarbonyl azolide (e.g. imidazole, N-methylimidazole, triazole, 2-thiooxazolidine or 2-oxoxazolidine as azole). The reaction is conducted usually in a solvent, preferably an anhydrous solvent. As such solvents, use is often made of ethers, e.g. dioxane, tetrahydrofuran, diethyl ether, tert-butyl methyl ether, diisopropyl ether or ethylene glycol dimethyl ether, halogenated hydrocarbons e.g. dichloroethane, chloroform, carbon tetrachloride, trichlene or 1,2-dichloroethane, nitriles, e.g. acetonitrile, alcohols e.g. methanol, ethanol, propanol or butanol, hydrocarbons, e.g. n-hexane, benzene or toluene, amides e.g. dimethylformamide, dimethylacetamide or hexamethylphosphorus triamide, or sulfoxides e.g. dimethyl sulfoxide, singly or as a mixture solvent. The amount of the oxycarbonylation reagent is usually, relative to 1 mole of the 7-amino compound [II], 1-5 moles, preferably 1-2 moles. The reaction is conducted within the temperature range of from −80° C. to 80° C., preferably from −40° C. to 50° C., most preferably from −30° C. to 30° C. While the reaction time varies with kinds of the 7-amino compound [II] and the oxycarbonylation reagents, kinds of solvents and reaction temperatures, it ranges from one minute to 48 hours, preferably from ten minutes to two hours. When a substituted oxycarbonyl halide is employed as the oxycarbonylation reagents, the reaction may be conducted in the presence of a deacidifying agent for the purpose of eliminating from the reaction system the hydrogen halogenide to be liberated. The deacidifying agent may be exemplified by inorganic bases such as sodium carbonate, potassium carbonate, calcium carbonate or sodium hydrogencarbonate; tertiary amines such as triethylamine, tri-(n-propyl)amine, tri-(n-butyl)amine, diisopropylethylamine, cyclohexyldimethylamine, pyridine, lutidine, γ-collidine, N,N-dimethylaniline, N-methylpiperidine, N-methylpyrrolidine or N-methylmorpholine; or alkylene oxides such as propylene oxide or epichlorohydrin.

(4-2): By allowing the compound [XII] or a salt or ester thereof to react with the pyrazole compound A' wherein A' is of the same meaning as defined above or salt thereof, a compound [I$^c$] (R$^0$=R$^c$) can also be synthesized.

The reaction is shown by the following scheme:

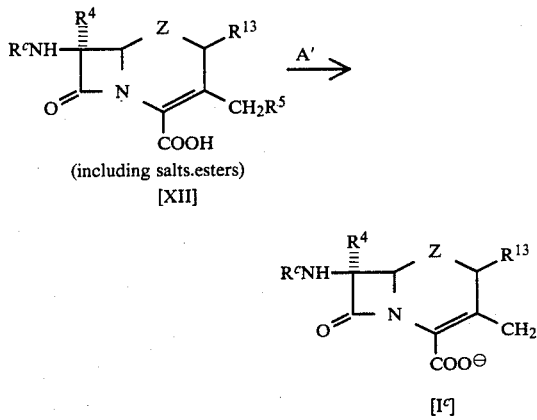

(including salts.esters)
[XII]

[I$^c$]

wherein the symbols are of the same meaning as defined above.

This reaction substantially the same as that mentioned in the Production Methods (1) and (3-2). The starting compound [XII], salts and esters thereof can be easily prepared by the same procedure as described in the production Method (4-1) above, namely, the oxycarbonylation reagent is allowed to react with a compound [IX] or a salt or ester thereof to synthesized the compound [XII].

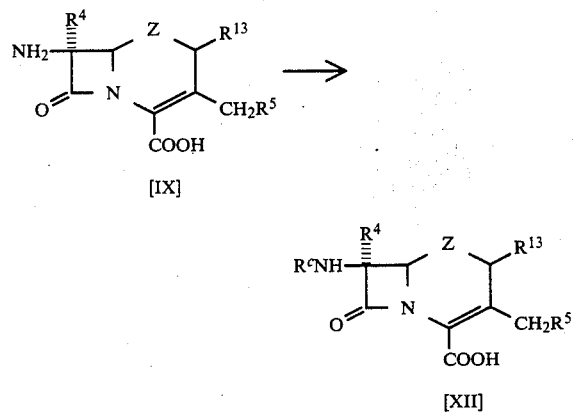

[IX]

[XII]

After the above-mentioned Production Method (1)-(4), when required, removal of protecting groups and purification are conducted to obtain the end product [I] of this invention. Methods of removing protecting groups and purification are described as follows:

Process of removing protecting group: As afore-mentioned, in the fields of β-lactam and peptide syntheses, amino-protecting groups have been sufficiently studied, and the method of protecting amino groups has been established. The method of removing the amino-protecting group has also been established, and, in the present invention as well, for removing protecting groups, conventional technique can be used as such. For example, monohalogenoacetyl group (chloroacetyl, bromoacetyl, etc.) can be removed by using thiourea; alkoxycarbonyl group (methoxycarbonyl, ethoxycarbonyl, tert-butoxycarbonyl, etc.) can be removed by using an acid (e.g. hydrochloric acid); aralkyloxycarbonyl group (e.g. benzyloxycarbonyl, p-methylbenzyloxycarbonyl or p-nitrobenzyloxycarbonyl) can be removed by means catalytic reduction; and 2,2,2-trichloroethoxycarbonyl can be removed by using zinc and an acid (e.g. acetic acid). On the other hand, in the case when the compound [I] as the intermediate has been esterified, the ester residue can be removed by a per se known process or an analogous one thereto. For example, 2-methylsulfonylethyl ester can be removed by using an alkali; aralkyl ester (benzyl ester, p-methyoxybenzyl ester, p-nitrobenzyl ester, etc.) can be removed by using an acid (e.g. trifluoroacetic acid) or by means of catalytic reduction; 2,2,2-trichloroethyl ester can be removed by using zinc and an acid (e.g. acetic acid); and silyl ester (e.g. trimethylsilyl ester or tert-butyldimethylsilyl ester) can be removed by using only water.

Process of purifying the compound [I]: The compound [I] produced in the reaction mixture by any of the processes described in detail in the foregoing Production Methods (1)-(4) and, upon necessity, followed by removal of protecting groups by conducting the above-mentioned process, can be isolated and purified by a known process such as extraction, column-chromatography, precipitation and recrystallization. On the other hand, the compound [I] thus isolated can be converted into then desired physiologically acceptable salts or bioavailably unstable non-toxic esters.

Sulfoxide ([I], Z=S→O) of the cephem compound ([I], Z=S) can be prepared by subjecting the compound ([I], Z=S) to a conventional oxidation. Oxidizing agents suitable for oxidation of sulfur atom of the cephem ring are exemplified by oxygen, peracid, hydroperoxide, or hydrogen peroxide, and the peracid may be given by mixing an acid with a peroxide in the reaction system of the oxidation. As such peracids, use is often made of peracetic acid, perbenzoic acid or p-chloroperbenzoic acid. The reaction is usually conducted in a solvent which is exemplified by ethers such as dioxane or tetrahydrofuran; halogenated hydrocarbons such as dichloromethane, chloroform or chlorobenzene; organic acids such as formic acid, acetic acid trifluoroacetic acid; or amides such as dimethylformamide or dimethylacetamide. The reaction temperature ranges from −20° C. to 80° C., and preferably a temperature as low as possible, i.e. ranging from −20° C. to 20° C. It is generally known that, when the cephem compound ([I], Z=S) is subjected to oxidation, sulfoxide having an S-configuration is produced. The R- and S-sulfoxide can be separated by utilizing the difference in solubility between them or the difference in travelling rate in chromatography. The above-mentioned oxidation to give sulfoxide can be conducted before or after the afore-mentioned Production Methods (1)-(4).

The compound [I] including compounds [VII] and [VIII] of this invention can be administered orally or non-orally as injections, capsules, tablets or granules, like known penicillin and cephalosporin preparations. The dosage is 0.5-80 mg/day, preferably 1-20 mg/day in 3-4 doses relative to one kilogram of the body weight of men and animals infected with pathogenic bacteria as set forth above. Carriers of injectable preparations are exemplified by distilled water or physiological saline. When used as capsule, powder, granule or tablet, the compound [I] is mixed with conventional pharmaceutically acceptable excipients (e.g. starch, maltose, sucrose, calcium carbonate or calcium phosphate), binders (e.g. starch, gum-arabica, carboxymethylcellulose, hydroxypropylcellulose or crystalline cellulose), lubricants (e.g. magnesium stearate or talc) and disintegrators (e.g. carboxymethyl calcium or talc).

A pharmaceutical composition containing the compound [I] is made by a known procedure. The composition is usually produced by mixing at least one of the compounds [I] or their salts or esters with the above carriers or excipients. The ratio of the compound [I] to the whole composition is usually 5 to 100%(w/w), preferably 20 to 100%(w/w) in solid composition such as capsules, tablets and granules, 5 to 30%(w/w) in liquid composition such as injections etc.

The compound [I] or its physiologically or pharmaceutically acceptable salt or ester is preferably administered as an injection for example for combatting against urinary tract infections caused by Escherichia coli. In this case, the dosage amount is in the range of from 1 to 20 mg/kg in 3 to 4 divided doses relative to one kilogrum of the body weight of adult human. The injection is easily prepared by dissolving or suspending the compound [I], its salt or ester into physiological saline.

The present invention will be further explained by the following Reference Examples and Working Examples, but those Examples are mere examples and do not restrict the present invention in any manner, including variations to such extent as not deviating the scope of this invention.

Elution in column-chromatography in the Reference Examples and Working Examples was conducted under observation by means of TLC (Thin-Layer Chromatography), wherein were employed BOF$_{254}$ (manufactured by E. Merck) as TLC plate, the solvent for elution in the column-chromatography as developing solvent, and a UV detector as detecting means. As silica-gel for the column, Kieselgel 60 (230–400 mesh) manufactured by E. Merck was employed. "Sephadex" is a product of Pharmacia Fine Chemicals. XAD-2 resin is a product of Rohm & Haas Co. NMR spectrum was determined by XL-100A (100 MHz)-, EM390 (90 MHz)-, EM360 (60 MHz)- or T$_{60}$(60 MHz)-type spectrometer using tetramethylsilane as internal or external standard, and all the δ values were shown by ppm. The numeral values parenthesized for mixture solvents mean the ratios by volume of each solvent mixed. "%" for solvents means number of grams in 100 ml of each solution. Symbols in the Reference Examples and Working Examples have respectively the meanings as follows:

s: singlet
d: doublet
t: triplet
q: quartet
Abq: AB type quartet
d. d: double doublet
m: multiplet
br.: broad
J: coupling constant
Hz: Hertz
mg: milligram
g: gram
ml: milliliter
l: liter
%: percent
DMSO: dimethylsulfoxide
D$_2$O: deuterium oxide
CDCl$_3$: deuterochloroform

REFERENCE EXAMPLE 1

7β-[2-(2-Chloroacetamidothiazol-4-yl)-2(Z)-methoxyiminoacetamido]-3-(3-oxobutyryloxymethyl)-3-cephem-4-carboxylic acid In a mixture of 500 ml of tetrahydrofuran and 500 ml of water is suspended 157 g of 7β-amino-3-(3-oxobutyryloxymethyl)-3-cephem-4-carboxylic acid. To the suspension is added little by little 141 g of sodium hydrogen carbonate with stirring. To the mixture is added 150 g of 2-(2-chloroacetamidothiazol-4-yl)-2(Z)-methoxyiminoacetyl chloride hydrochloride at 5° C., during 20 minutes with stirring, and the mixture was stirred for further one hour. After completion of the reaction, the reaction mixture is adjusted to pH 3.0 with 10% hydrochloric acid, and extracted twice with 1 l portions of a mixture is ethyl acetate-tetrahydrofuran (1:1). The extract is dried over anhydrous magnesium sulfate, and then the solvent is evaporated off under reduced pressure to leave colorless powder, which is triturated with 200 ml of ethyl acetate and collected by filtration to afford 253 g of the above-identified compound.

Elemental analysis for $C_{20}H_{20}ClN_5O_9S_2$: Calcd. (%): C, 41,85; H, 3,51; N, 12.20. Found (%): C, 41,39; H, 3.57; N, 11.94.

IR Spectrum $\nu_{max}^{KBr}$ cm$^{-1}$; 1780, 1740, 1700, 1655, 1540, 1410.

NMR spectrum (d$_6$-DMSO) δ: 2.20 (3H, s), 3.45 and 3.68 (2H, ABq, J=18 Hz), 3.65 (2H, s), 3.92 (3H, s), 4.38 (2H, s), 4.79 & 5.09 (2H, ABq, J=13 Hz), 5.18 (1H, d, J=5 Hz), 5.85 (1H, d. d, J×5 Hz & 8 Hz), 7.44 (1H, s), 9.66 (1H, d, J=8 Hz), 12.85 (1H, br. s).

REFERENCE EXAMPLE 2

7β-[2-(2-Aminothiazol-4-yl)-2(Z)-methoxyiminoacetamido]-3-(3-oxobutyryloxymethyl)-3-cephem-4-carboxylic acid In 500 ml of a mixture of tetrahydrofuran-water (1:1) is dissolved 150 g of 7β-2-[2-(chloroacetamidothiazol-4-yl)-2(Z)-methoxyiminoacetamido]-3-(3-oxobutyryloxymethyl)-3-cephem-4-carboxylic acid. To the solution is added 51 g of sodium N-methyldithiocarbamate, and the mixture is stirred at 20° C. for three hours. To the reaction mixture is added 200 ml of ethyl acetate. The organic layer is removed, and the aqueous layer is adjusted to pH 4 with 10% hydrochloric acid to bring about precipitation of an oily substance, which is extracted with one liter of a mixture of tetrahydrofuran-ethyl acetate (1:1). The aqueous layer is further extracted with 200 ml of 1-butanol. The extracts are combined and dried over anhydrous sodium sulfate, and the solvent is evaporated off under reduced pressure. To the residue is added 200 ml of ethyl acetate, and the mixture is stirred. The precipitating crystals are collected by filtration to give 90 g of the above-identified compound.

Elemental analysis for $C_{18}H_{19}N_5O_8S_2$: Calcd. (%): C, 42.19; H, 4.30; N, 13.55. Found (%): C, 41.94; H, 4.11; N, 13.59.

IR Spectrum $\nu_{max}^{KBr}$ cm$^{-1}$: 1770, 1710, 1620, 1520.

NMR spectrum (d$_6$-DMSO)δ: 2.20 (3H, s), 3.43 and 3.65 (2H, ABq, J=18 Hz), 3.63 (2H, s), 3.86 (3H, s), 4.78 and 5.06 (2H, ABq, J=13 Hz), 5.14 (1H, d, J=5 Hz), 5.79 (1H, d. d, J=5 Hz and 8 Hz), 6.73 (1H, s), 7.17 (2H, br.), 9.56 (1H, d, J=8 Hz).

REFERENCE EXAMPLE 3

7β-[2-(2-Aminothiazol-4-yl)-2(Z)-ethoxyiminoacetamido]-3-(3-oxobutyryloxymethyl)-3-cephem-4-carboxylic acid In 100 ml of dimethylformamide is dissolved 23 g of 2-(2-aminothiazol-4-yl)-2(Z)-ethoxyiminoacetic acid. To the solution are added 15 g of 1-hydroxybenzotriazole and 20.6 g of dicyclohexylcarbodiimide, and the mixture is stirred at 20° C. for 1.5 hours. The insolubles are filtered off. The filtrate added, under ice-cooling, to a solution of 31 g of 7β-amino-3-(3-oxobutyryloxymethyl)-3-cephem-4-carboxylic acid and 28 ml of triethylamine in 100 ml of dimethylformamide. The reaction mixture was stirred at 20° C. for three hours. To the mixture is added 500 ml of ether, and resulting precipitates are collected by filtration and then dissolved in 100 ml of water. The resulting aqueous solution is adjusted to pH 3.0 with 10% hydrochloric acid and extracted twice with 200 ml portions of methyl ethyl ketone. The extract is washed with water and dried over anhydrous sodium sulfate. The solvent is evaporated under reduced pressure to leave a solid which is washed with ethyl acetate to give 31 g of the above-identified compound.

IR spectrum $\nu_{max}^{KBr}$ cm$^{-1}$: 1780, 1720, 1660.

NMR spectrum (d$_6$-DMSO)δ: 1.30 (3H, t, J=7.5 Hz), 2.25 (3H, s), 3.45–3.65 (4H, m), 4.20 (2H, q, J=7.5 Hz), 4.70 & 5.10 (2H, ABq, J=18 Hz), 5.25 (2H, d, J=5 Hz), 5.90 (1H, d. d, J=5 Hz & 8 Hz), 6.90 (1H, s), 7.20–7.80 (2H, br.), 9.80 (1H, d, J=7.5 Hz).

REFERENCE EXAMPLE 4

7β-[2-(2-Aminothiazol-4-yl)-2(Z)-allyloxyiminoacetamide]-3-(3-oxobutylyloxymethyl)-3-cephem-4-carboxylic acid In 50 ml of dimethylformamide is dissolved 13 g of 2-(2-aminothiazol-4-yl)-2(Z)-allyloxyiminoacetic acid. To the solution are added 8 g of 1-hydroxybenzotriazole and 10.3 g of dicyclohexylcarbodiimide, and the mixture is stirred at 20° C. for three hours. Insoluble substance is removed by filtration, and the filtrate is added, under ice-cooling, to 50 ml of dimethylformamide in which is dissolved 16 g of 7β-amino-3-(3-oxobutyryloxymethyl)-3-cephem-4-carboxylic acid and 10 g of triethylamine. The reaction mixture is stirred at 20° C. for three hours, to which is added 500 ml of diethyl ether, followed by removal of the ether layer to leave insoluble substance. The insoluble substance is dissolved in 50 ml of water, and the aqueous solution is adjusted to pH 3.0 to give the titled compound in crude state, which is dissolved in 500 ml of a mixture of ethyl acetate and tetrahydrofuran (1:1), dried over anhydrous magnesium sulfate, treated with activated carbon, followed by removal of the solvent by evaporation under reduced pressure to leave 25 g of the titled compound as amorphous powder.

IR spectrum $\nu_{max}^{KBr}$ cm$^{-1}$: 1780, 1720, 1660, 1620.

NMR spectrum (d$_6$-DMSO)δ: 2.30 (3H, s), 3.45–3.66 (4H, m), 4.64 (2H, d, J=6 Hz), 4.80–5.10 (2H, ABq, J=18 Hz), 5.23 (2H, d, J=9 Hz), 5.26 (2H, d, J=5 Hz), 5.90 (1H, d. d, J=5 Hz & 9 Hz), 5.90–6.20 (1H, m), 6.80 (1H, s), 7.20–8.00 (2H, br.), 9.83 (1H, d, J=9 Hz).

REFERENCE EXAMPLE 5

7β-[2-(2-Aminothiazol-4-yl)-2(Z)-(tert-butoxycarbonylmethoxyimino)acetamido]-3-(3-oxobutyryloxymethyl)-3-cephem-4-carboxylic acid In 20 ml of dimethylformamide is dissolved 6.0 g of 2-(2-aminothiazol-4-yl)-2-(Z)-tert-butoxycarbonylmethoxyiminoacetic acid. To the solution are added 3.5 g of 1-hydroxybenzotriazole and 4.4 g of dicyclohexylcarbodiimide, and the mixture is stirred at 20° C. for three hours. Insoluble substance is removed by filtration, and the filtrate is added, under ice-cooling, to 20 ml of dimethylformamide dissolving 6.2 g of 7β-amino-3-(3-oxobutyryloxymethyl)-3-cephem-4-carboxylic acid and 4.0 g of triethylamine. The reaction solution is stirred at 20° C. for eight hours. To 200 ml of diethyl ether is added the reaction mixture and the ether layer is removed. The residue is dissolved in 50 ml of water. The aqueous solution is adjusted to pH 4 with 10% hydrochloric acid to cause precipitation of crystals. The crystals are collected by filtration, washed with water then with diethyl ether, followed by drying to give 10 g of the titled compound.

IR spectrum $\nu_{max}^{KBr}$ cm$^{-1}$: 1790, 1730, 1710, 1660, 1530.

NMR spectrum (d$_6$-DMSO)δ: 1.50 (9H, s), 2.20 (3H, s), 3.40–3.60 (4H, m), 4.40 (2H, s), 4.80 & 5.10 (2H, ABq, J=14 Hz), 5.20 (1H, d, J=5 Hz), 5.80 (1H, d. d, J=5 Hz & 8 Hz), 6.70 (1H, s), 7.20–7.80 (2H, br.), 9.30 (1H, d, J=8 Hz).

REFERENCE EXAMPLE 6

7β-[2-(2-Aminothiazol-4-yl)-2(Z)-(1-tert-butoxycarbonyl-1-methylethoxyimino)acetamido]-3-(3-oxobutyryloxymethyl)-3-cephem-4-carboxylic acid In 60 ml of N,N-dimethylformamide is dissolved 12 g of 2-(2-aminothiazol-4-yl)-2(Z)-(1-tert-butoxycarbonylethoxyimino)acetic acid. To the solution are added 5.86 g of 1-hydroxybenzotriazole and 7.5 g of dicyclohexylcarbodiimide, and the mixture is stirred at room temperature for 30 min. Insoluble substance is filtered off and the filtrate is added to a suspension of 11 g of 7β-amino-3-(3-oxobutyryloxymethyl)-3-cephem-4-carboxylic acid and 10 ml of triethylamine in 30 ml of dimethylformamide. The mixture is stirred at room temperature for 6 hours. Insoluble substance is removed by filtration and 1.3 l of diethyl ether is added to the filtrate. After stirring the ether layer is removed and the residue is dissolved in water. The mixture is adjusted to pH 3–4 with 1N HCl and extracted with 1 l of methyl ethyl ketone. The organic layer is washed with saturated aqueous sodium chloride solution and dried over anhydrous magnesium sulfate. The solvent is then evaporated off under reduced pressure. The residue solidifies on addition of hexane. The powder obtained is collected by filtration to give 18.7 g of the above-identified compound.

IR Spectrum $\nu_{max}^{KBr}$ cm$^{-1}$: 1780, 1720, 1660, 1530.

NMR Spectrum (d$_6$-DMSO)δ: 1.42 (15H, s), 2.20 (3H, s), 3.4–3.7 (4H, m), 4.70 and 5.10 (2H, ABq, J=14 Hz), 5.19 (1H, d, J=4.5 Hz), 52.8 (1H, d. d, J32 4.5 Hz and 8 Hz), 6.73 (1H, s), 7.19 (2H, br. s), 9.29 (1H, d, J=8 Hz).

REFERENCE EXAMPLE 7

7β-[2-(5-tert-Butoxycarbonylamino-1,2,4-thiadiazol-3-yl)-2(Z)-methoxyiminoacetamido]-3-(3-oxobutyryloxymethyl)-3-cephem-4-carboxylic acid To 4 ml of dichloromethane is added 302 g of 2-(5-tert-butoxycarbonylamino-1,2,4-thiadiazol-3-yl)-2(Z)-methoxyiminoacetic acid, followed by addition of 208 mg of phosphorus pentachloride. The mixture is stirred with ice-cooling for 15 minutes. The solvent is then evaporated off under reduced pressure and hexane is added to the residue. The mixture is evaporated to dryness under reduced pressure and the residue is dissolved in dichloromethane. The resulting solution is added to a solution of 300 mg of 7β-amino-3-(3-oxobutyloxymethyl)-3-cephem-4-carboxylic acid and 0.6 ml of triethylamine in 5 ml of dimethylacetamide, and the mixture is stirred with ice-cooling for 30 minutes. To the reaction mixture is added a solution of 1 g of phosphoric acid in 10 ml of water and the resulting mixture is extracted with methyl ethyl ketone (10 ml). The extract is washed with water and dried over magnesium sulfate. The solvent is then evaporated off under reduced pressure. Ethyl acetate is added to the residue and the solvent is evaporated again to give 390 mg of the above-identified compound.

IR spectrum $\nu_{max}^{KBr}$ cm$^{-1}$: 2980, 2940, 1780, 1715, 1540, 1370, 1245, 1150, 1040, 855.

NMR spectrum (d$_6$-DMSO)δ: 1.56 (9H, s), 2.20 (3H, s), 3.43 and 3.70 (2H, ABq, J=18 Hz), 3.65 (2H, s), 4.00 (3H, s), 4.80 and 5.12 (2H, ABq, J=12 Hz), 5.18 (1H, d, J=4.5 Hz), 5.88 (1H, d. d, J=9 Hz and 4.5 Hz), 9.63 (1H, d, J=9 Hz).

REFERENCE EXAMPLE 8

7β-[2-(5-Amino-1,2,4-thiadiazol-3-yl)-2(Z)-ethoxyiminoacetamido]-3-(3-oxobutyryloxymethyl)-3-cephem-4-carboxylic acid In 200 ml of dichloromethane is suspended 11 g of 7β-amino-3-(3-oxobutyryloxymethyl)-3-cephem-4-carboxylic acid. To the suspension is added 14 g of bis-trimethylsilylacetamide and the mixture is stirred at room temperature until complete dissolution and cooled in an ice-water bath. To this solution, 14 g of 2-(5-amino-1,2,4-thiadiazol-3-yl)-2(Z)-ethoxyiminoacetyl chloride is added and the mixture is stirred for a while, to which 6 g of dimethylacetamide is added. The whole mixture is stirred with ice-cooling for 60 minutes. The dichloromethane is evaporated off and the residue is dissolved in methyl ethyl ketone. The solution is washed with water and dried. The solvent is then evaporated off and diethyl ether is added to the residue to give a fine precipitate, which is collected by filtration, giving 12.5 g of the above-identified compound.

IR spectrum $\nu_{max}^{KBr}$ cm$^{-1}$: 3300, 3000, 1780, 1720, 1620, 1520, 1410, 1260, 1150, 1040.

NMR spectrum (d$_6$-DMSO)δ: 1.25 (3H, t, J=7 Hz), 2.18 (3H, s), 3.41 and 3.63 (2H, ABq, J=18 Hz), 3.62 (2H, s), 4.18 (2H, q, J=7 Hz), 4.76 and 5.06 (2H, ABq, J=13 Hz), 5.14 (1H,d, J=4.8 Hz), 5.82 (1H, d. d, J=8 Hz and 4.8 Hz), 8.00 (2H, br.), 9.48 (1H, d, J=8 Hz).

REFERENCE EXAMPLE 9

7β-Formamido-3-(3-oxobutyryloxymethyl)-3-cephem-4-carboxylic acid

In 60 ml of formic acid is dissolved 3.2 g of 7β-amino-3-(3-oxobutyryloxymethyl)-3-cephem-4-carboxylic acid and the solution is cooled to 0°-5° C. With stirring, 20 ml of acetic anhydride is added dropwise to the solution during 30 minutes. The mixture is stirred at the same temperature for 30 minutes and then at room temperature for 1 hour. The solvent is evaporated off under reduced pressure and the residue is dissolved in methyl ethyl ketone. The solution is washed with water and saturated aqueous sodium chloride solution and dried over anhydrous magnesium sulfate. The solvent is then evaporated off under reduced pressure and a diisopropylether-hexane mixture is added to the residue to bring about solidification. The solid is then collected by filtration to give 3.1 g of the above-identified compound as a light-yellow powder.

IR spectrum $\nu_{max}^{KBr}$ cm$^{-1}$: 3380, 1780, 1720, 1660, 1625, 1510.

NMR spectrum (d$_6$-DMSO)δ: 2.20 (3H, s), 3.45 and 3.68 (2H, ABq, J=18 Hz), 3.63 (2H, s), 4.79 and 5.09 (2H, ABq, J×13 Hz), 5.11 (1H, d, J=4.5 Hz), 5.79 (1H, d. d, J=4.5 Hz and 8 Hz), 8.15 (1H, br.), 9.00 (1H, d, J=8 Hz).

REFERENCE EXAMPLE 10

7β-[2-(5-Chloro-2-chloroacetamidothiazol-4-yl)-2(Z)-methoxyiminoacetamido]-3-(3-oxobutyryloxymethyl)-3-cephem-4-carboxylic acid To 50 ml of dichloromethane is added 2.39 g of 2-(5-chloro-2-chloroacetamidothiazol-4-yl)-2(Z)-methoxyiminoacetic acid and, while cooling at −5° C. to −8° C., 2.13 g of phosphorus pentachloride is added and the mixture is stirred for 45 minutes. To the reaction mixture is added 150 ml (in 30-ml portions) of hexane, and the dark oily precipitate is separated and washed with hexane to give the corresponding crude chloride. Separately, a solution of 2.06 g of 7β-amino-3-(3-oxobutyryloxymethyl)-3-cephem-4-carboxylic acid in 15 ml of tetrahydrofuran is added to a solution of 2.06 g of sodium hydrogen carbonate in 15 ml of water, and to the resulting mixture, the chloride obtained above is added while maintaining the inside temperature at 0°-3° C. Thereafter, the mixture is stirred at the temperature not exceeding 5° C. for 1 hour and then at room temperature for further 1 hour. Fifty ml of methyl ethyl ketone is added to the reaction mixture and the mixture is acidified with concentrated hydrochloric acid. The organic layer is separated and the aqueous layer is extracted with methyl ethyl ketone. The organic layer and the extract are combined and dried over anhydrous sodium sulfate. The solvent is then evaporated off under reduced pressure to give 2.94 g of the above-identified compound as light-orange powder.

NMR spectrum (CDCl$_3$+d$_6$-DMSO)δ: 2.23 (3H, s), 3.24–3.73 (2H, m), 3.50 (2H, s), 4.01 (3H, s), 4.21 (2H, s), 4.91 and 5.18 (2H, ABq, J=13 Hz), 5.05 (1H, d, J=4.5 Hz), 5.88 (1H, d. d, J=4.5 Hz & 9 Hz), 6.43 (2H, br.), 8.79 (1H, d, J=9 Hz).

REFERENCE EXAMPLE 11

7β-[2-(2-Amino-5-chlorothiazol-4-yl)-2(Z)-methoxyiminoacetamido]-3-(3-oxobutyryloxymethyl)-3-cephem-4-carboxylic acid To a mixture of 13 ml of water and 13 ml of tetrahydrofuran is dissolved 2.94 g of 7β-[2-(5-chloro-2-chloroacetamidothiazol-4-yl)-2(Z)-methoxyiminoacetamido]-3-(3-oxobutyryloxymetyl)-3-cephem-4-carboxylic acid. To the mixture is added 1.15 g of sodium N-methyldithiocarbamate in 3 portions with stirring at room temperature for 3 hours. Ethyl acetate is added to the reaction mixture and the ethyl acetate layer is separated and discarded. The aqueous layer is acidified with concentrated hydrochloric acid and extracted with 200 ml of methyl ethyl ketone. The extract is washed with aqueous sodium chloride solution and dried over anhydrous sodium sulfate. The solvent is then evaporated off to give 2.28 g of the above-identified compound.

NMR spectrum (d$_6$-DMSO+CDCl$_3$)δ: 2.21 (3H, s), 3.3–3.75 (2H, m), 3.57 (2H, s), 3.90 (2H, s), 4.81 and 5.09 (2H, ABq, J=13 Hz), 5.07 (1H, d, J=5 Hz), 5.77 (1H, d. d, J=5 Hz & 9 Hz), 7.10 (2H, br.), 9.46 (1H, d, J=9 Hz).

REFERENCE EXAMPLE 12

7β-[2-(2-Amino-5-chlorothiazol-4-yl)-2(Z)-ethoxyiminoacetamido]-3-(3-oxobutyryloxymethyl)-3-cephem-4-carboxylic acid Starting from 2-(5-chloro-2-chloroacetamidothiazol-4-yl)-2(Z)-ethoxyiminoacetic acid, the above-identified compound is obtained in the manner of Reference Examples 10 and 11.

IR Spectrum $\nu_{max}^{KBr}$ cm$^{-1}$: 3300, 1770, 1700, 1620, 1530.

NMR Spectrum(d$_6$-DMSO)δ: 1.27(3H, t, J=7 Hz), 2.20(3H, s), 3.3~3.8(2H, m), 3.62(2H, s), 4.17(2H, q, J=7 Hz), 4.83 and 5.09(2H, ABq, J=12 Hz), 5.13(1H, d, J=5 Hz), 5.81(1H, d. d, J=5 Hz and 8 Hz), 6.63 (1H, br. s), 7.24(2H, br. s), 9.50(1H, d, J=8 Hz).

EXAMPLE 1

7β-[2-(2-Aminothiazol-4-yl)-2(Z)-methoxyiminoacetamido]-3-[(pyrazolo[1,5-a]pyridinium-3-yl)methyl]-3-cephem-4-carboxylate

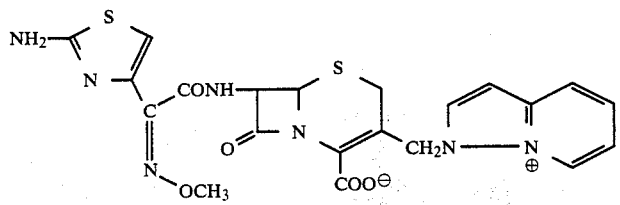

In 30 ml of a 1:1 mixture of acetonitrile and water are dissolved 2.0 g of 7β-[2-(2-aminothiazol-4-yl)-2(Z)-methoxyiminoacetamido]-3-(3-oxobutyryloxymethyl)-3-cephem-4-carboxylic acid, 2.0 g of pyrazolo[1,5-a]pyridine and 2.0 g of potassium iodide, and the mixture is stirred at 70° C. for 1.5 hours. The mixture is concentrated under reduced pressure. The residue is washed with 30 ml of ethyl acetate and subjected to silica gel column chromatography using a mixture of acetonitrile and water (4:1) as an eluent. The eluted fractions containing the objective compound are collected and concentrated under reduced pressure. The residue obtained is chromatographed on an XAD-2 column using 20% aqueous ethanol as an eluent. The fractions containing the objective compound are combined and concentrated under reduced pressure, and the residue is lyophilized to give 0.11 g of the above-identified compound.

Elemental analysis for: C$_{21}$H$_{19}$N$_7$O$_5$S$_2$.11/2H$_2$O: Calcd.(%): C, 41.17; H, 4.94; N, 16.00. Found (%): C, 41.23; H, 4.25; N, 16.38.

IR spectrum $\nu_{max}^{KBr}$ cm$^{-1}$: 1775, 1675, 1620, 1530.

NMR spectrum (d$_6$-DMSO)δ: 3.80 (3H, s), 5.05 (1H, d, J=4.5 Hz), 5.07 & 5.35 (2H, ABq, J=13 Hz), 5.68 (1H, d. d, J=4.5 Hz & 8 Hz), 6.67 (1H, s), 7.14 (2H, br. s), 7.5–8.2 (3H, m), 8.12–8.34 (1H, m), 8.58–8.71 (1H, m), 8.77–8.95 (1H, m), 9.47 (1H, d, J=8 Hz).

7β-[2-(2-Aminothiazol-4-yl)-2(Z)-(substituted oxyimino)acetamido]-3-(3-oxobutyryloxymethyl)-3-cephem-4-carboxylic acid is reacted with various pyrazole compounds in the same manner as described in Example 1 to give the compounds of Examples 2-4, which have the following general formula:

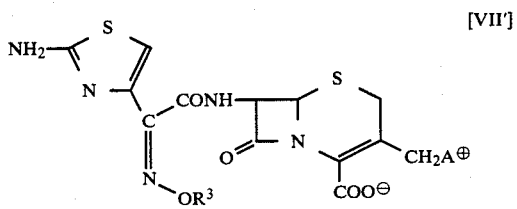

EXAMPLE 2

7β-[2-(2-Aminothiazol-4-yl)-2(Z)-ethoxyiminoacetamido]-3-[(pyrazolo[1,5-a]pyridinium-3-yl)methyl]-3-cephem-4-carboxylate Compound [VII']

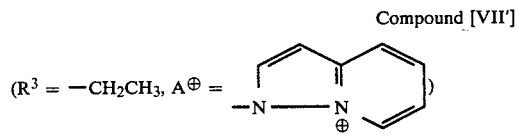

Elemental analysis for: C$_{22}$H$_{21}$N$_7$O$_5$S$_2$.9/2H$_2$O: Calcd.(%): C, 43.42; H, 4.97; N, 16.11. Found (%): C, 43.21; H, 5.26; N, 16.09.

IR spectrum $\nu_{max}^{KBr}$ cm$^{-1}$: 1765, 1670, 1615, 1525.

NMR spectrum (d$_6$-DMSO) δ: 1.24 (3H, t, J=7 Hz), 4.11 (2H, q, J=7 Hz), 5.05 (1H, d, J=4.5 Hz), 4.90 & 5.12 (2H, ABq, J=13 Hz), 5.52–5.76 (1H, m), 6.72 (1H, s), 7.14 (2H, br. s), 7.58–8.00 (3H, m), 8.12–8.30 (1H, m), 8.54–8.73 (1H, m), 8.8–8.98 (1H, m), 9.40 (1H, d, J=8 Hz).

EXAMPLE 3

7β-[2-(2-Aminothiazol-4-yl-2(Z)-allyloxyiminoacetamido]-3-[(pyrazolo[1,5-a]pyridinium-3-yl)methyl]-3-cephem-4-carboxylate Compound [VII']

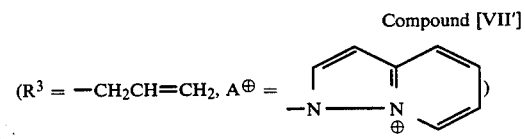

Elemental analysis for: C$_{23}$H$_{21}$N$_7$O$_5$S$_2$.13/2H$_2$O: Calcd.(%): C, 42.06; H, 5.22; N, 14.93. Found (%): C, 42.29; H, 5.24; N, 14.51.

IR spectrum $\nu_{max}^{KBr}$ cm$^{-1}$: 1770, 1670, 1630, 1615, 1525, 1020.

NMR spectrum (d$_6$-DMSO) δ: 4.46–4.68 (2H, m), 5.02 (1H, d, J=4.5 Hz), 5.24 (2H, br. s), 5.38 (2H, br. s), 5.63 (1H, d. d, J=4.8 Hz & 8 Hz), 5.76–6.20 (1H, m), 6.84 (1H, s), 7.14 (1H, br. s), 7.5–8.0 (3H, m), 8.1–8.28 (1H, m), 8.58–8.70 (1H, m), 8.8–8.9 (1H, m), 9.48 (1H, d, J=8 Hz).

EXAMPLE 4

7β-[2-(2-Aminothiazol-4-yl)-2(Z)-(2-fluoroethoxyimino)acetamido]-3-[(pyrazolo[1,5-a]pyridinium-3-yl)methyl]-3-cephem-4-carboxylate

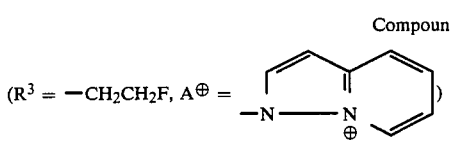

Elemental analysis for: C$_{22}$H$_{20}$N$_7$O$_5$S$_2$F.4H$_2$O: Calcd.(%): C, 42.78; H, 4.57; N, 15.87. Found (%): C, 42.50; H, 4.66; N, 15.73.

IR spectrum $\nu_{max}^{KBr}$ cm$^{-1}$: 1760, 1665, 1610, 1530, 1360.

NMR spectrum (d$_6$-DMSO) δ: 4.0–4.23 (1H, m), 4.25–4.53 (2H, m), 4.80–5.00 (1H, m), 5.03 (1H, d, J=4.5 Hz), 5.65 (d. d, J=4.5 Hz & 8 Hz), 6.70 (1H, s), 7.14–7.40 (2H, br. s), 7.50–8.0(m, 3H), 8.1–8.30 (1H, m), 8.50–9.00 (2H, m), 9.50 (1H, d, J=8 Hz).

EXAMPLE 5

7β-[2-(2-Aminothiazol-4-yl)-2(Z)-methoxyiminoacetamido]-3-[(7-methylpyrazolo[1,5-a]pyridinium-3-yl)methyl]-3-cephem-4-carboxylate

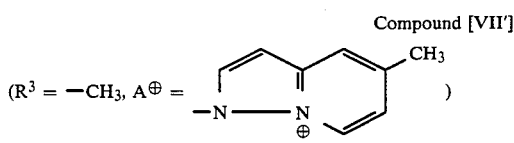

In 30 ml of a 1:1 mixture of acetonitrile and water are dissolved 2 g of 7β-[2-(2-Aminothiazol-4-yl)-2(Z)methoxyiminoacetamido]-3-(3-oxobutyryloxymethyl)-3-cephem-4-carboxylic acid, 2 g of 7-methylpyrazolo[1,5-a]pyridine and 2 g of potassium iodide, and the mixture is stirred at 60°–70° C. for 2 hours. After cooling, the mixture is subjected to silica gel column chromatography using acetone and a mixture of acetone and water, successively, as an eluent. The fractions containing the objective compound are combined and concentrated under reduced pressure. The residual aqueous solution is chromatographed on a column of MCI GEL CHP20P (150–300 meshes; Mitsubishi Chemical Industries, Ltd., Japan) using aqueous ethanol as an eluent. The water-ethanol (80:20)-eluted fractions are combined and concentrated under reduced pressure. The residue is lyophilized to give 0.11 g of the above-identified compound.

Elemental analysis for: C$_{22}$H$_{21}$N$_7$O$_5$S$_2$.3H$_2$O: Calcd.(%): C, 45.43; H, 4.68; N, 16.86. Found (%): C, 45.10; H, 3.93; N, 16.43.

IR spectrum $\nu_{max}^{KBr}$ cm$^{-1}$: 1770, 1680, 1610, 1530.

NMR spectrum(D$_2$O)δ: 2.52(3H, s), 3.01 and 3.47(2H, ABq, J=18 Hz), 3.96(3H, s), 5.24(1H, d, J=4.5 Hz), 5.62(2H, br. s), 5.81(1H, d, J=4.5 Hz), 6.81(1H, s), 6.99(1H, d, J=3.5 Hz), 7.3–7.54(1H, m), 7.82(1H, br. s), 8.40(1H, d, J=3.5 Hz), 9.05(1H, d, J=8 Hz).

7β-[2-(2-Aminothiazol-4-yl)-2(Z)-(substituted oxyimino)acetamido]-3-(3-oxobutyryloxymethyl)-3-cephem-4-carboxylic acid is reacted with various pyrazole compounds in the same manner as described in Example 5 to give the compounds [VII'] (Examples 6–9 and 16).

EXAMPLE 6

7β-[2-(2-Aminothiazol-4-yl)-2(Z)-ethoxyiminoacetamido]3-[(7-methylpyrazolo[1,5-a]pyridinium-3-yl)methyl]-3-cephem-4-carboxylate

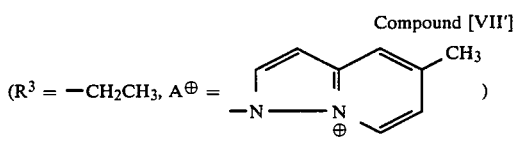

Elemental analysis for: C$_{23}$H$_{23}$N$_7$O$_5$S$_2$.9/2H$_2$O: Calcd.(%): C, 44.37; H, 5.18; N, 15.75. Found (%): C, 44.54; H, 4.83; N, 15.52.

IR spectrum $\nu_{max}^{KBr}$ cm$^{-1}$: 1770, 1665, 1610, 1525.

NMR spectrum (D$_2$O)δ: 1.27(3H, t, J=7 Hz), 2.52(3H, s), 3.04 and 3.48(2H, ABq, J=18 Hz), 4.23(2H, ABq, J=7 Hz), 5.25(1H, d, J=4.5 Hz), 5.62(2H, br. s), 5.82(1H, d, J=4.5 Hz), 6.87(1H, s), 7.02(1H, d, J=3 Hz), 7.3–7.52(1H, m), 7.74–7.96(1H, m), 8.40(1H, d, J=4 Hz), 9.04(1H, d, J=7 Hz).

EXAMPLE 7

7β-[2-(2-Aminothiazol-4-yl)-2(Z)-methoxyiminoacetamido]-3-[(2-methylpyrazolo[1,5-a]pyridinium-3-yl)methyl]-3-cephem-4-carboxylate

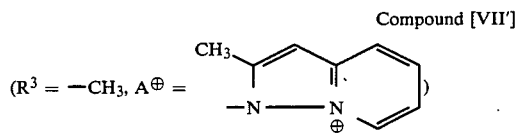

Elemental analysis for C$_{22}$H$_{21}$N$_7$O$_5$S$_2$.4H$_2$O: Calcd. (%): C, 44.07; H, 4.87; N, 16.35. Found (%): C, 44.11; H, 4.07; N, 16.22.

IR spectrum $\nu_{max}^{KBr}$ cm$^{-1}$: 1760, 1660, 1610, 1535.

NMR spectrum (D$_2$O) δ: 2.71 (3H, s), 2.87 and 3.41 (2H, ABq, J=18 Hz), 3.96 (3H, s), 5.20 (1H, d, J=5 Hz), 5.55–5.74 (2H, m), 5.80 (1H, d, J=5 Hz), 6.88 (1H, s), 6.98 (1H, s), 7.40–7.66 (1H, m), 7.68–8.08 (2H, m), 9.19 (1H, d, J=7 Hz).

EXAMPLE 8

7β-[2-(2-Aminothiazol-4-yl)-2(Z)-methoxyiminoacetamido]-3-[(6,8-dimethylpyrazolo[1,5-a]pyridinium-3-yl)methyl]-3-cephem-4-carboxylate

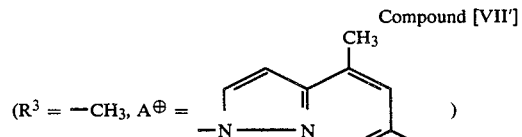

Elemental analysis for C$_{23}$H$_{23}$N$_7$O$_5$S$_2$.7/2H$_2$O: Calcd. (%): C, 45.69; H, 5.00; N, 16.22. Found (%): C, 45.44; H, 4.16; N, 16.05.

IR spectrum $\nu_{max}^{KBr}$ cm$^{-1}$: 1775, 1670, 1615, 1530.

NMR spectrum (D₂O) δ: 2.46 (3H, s), 2.58 (3H, s), 3.06 and 3.47 (2H, ABq, J=18 Hz), 3.98 (3H, s), 5.22 (1H, d, J=4.5 Hz), 5.59 (2H, s), 5.79 (1H, d, J=4.5 Hz), 6.87 (1H, s), 7.12 (1H, d, J=4 Hz), 7.53 (1H, br. s), 8.36 (1H, d, J=4 Hz), 8.82 (1H, br. s).

EXAMPLE 9

7β-[2-(2-Aminothiazol-4-yl)-2(Z)-(2-methoxyethoxyimino)acetamido]-3-[(7-methylpyrazolo[1,5-a]pyridinium-3-yl)methyl]-3-cephem-4-carboxylate Compound [VII']

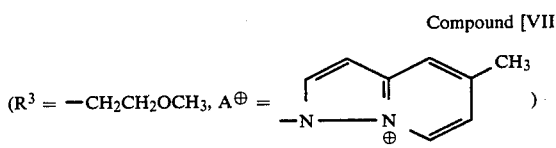

(R³ = —CH₂CH₂OCH₃, A⊕ = )

Elemental analysis for C₂₄H₂₅N₇O₆S₂.9/2H₂O: Calcd. (%): C, 44.17; H, 5.25; N, 15.02. Found (%): C, 44.12; H, 5.00; N, 15.16.

IR spectrum ν$_{max}^{KBr}$ cm⁻¹: 1770, 1670, 1620, 1530.

NMR spectrum (D₂O) δ: 2.54 (3H, s), 2.99 and 3.46 (2H, ABq, J=18 Hz), 3.31 (3H, s), 3.65–3.83 (2H, m), 4.24–4.46 (2H, m), 5.24 (1H, d, J=5 Hz), 5.54–5.74 (2H, m), 5.81 (1H, d, J=5 Hz), 6.89 (1H, s), 7.01 (1H, d, J=4 Hz), 7.31–7.5 (1H, m), 7.83 (1H, br. s), 8.39 (1H, d, J=4 Hz), 9.06 (1H, d, J=7 Hz).

7β-[2-(5-Amino-1,2,4-thiadiazol-3-yl)-2(Z)-(substituted oxyimino)acetamido]-3-(3-oxobutyryloxymethyl)-3-cephem-4-carboxylic acid is reacted with various pyrazole compounds in the same manner as described in Example 5 to give the compounds of Examples 10–12, which have the following general formula:

[VIII']

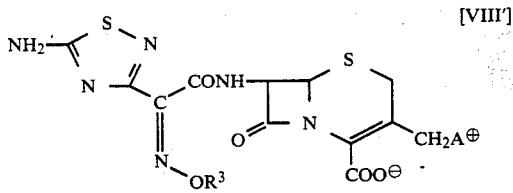

EXAMPLE 10

7β-[2-(5-Amino-1,2,4-thiadiazol-3-yl)-2(Z)-methoxyiminoacetamido]-3-[(pyrazolo[1,5-a]pyridinium-3-yl)methyl]-3-cephem-4-carboxylate Compound [VIII']

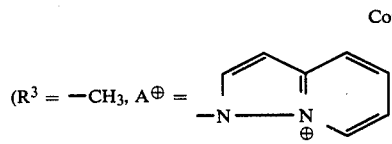

(R³ = —CH₃, A⊕ = )

Elemental analysis for: C₂₀H₁₈N₈O₅S₂.7/2H₂O: Calcd.(%): C, 41.59; H, 4.36; N, 19.40. Found(%): C, 41.90; H, 4.61; N, 19.48.

IR spectrum ν$_{max}^{KBr}$ cm⁻¹: 1770, 1670, 1620, 1520.

EXAMPLE 11

7β-[2-(5-Amino-1,2,4-thiadiazol-3-yl)-2(Z)ethoxyiminoacetamido]-3-[(pyrazolo[1,5-a]pyridinium-3-yl)methyl]-3-cephem-4-carboxylate Compound [VIII']

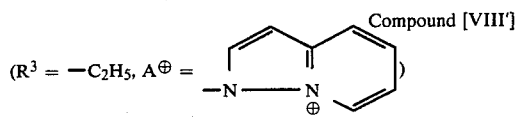

(R³ = —C₂H₅, A⊕ = )

Elemental analysis for: C₂₁H₂₀N₈O₅S₂.4H₂O: Calcd.(%): C, 41.99; H, 4.70; N, 18.66. Found (%): C, 42.36; H, 4.64; N, 18.20.

IR spectrum ν$_{max}^{KBr}$ cm⁻¹: 1770, 1670, 1630, 1610, 1510.

NMR spectrum (D₂O)δ: 1.22(3H, t, J=7 Hz), 3.07 and 3.48(2H, ABq, J=18 Hz), 4.31(2H, q, J=7 Hz), 5.24(1H, d, J=4.5 Hz), 5.65(2H, br. s), 5.85(1H, d, J=4.5 Hz), 7.71(1H, d, J=4 Hz), 7.48–7.72(1H, m), 7.74–8.00(1H, m), 8.02–8.2(1H, m), 8.44(1H, d, J=4 Hz), 9.17(1H, d, J=7 Hz).

EXAMPLE 12

7β-[2-(5-Amino-1,2,4-thiadiazol-3-yl)-2(Z)methoxyiminoacetamido]-3-[(7-methylpyrazolo[1,5-a]pyridinium-3-yl)methyl]-3-cephem-4-carboxylate Compound [VIII']

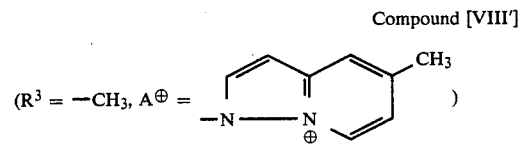

(R³ = —CH₃, A⊕ = )

Elemental analysis for C₂₁H₂₀N₈O₅S₂.7H₂O: Calcd. (%): C, 38.52; H, 5.23; N, 17.12. Found (%): C, 38.57; H, 5.60; N, 17.35.

IR spectrum ν$_{max}^{KBr}$ cm⁻¹: 1765, 1760, 1670, 1670, 1610, 1520.

NMR spectrum (D₂O) δ: 2.54 (3H, s), 3.05 and 3.48 (2H, ABq, J=18 Hz), 4.06 (3H, s), 5.05 (1H, d, J=4.5 Hz), 5.60 (2H, s), 5.86 (1H, d, J=4.5 Hz), 6.94–7.1 (1H, m), 7.28–7.52 (1H, m), 7.74–7.92 (1H, m), 8.29–8.44 (1H, m), 8.9–9.12 (1H, m).

EXAMPLE 13

7β-Formamido-3-[(pyrazolo[1,5-a]pyridinium-3-yl)methyl]-3-cephem-4-carboxylate

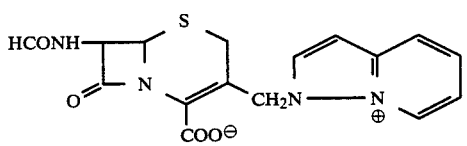

7β-Formamido-3-(3-oxobutyryloxymethyl)-3-cephem-4-carboxylic acid and pyrazolo[1,5-a]pyridine are reacted in the same manner as described in Example 5 to give the above-identified compound.

Elemental analysis for: C₁₆H₁₄N₄O₄S.7H₂O: Calcd.(%): C, 39.64; H, 5.83; N, 11.56. Found (%): C, 39.50; H, 5.46; N, 11.61.

IR spectrum ν$_{max}^{KBr}$ cm⁻¹: 1760, 1670, 1600, 1500.

NMR spectrum (d₆-DMSO)δ: 3.39(2H×½, ABq×½, J=18 Hz), 5.01(1H, d, J=4.5 Hz), 5.44–5.99(3H, m), 6.59(1H, d, J=2 Hz), 6.74–6.98(1H, m), 7.08–7.40(1H, m), 7.56–7.76(1H, m), 7.97(1H, d, J=2 Hz), 8.00–8.22(2H, m), 8.64(1H, d, J=7 Hz), 8.86(1H, d, J=7 Hz), 8.86(1H, d, J=8 Hz).

EXAMPLE 14

7β-Amino-3-[(pyrazolo[1,5-a]pyridinium-3-yl)methyl]-3-cephem-4-carboxylate hydrochloride

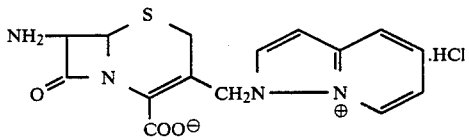

In 10 ml of methanol is suspended 1.0 g of 7β-formamido-3-[(pyrazolo[1,5-a]pyridinium-3-yl)methyl]-3-cephem-4-carboxylate and the suspension is cooled under 5° C. To the suspension is added dropwise 1.0 ml of concentrated hydrochloric acid with stirring and the mixture is stirred at the same temperature for 10 minutes and then at room temperature for 3 hours. The solvent is evaporated off under reduced pressure and 10 ml of water is added to the residue. The resulting solution is subjected to chromatography on a column of MCI GEL CHP20P (150–300 meshes, Mitsubishi Chemical Industries, Ltd.). The fractions eluted with aqueous ethanol are combined and concentrated under reduced pressure. The residue is lyophilized to give 0.25 g of the above-identified compound as a powder.

Elemental analysis for: $C_{15}H_{14}N_4O_3 \cdot HCl \cdot 2H_2O$: Calcd.(%): C, 44.72; H, 4.75; N, 13.91. Found (%): C, 45.23; H, 4.21; N, 13.17.

IR spectrum $\nu_{max}^{KBr}$ cm$^{-1}$: 1775(sh), 1760, 1630(sh), 1610, 1505.

NMR spectrum (D$_2$O)δ: 3.13 and 3.51(2H, ABq, J=17 Hz), 5.02 (1H, d, J=4.5 Hz), 5.19(1H, d, J=4.5 Hz), 5.67(2H, br. s), 7.21(1H, d, J=3 Hz), 7.52–8.30(3H, m), 8.49(1H, d, J=3 Hz), 9.17(1H, d, J=7 Hz).

7β-[2-(2-Amino-5-chlorothiadiazol-4-yl)-2(Z)-(substituted oxyimino)acetamido]-3-(3-oxobutyryloxymethyl)-3-cephem-4-carboxylic acid is reacted with pyrazolo[1,5-a]pyridine in the same manner as described in Example 5 to give the compounds of Examples 15 and 17, which have the following general formula:

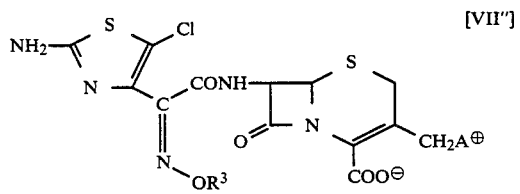

EXAMPLE 15

7β-[2-(5-Amino-5-chlorothiazol-5-yl)-2(Z)-ethoxyiminoacetamido]-3-[(pyrazolo[1,5-a]pyridinium-3-yl)methyl]-3-cephem-4-carboxylate Compound [VII"]

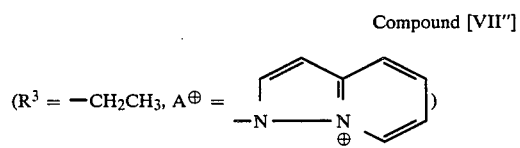

Elemental analysis for: $C_{22}H_{20}N_7O_5S_2Cl \cdot 5/2H_2O$: Calcd. (%): C, 43.53; H, 4.15; N, 16.15. Found (%); C, 43.15; H, 4.36; N, 16.10.

IR spectrum $\nu_{max}^{KBr}$ cm$^{-1}$: 1765, 1670, 1620, 1530, 1510.

NMR spectrum (d$_6$-DMSO)δ: 1.28(3H, t, J=7 Hz), 3.06 and 3.47 (2H, ABq, J=18 Hz), 4.26(2H, q, J=7 Hz), 5.24(1H, d, J=4.5 Hz), 5.67 (2H, br. s), 5.85(1H, d, J=4.5 Hz), 7.18(1H, d, J=4 Hz), 7.48–8.24 (3H, m), 8.49(1H, d, J=4 Hz), 9.18(1H, d, J=7 Hz).

EXAMPLE 16

7β-[2-(2-Aminothiazol-4-yl)-2(Z)-methoxyiminoacetamido]-3-[(1-hydroxypyrazolo[1,5-a]pyridinium-3-yl)methyl]-3-cephem-4-carboxylate Compound [VII']

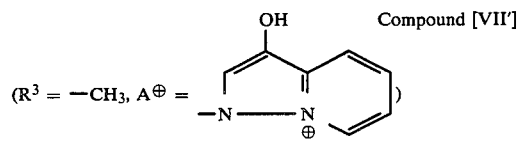

Elemental analysis for: $C_{21}H_{19}N_7O_6S_2 \cdot 15/2H_2O$: Calcd. (%): C, 37.95; H, 5.16; N, 14.75. Found (%): C, 38.24; H, 5.37; N, 14.34.

IR spectrum $\nu_{max}^{KBr}$ cm$^{-1}$: 1760, 1660(sh), 1610, 1520.

NMR spectrum (d$_6$-DMSO)δ: 3.12 and 3.38(2H, ABq, J=18 Hz), 3.68(3H, s), 5.01(1H, d, J=4.5 Hz), 5.2–5.8(3H, m), 6.66(1H, s), 7.25–7.6(3H, m), 7.94–8.18(2H, m), 9.43(1H, d, J=8 Hz), 10.12 (1H, d, J=6 Hz).

EXAMPLE 17

7β-[2-(2-Amino-5-chlorothiazol-4-yl)-2(Z)-methoxyiminoacetamido]-3-[(pyrazolo[1,5-a]pyridinium-3-yl)methyl]-3-cephem-4-carboxylate Compound [VII"]

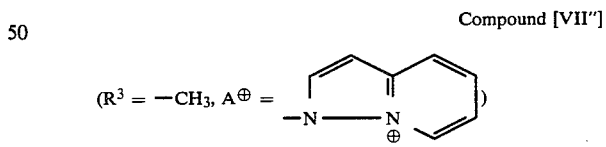

Elemental analysis for: $C_{21}H_{18}N_7O_5S_2Cl \cdot 3H_2O$: Calcd.(%): C, 41.90; H, 4.02; N, 16.29. Found (%): C, 41.45; H, 3.31; N, 15.79.

IR spectrum $\nu_{max}^{KBr}$ cm$^{-1}$: 3390, 1763, 1665, 1610, 1530, 1510, 1017.

NMR spectrum (D$_2$O)δ: 3.23 and 3.64(2H, ABq, J=18 Hz), 4.12 (3H, s), 5.37(1H, d, J=4.5 Hz), 5.81(2H, br. s), 6.00(1H, d, J=4.5 Hz), 7.34(1H, d, J=3 Hz), 7.63–8.39(3H, m), 8.63(1H, d, J=3 Hz), 9.31 (1H, d, J=7 Hz).

EXAMPLE 18

7β-[2-(2-Aminothiazol-4-yl)-2(Z)-(1-carboxy-1-methylethoxyimino)acetamido]-3-[(pyrazolo[1,5-a]pyridinium-3-yl)methyl]-3-cephem-4-carboxylate monosodium salt Compound [VII']

($R^3$ = —C(CH$_3$)$_2$COONa, A$^⊕$ = 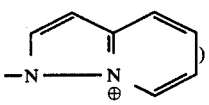)

To 40 ml of a 1:1 mixture of acetonitrile and water are dissolved 3.8 g of 7β-[2-(2-aminothiazol-4-yl)-2(Z)-(1-tert-butoxycarboxyl-1-methylethoxyimino)acetamido]-3-(3-oxobutyryloxymethyl)-3-cephem-4-carboxylic acid, 3.8 g of pyrazolo[1,5-a]pyridine and 3.7 g of potassium iodide and the mixture is stirred at 60° to 70° C. for 2 hours. After cooled, the mixture is subjected to silica gel column chromatography using acetone and aqueous acetone, successively, as an eluent. The acetone-water (80:20 to 70:30)-eluted fractions are combined and concentrated to 10 ml under reduced pressure. The residue is subjected to MCI GEL column chromatography (CHP20P, 150–300 meshes, Mitsubishi Chemical Industries, Ltd.) using water and aqueous ethanol, successively, as an eluent. The water-ethanol (60:40)-eluted fractions are combined, concentrated under reduced pressure and lyophilized. The resulting powder is dissolved in 1 ml of trifluoroacetic acid and stirred at room temperature for 2 hours. The solvent is evaporated off under reduced pressure and water is added to the residue. Sodium carbonate is added to the mixture and the resulting solution is subjected to MCI GEL column chromatography using water and aqueous ethanol, successively, as an eluent. The fractions containing the objective compound are combined and concentrated under reduced pressure. The residue is lyophilized to give 0.03 g of the above-identified compounds.

Elemental analysis for: C$_{24}$H$_{22}$N$_7$O$_7$S$_2$Na.6H$_2$O: Calcd.(%): C, 40.28; H, 4.79; N, 13.70. Found(%): C, 40.43; H, 4.81; N, 13.46.

IR spectrum $\nu_{max}^{KBr}$ cm$^{-1}$: 1775, 1665(sh), 1610, 1540.

NMR spectrum (D$_2$O)δ: 1.47(6H. s), 3.06 and 3.52(2H, ABq, J=18 Hz), 5.25(1H, d, J=4.5 Hz), 5.66(2H, br. s), 5.84(1H, d, J=4.5 Hz), 7.16–7.28(1H, m), 7.54–7.76(1H, m), 7.80–8.20(2H, m), 8.4–8.68 (1H, m), 9.08–9.26(1H, m).

EXAMPLE 19

7β-[2-Aminothiazol-4-yl)-2(Z)-methoxyiminoacetamido]-3-[(7l-carboxypyrazolo[1,5-a]pyridinium-3-yl)methyl]-3-cephem-4-carboxylate monosodium salt Compound [VII']

($R^3$ = CH$_3$, A$^⊕$ = 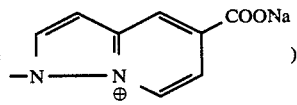)

7β-[2-(2-Aminothiazol-4-yl)-2(Z)-methoxyiminoacetamido]-3-(3-oxobutyxyloxymethyl)-3-cephem-4-carboxylic acid and 7-carboxypyrazolo[1,5-a]pyridine are made to react in the same manner as described in Example 5 with admixture of sodium bicarbonate to give the above-identified compound.

Elemental analysis for C$_{22}$H$_{18}$N$_7$O$_7$S$_2$Na.4H$_2$O: Calcd. (%): C, 40.55; H, 4.02; N, 15.05. Found (%): C, 40.88; H, 4.43; N, 14.67.

IR spectrum $\nu_{max}^{KBr}$ cm$^{-1}$: 1760, 1610, 1530.

NMR (D$_2$O)δ: 3.60(2H, br. s), 4.01(3H, s), 5.26(1H, d, J=4.5 Hz), 5.6–5.9(2H, m) 6.94–7.05 (1H, m), 7.48–7.68(1H, m), 7.85–8.00 (1H, m), 8.50(1H, d, J=6 Hz), 9.16(1H, d, J=8 Hz)

EXAMPLE 20

Five gram of 7β-[2-(2-aminothiazol-4-yl)-2(Z)-methoxyiminoacetamido]-3-[(pyrazolo[1,5-a]pyridinium-3-yl)methyl]-3-cephem-4-carboxylate is dissolved in 50 ml of physiological saline under mixing to produce a composition for injection.

What we claim is:

1. A compound of the formula:

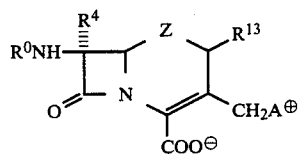

wherein R$^o$ stands for an acyl group of the formula

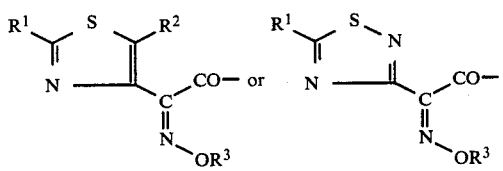

wherein R$^1$ stands for amino or protected amino group; R$^2$ stands for hydrogen atom, halogen atom or nitro group; R$^3$ stands for (i) straight-chain C$_{1-3}$ alkyl group, (ii) straight-chain or branched C$_{1-3}$ alkyl group substituted with halogen atom, hydroxyl group, C$_{1-6}$ alkoxy group, carboxyl group, C$_{1-6}$ alkoxycarbonyl group or cyano group, (iii) allyl group or (iv) propargyl group; Z stands for S; R$^4$ stands for hydrogen atom; R$^{13}$ stands for hydrogen atom; and A stands for pyrazolo[1,5-a]pyridinium-3-yl group which can be substituted with hydroxyl group, C$_{1-6}$ alkyl group or carboxyl group, or a physiologically or pharmaceutically acceptable salt or ester thereof.

2. A compound of the formula

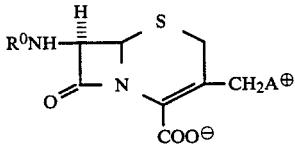

wherein R$^o$ is a group of the formula·

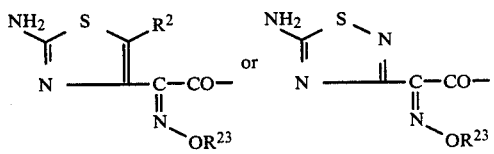

in which R² denotes hydrogen atom or halogen atom and R²³ denotes $C_{1-3}$ alkyl group optionally substituted with halogen atom, hydroxyl group, $C_{1-6}$ alkoxy group, carboxyl group, $C_{1-6}$ alkoxycarbonyl group or cyano group, and A stands for pyrazolo[1,5-a]pyridinium-3-yl group which may be substituted with hydroxyl group, $C_{1-6}$ alkyl group or carboxyl group, or a physiologically or pharmaceutically acceptable salt or ester thereof.

3. A compound according to claim 2, namely 7β-[2-(2-aminothiazol-4-yl)-2(Z)-methoxyiminoacetamido]-3-[(pyrazolo[1,5-a]pyridinium-3-yl)methyl]-3-cephem-4-carboxylate.

4. A compound according to claim 2, namely 7β-[2-(2-aminothiazol-4-yl)-2(Z)-methoxyiminoacetamido]-3-[(7-methylpyrazolo[1,5-a]pyridinium-3-yl)methyl]-3-cephem-4-carboxylate.

5. A compound according to claim 2, namely 7β-[2-(2-aminothiazol-4-yl)-2(Z)-(1-carboxy-1-methylethoxyimino)acetamido]-3-[(pyrazolo[1,5-a]pyridinium-3-yl)methyl]-3-cephem-4-carboxylate.

6. A compound according to claim 2, namely 7β-[2-(2-aminothiazol-4-yl)-2(Z)-methoxyiminoacetamido]-3-[(7-carboxypyrazolo[1,5-a]pyridinium-3-yl)methyl]-3-cephem-4-carboxylate.

7. A compound according to claim 2, namely 7β-[2-(2-amino-5-chlorothiazol-4-yl)-2(Z)-methoxyiminoacetamido]-3-[(pyrazolo[1,5-a]pyridinium-3-yl)methyl]-3-cephem-4-carboxylate.

8. A compound according to claim 2, namely 7β-[2-(5-amino-1,2,4-thiadiazol-3-yl)-2(Z)-methoxyiminoacetamido]-3-[(pyrazolo[1,5-a]pyridinium-3-yl)methyl]-3-cephem-4-carboxylate.

9. A compound according to claim 2, namely 7β-[2-(5-amino-1,2,4-thiadiazol-3-yl)-2(Z)-ethoxyiminoacetamido]-3-[(pyrazolo[1,5-a]pyridinium-3-yl)methyl]-3-cephem-4-carboxylate.

10. A pharmaceutical composition produced by mixing at least one of the cephem compounds claimed in claim 1, or physiologically or pharmaceutically acceptable salts thereof and pharmaceutically acceptable carriers or excipients.

11. A pharmaceutical composition produced by mixing the cephem compound of claim 3 and a pharmaceutically acceptable carrier or excipient.

12. A pharmaceutical composition produced by mixing the cephem compound of claim 4 and a pharmaceutically acceptable carrier or excipient.

13. A pharmaceutical composition produced by mixing the cephem compound of claim 5 and a pharmaceutically acceptable carrier or excipient.

14. A pharmaceutical composition produced by mixing the cephem compound of claim 6 and a pharmaceutically acceptable carrier or excipient.

15. A pharmaceutical composition produced by mixing the cephem compound of claim 7 and a pharmaceutically acceptable carrier or excipient.

16. A pharmaceutical composition produced by mixing the cephem compound of claim 8 and a pharmaceutically acceptable carrier or excipient.

17. A pharmaceutical composition produced by mixing the cephem compound of claim 9 and a pharmaceutically acceptable carrier or excipient.

* * * * *